(12) United States Patent
Aljuri et al.

(10) Patent No.: US 9,364,251 B2
(45) Date of Patent: Jun. 14, 2016

(54) AUTOMATED IMAGE-GUIDED TISSUE RESECTION AND TREATMENT

(71) Applicant: PROCEPT BioRobotics Corporation, Redwood City, CA (US)

(72) Inventors: Nikolai Aljuri, Hillsborough, CA (US); Surag Mantri, Sunnyvale, CA (US); Luis Baez, Mountain View, CA (US); George Surjan, Redwood City, CA (US); Michael W. Sasnett, Los Altos, CA (US); Jonathan Foote, San Francisco, CA (US)

(73) Assignee: PROCEPT BioRobotics Corporation, Redwood City, CA (US)

(*) Notice: Subject to any disclaimer, the term of this patent is extended or adjusted under 35 U.S.C. 154(b) by 0 days.

(21) Appl. No.: 14/334,247

(22) Filed: Jul. 17, 2014

(65) Prior Publication Data

US 2015/0057646 A1 Feb. 26, 2015

Related U.S. Application Data

(63) Continuation of application No. PCT/US2013/028441, filed on Feb. 28, 2013.

(60) Provisional application No. 61/604,932, filed on Feb. 29, 2012.

(51) Int. Cl.
*G06K 9/00* (2006.01)
*A61B 17/3203* (2006.01)
(Continued)

(52) U.S. Cl.
CPC .............. *A61B 17/3203* (2013.01); *A61B 1/307* (2013.01); *A61B 17/32037* (2013.01);
(Continued)

(58) Field of Classification Search
CPC .................. A61B 2019/504; A61B 2019/507; A61B 2019/508; A61B 2019/5255; A61B 2019/5263; A61B 2019/5265; A61B 2019/5276; A61B 2019/5278; A61B 2019/528; G06T 2207/3004–2207/30096
See application file for complete search history.

(56) References Cited

U.S. PATENT DOCUMENTS

| 4,474,251 A | 10/1984 | Johnson |
| 4,672,963 A | 6/1987 | Barken |

(Continued)

FOREIGN PATENT DOCUMENTS

| EP | 1075853 A2 | 2/2001 |
| JP | 2001-046528 A | 2/2001 |

(Continued)

OTHER PUBLICATIONS

U.S. Appl. No. 14/708,910, filed May 11, 2015, Aljuri et al.

(Continued)

*Primary Examiner* — Stephen R Koziol
*Assistant Examiner* — Timothy Choi
(74) *Attorney, Agent, or Firm* — Wilson, Sonsini, Goodrich & Rosati

(57) ABSTRACT

A system to treat a patient comprises a user interface that allows a physician to view an image of tissue to be treated in order to develop a treatment plan to resect tissue with a predefined removal profile. The image may comprise a plurality of images, and the planned treatment is shown on the images. The treatment probe may comprise an anchor, and the image shown on the screen may have a reference image marker shown on the screen corresponding to the anchor. The planned tissue removal profile can be displayed and scaled to the image of the target tissue of an organ such as the prostate, and the physician can adjust the treatment profile based on the scaled images to provide a treatment profile in three dimensions. The images shown on the display may comprise segmented images of the patient with treatment plan overlaid on the images.

23 Claims, 67 Drawing Sheets

(51) Int. Cl.

| | |
|---|---|
| *A61B 18/04* | (2006.01) |
| *A61B 18/14* | (2006.01) |
| *A61B 1/307* | (2006.01) |
| *A61B 18/22* | (2006.01) |
| A61B 18/20 | (2006.01) |
| A61B 18/00 | (2006.01) |
| A61B 17/00 | (2006.01) |
| A61B 17/30 | (2006.01) |

(52) U.S. Cl.
CPC ............. *A61B18/04* (2013.01); *A61B 18/1485* (2013.01); *A61B 18/22* (2013.01); *A61B 18/20* (2013.01); *A61B 2017/00274* (2013.01); *A61B 2017/306* (2013.01); *A61B 2018/005* (2013.01); *A61B 2018/0044* (2013.01); *A61B 2018/0066* (2013.01); *A61B 2018/00279* (2013.01); *A61B 2018/00285* (2013.01); *A61B 2018/00327* (2013.01); *A61B 2018/00351* (2013.01); *A61B 2018/00404* (2013.01); *A61B 2018/00446* (2013.01); *A61B 2018/00488* (2013.01); *A61B 2018/00494* (2013.01); *A61B 2018/00517* (2013.01); *A61B 2018/00529* (2013.01); *A61B 2018/00541* (2013.01); *A61B 2018/00547* (2013.01); *A61B 2018/00577* (2013.01); *A61B 2018/00589* (2013.01); *A61B 2018/00595* (2013.01); *A61B 2018/00601* (2013.01); *A61B 2018/00607* (2013.01); *A61B 2018/00642* (2013.01); *A61B 2018/00982* (2013.01); *A61B 2018/00994* (2013.01); *A61B 2018/046* (2013.01); *A61B 2018/1472* (2013.01); *A61B 2018/2085* (2013.01); *A61B 2018/2211* (2013.01); *A61B 2018/2272* (2013.01); *A61B 2034/2048* (2016.02); *A61B 2034/254* (2016.02); *A61B 2090/3782* (2016.02); *A61B 2218/002* (2013.01); *A61B 2218/007* (2013.01)

(56) References Cited

U.S. PATENT DOCUMENTS

| | | | |
|---|---|---|---|
| 5,135,482 | A | 8/1992 | Neracher |
| 6,228,046 | B1 | 5/2001 | Brisken |
| 6,440,105 | B1 | 8/2002 | Menne |
| 7,882,841 | B2 | 2/2011 | Aljuri et al. |
| 8,092,507 | B2 | 1/2012 | Tomasello et al. |
| 8,814,921 | B2 | 8/2014 | Aljuri et al. |
| 2002/0022869 | A1 | 2/2002 | Hareyama et al. |
| 2003/0036768 | A1 | 2/2003 | Hutchins et al. |
| 2003/0139041 | A1 | 7/2003 | LeClair |
| 2005/0004516 | A1 | 1/2005 | Vanney |
| 2005/0256517 | A1 | 11/2005 | Boutoussov |
| 2006/0089626 | A1* | 4/2006 | Vlegele .............. A61B 17/3403 606/1 |
| 2006/0149193 | A1 | 7/2006 | Hall |
| 2007/0230757 | A1 | 10/2007 | Trachtenberg et al. |
| 2009/0018533 | A1 | 1/2009 | Perkins et al. |
| 2009/0088775 | A1 | 4/2009 | Swarup et al. |
| 2009/0227998 | A1* | 9/2009 | Aljuri .............. A61B 17/32037 606/13 |
| 2010/0076269 | A1 | 3/2010 | Makower et al. |
| 2010/0145254 | A1 | 6/2010 | Shadduck et al. |
| 2010/0179522 | A1* | 7/2010 | Companion ........... A61B 18/22 606/10 |
| 2011/0184291 | A1* | 7/2011 | Okamura ............... A61B 8/483 600/443 |
| 2011/0184391 | A1 | 7/2011 | Aljuri et al. |
| 2012/0157841 | A1* | 6/2012 | Glaenzer ................ A61B 8/12 600/439 |
| 2013/0253484 | A1 | 9/2013 | Aljuri |
| 2013/0253488 | A1 | 9/2013 | Aljuri et al. |
| 2013/0261540 | A1 | 10/2013 | Crank |
| 2013/0267889 | A1 | 10/2013 | Aljuri et al. |
| 2015/0045777 | A1 | 2/2015 | Aljuri et al. |
| 2015/0088107 | A1 | 3/2015 | Aljuri et al. |
| 2015/0088110 | A1 | 3/2015 | Aljuri et al. |
| 2015/0313666 | A1 | 11/2015 | Aljuri et al. |
| 2015/0335344 | A1 | 11/2015 | Aljuri et al. |

FOREIGN PATENT DOCUMENTS

| | | |
|---|---|---|
| JP | 2007-020837 A | 2/2007 |
| WO | WO 03/088833 A1 | 10/2003 |
| WO | WO 2004/080529 A2 | 9/2004 |
| WO | WO 2007/114917 A2 | 10/2007 |
| WO | WO 2008/083407 A1 | 7/2008 |
| WO | WO 2009/111736 A1 | 9/2009 |
| WO | WO 2009/152613 A1 | 12/2009 |
| WO | WO 2010/144419 A2 | 12/2010 |
| WO | WO 2011/097505 A1 | 8/2011 |
| WO | WO 2011/100753 A2 | 8/2011 |
| WO | WO 2011/141775 A1 | 11/2011 |
| WO | WO 2013/130895 A1 | 9/2013 |

OTHER PUBLICATIONS

U.S. Appl. No. 14/816,747, filed Aug. 3, 2015, Aljuri et al.
International search report and written opinion date Mar. 10, 2015 for PCT Application No. US2014/054412.
Nishimura, et al. Similarity Law on Shedding Frequency of Cavitation Cloud Induced by a Cavitating Jet. Journal of Fluid Science and Technology, vol. 7, No. 3, 2012, pp. 405-420.
Wright, et al. Cavitation of a submerged jet. Exp Fluids (2013) 54:1541.
U.S. Appl. No. 14/540,310, filed Nov. 13, 2014, Aljuri et al.
U.S. Appl. No. 14/540,331, filed Nov. 13, 2014, Aljuri et al.
International search report and written opinion dated Jun. 27, 2013 for PCT/US2013/028441.
European search report and opinion date Sep. 11, 2015 for EP Application No. 13754453.2.
Extended European search report and opinion dated Jan. 25, 2016 for EP Application No. 13754453.2.
Office action dated Dec. 9, 2015 for U.S. Appl. No. 14/540,331.
Office action dated Mar. 25, 2016 for U.S. Appl. No. 14/540,310.

* cited by examiner

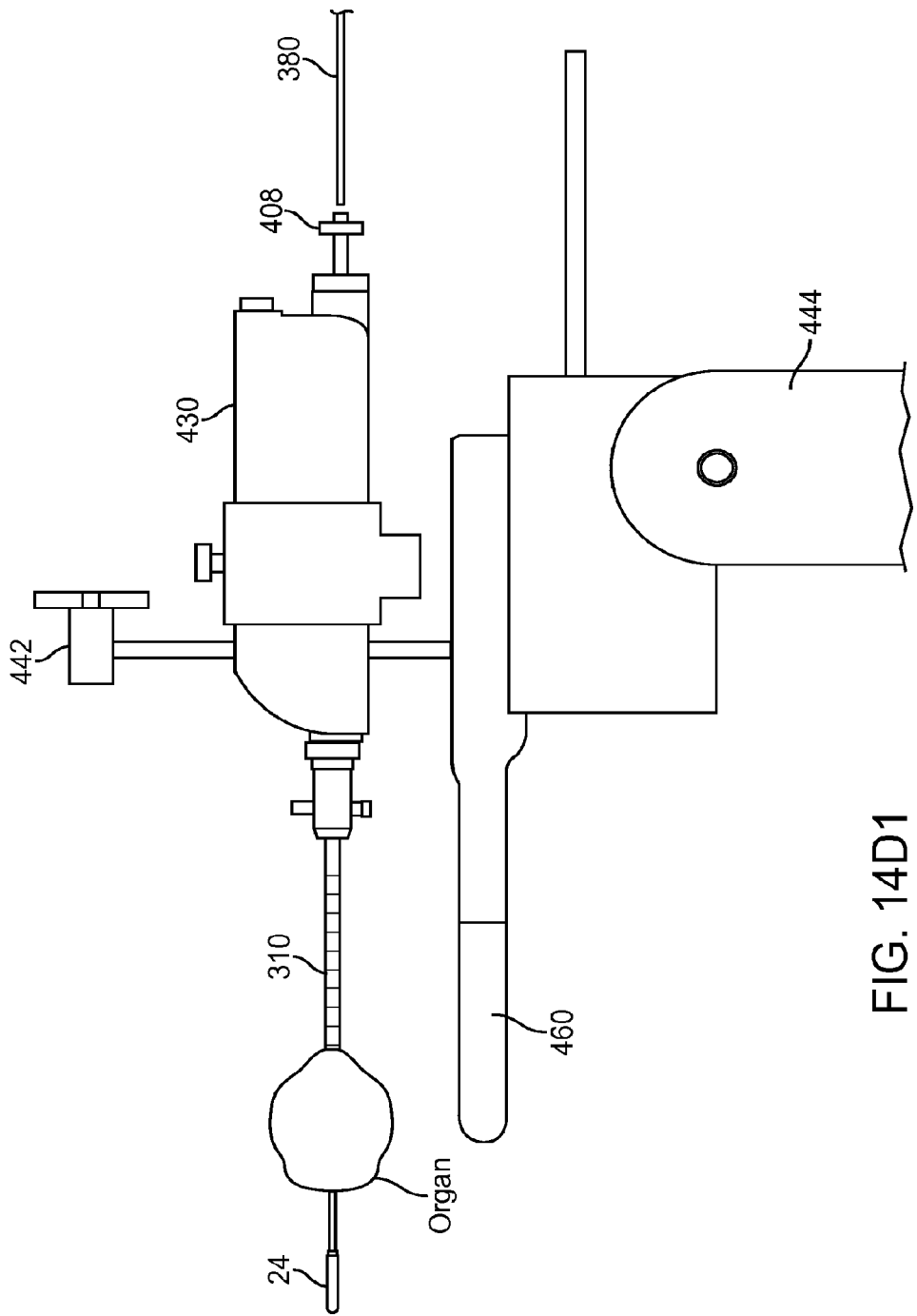
FIG. 14D1

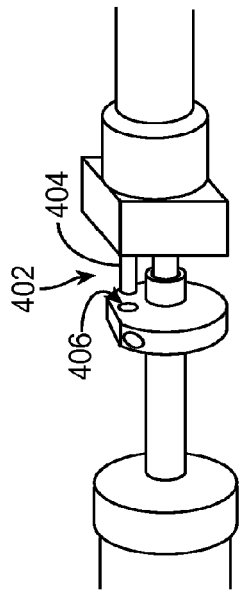
FIG. 14D3
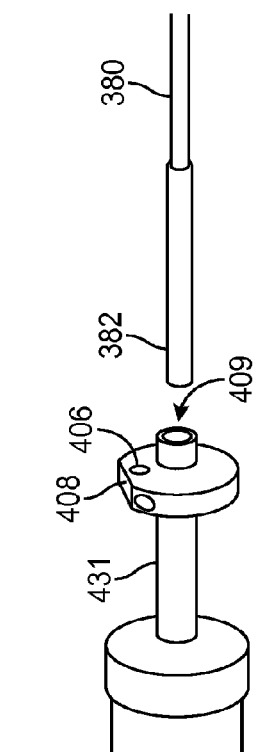
FIG. 14D2
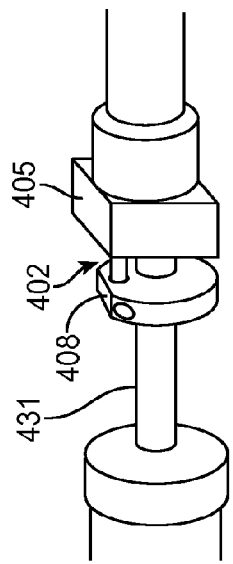
FIG. 14D4

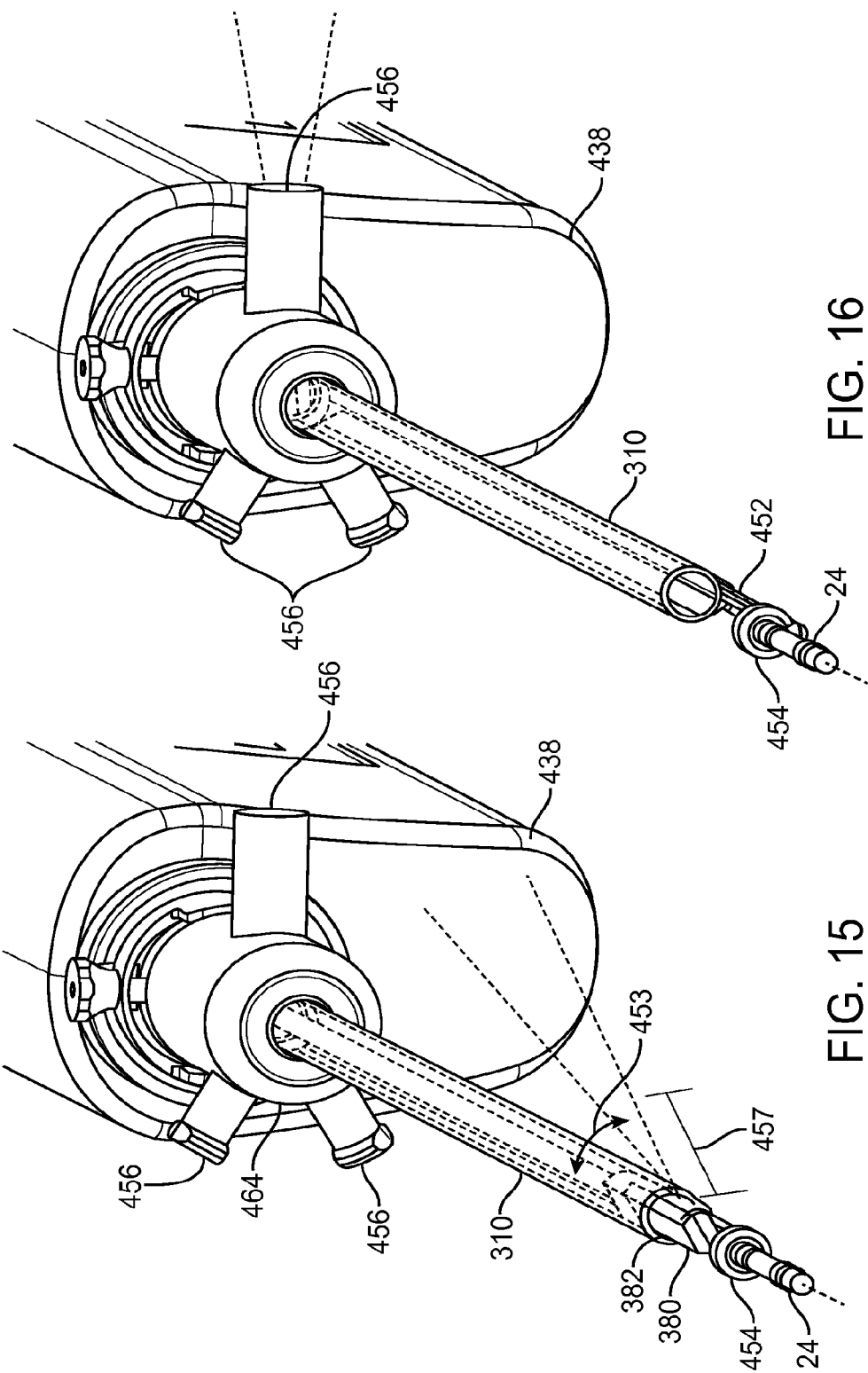

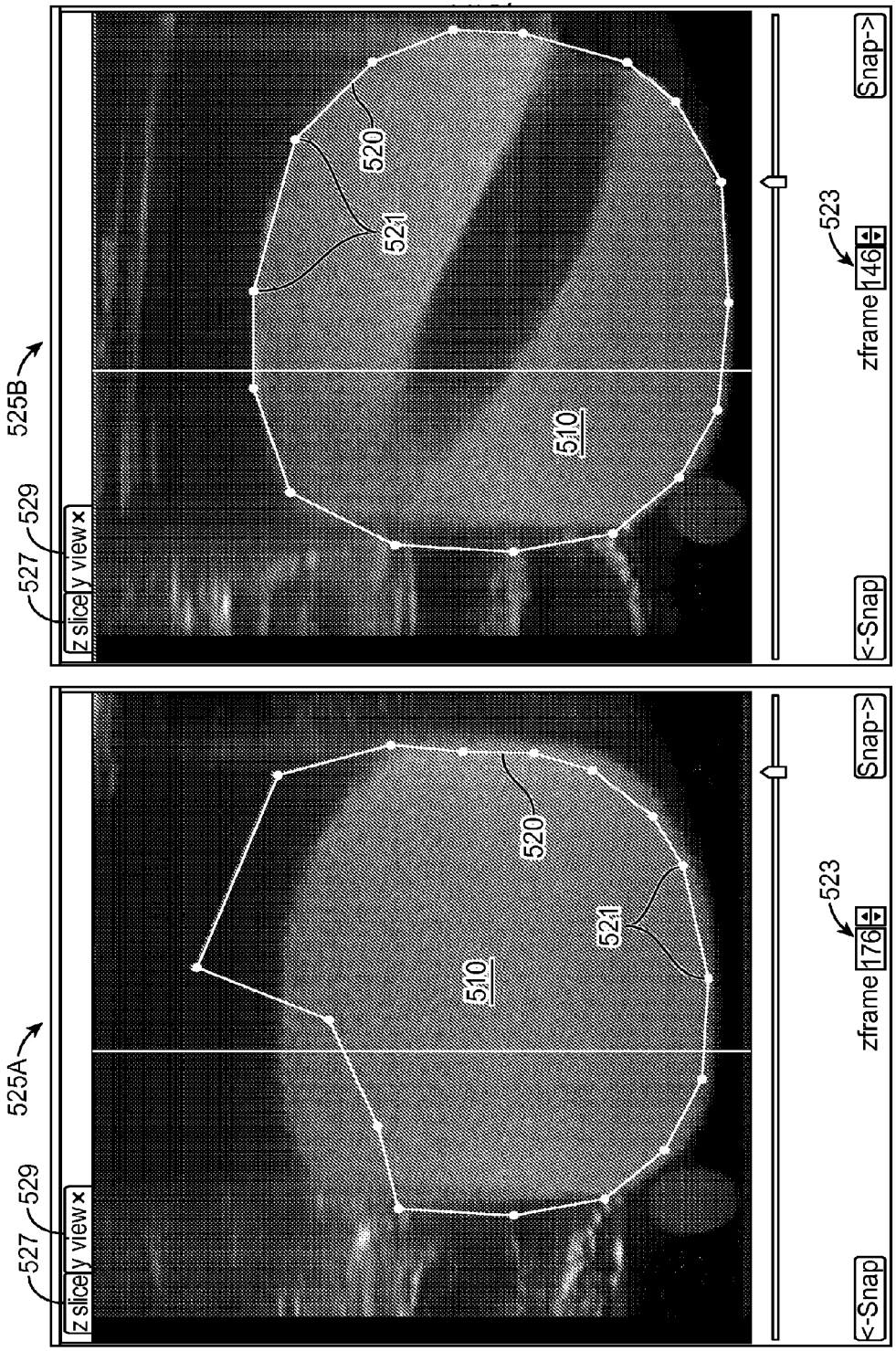

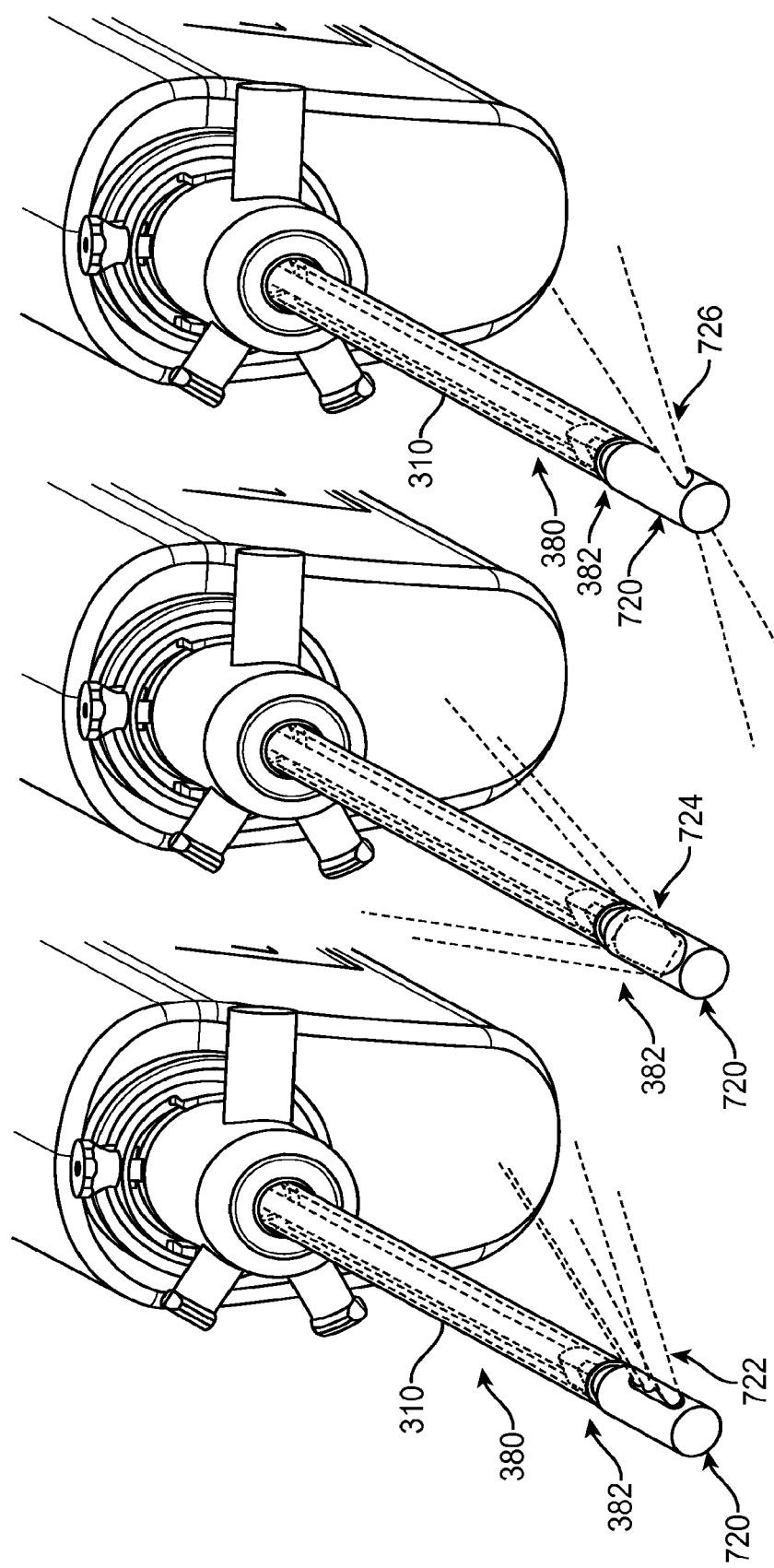

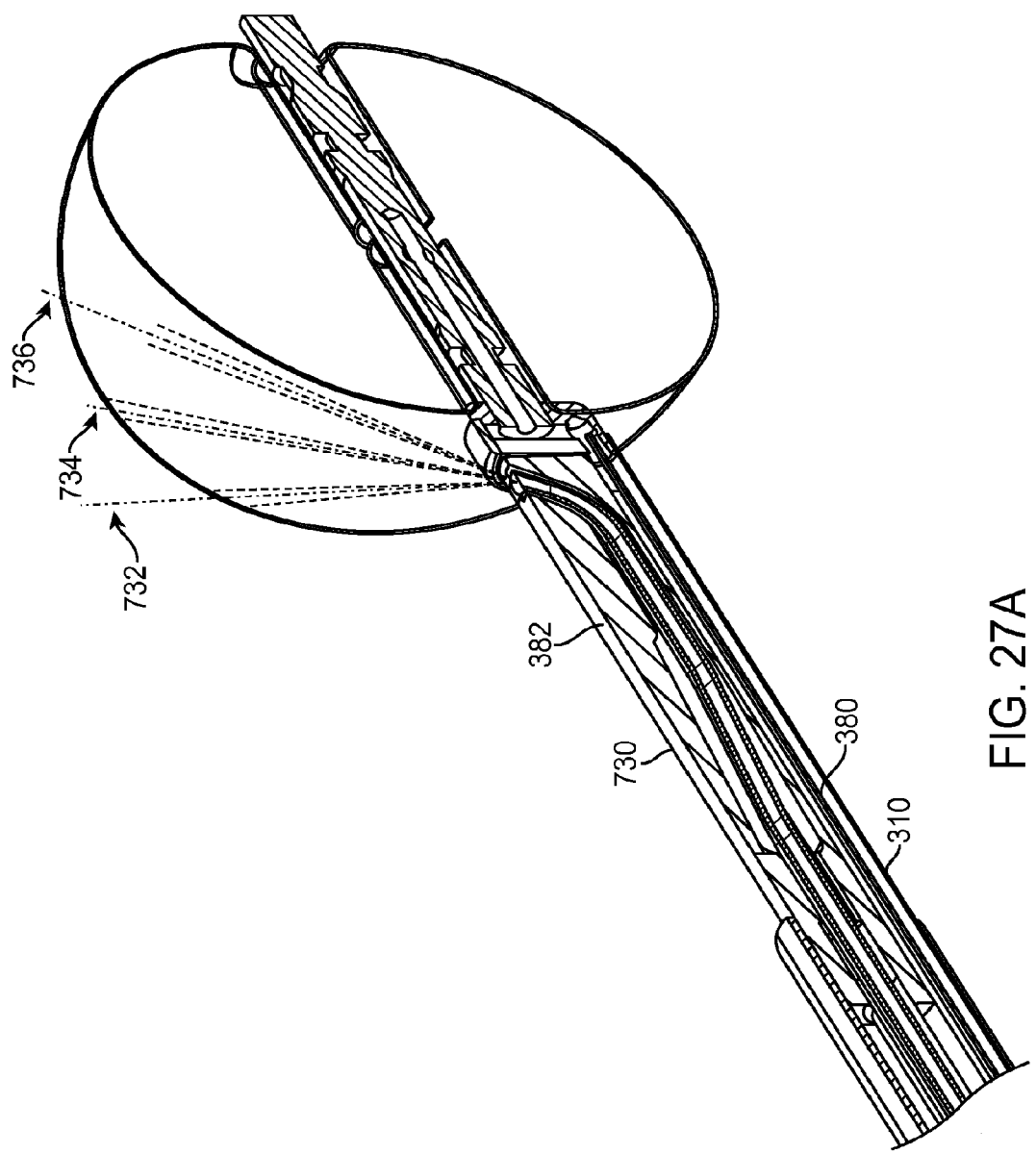

AUTOMATED IMAGE-GUIDED TISSUE RESECTION AND TREATMENT

CROSS-REFERENCE

This application is a continuation application of PCT/US2013/028441 filed, Feb. 28, 2013, which claims priority to U.S. Provisional Patent Application Ser. No. 61/604,932, filed Feb. 29, 2012, entitled "AUTOMATED IMAGE-GUIDED INTRA-ORGAN RESECTION AND TREATMENT", the entire disclosure of which is incorporated herein by reference.

This subject matter of this application is related to and incorporates by reference the complete disclosures of the following U.S. Patents and pending applications: Ser. No. 12/399,585, filed Mar. 6, 2009, entitled "TISSUE ABLATION AND CAUTERY WITH OPTICAL ENERGY CARRIED IN FLUID STREAM" published as US 2009/0227998, now U.S. Pat. No. 8,814,921, issued Aug. 26, 2014; application Ser. No. 12/700,568, filed Feb. 4, 2010, entitled "MULTI FLUID TISSUE RESECTION METHODS AND DEVICES", published as US 2011/0184391, now U.S. Pat. No. 9,232,959, issued Jan. 12, 2016; and U.S. Pat. No. 7,882,841, issued Feb. 8, 2011, entitled "MINIMALLY INVASIVE METHODS AND DEVICES FOR THE TREATMENT OF PROSTATE DISEASES".

The subject matter of the present application is also related to PCT Application PCT/US2011/023781 filed on Apr. 8, 2007, published as WO2011097505 on Nov. 8, 2011, entitled "MULTI FLUID TISSUE RESECTION METHODS AND DEVICES", the full disclosure of which is incorporated herein by reference.

BACKGROUND

The field of the present invention is related to the treatment of tissue with energy, and more specifically to the treatment of an organ such as the prostate with fluid stream energy.

Prior methods and apparatus of treating subjects such as patients can result in less than ideal removal in at least some instances. For example, prior methods of prostate surgery can result in longer healing time and less than desirable outcome than would be ideal in at least some instances.

Prior methods and apparatus of imaging tissue can be less than ideal for imaging a treated tissue. For example, prior ultrasound methods and apparatus may not be well suited to view the treatment sight during treatment, and alignment of diagnostic images with treatment images can be less than ideal. Also, at least some of the prior treatment methods and apparatus of treating tissue may not be well suited from combination with imaging systems of the prior art. In at least some instances, it would be helpful to provide improved imaging of tissue during surgery, for example to provide real time imaging of tissue that would allow a user to adjust the treatment based on real time images of the tissue. At least some of the prior methods and apparatus to image tissue during surgery can be somewhat cumbersome to use, and can result in delays in the patient treatment.

Prior methods and apparatus to treat an organ such as the prostate may provide a user interface that is somewhat cumbersome for the user, and can provide less than ideal planning of the surgery. Also, at least some of the prior methods and apparatus to treat tissue such as the prostate tissue can be somewhat less accurate than would be ideal. In at least some instances, the prior methods and apparatus may provide a less than ideal user experience. Also, at least some of the prior interfaces may provide less than ideal coupling of the treatment apparatus with tissue structures.

Improved methods for tissue resection are described in U.S. Pat. No. 7,882,841 and pending applications U.S. Ser. Nos. 12/700,568 and 12/399,585. The methods and systems described in this patent and these patent applications rely on the positioning of a probe such as a uretheral probe, which directs a fluid stream radially outwardly for controlled resection of tissue such as the prostate and luminal tissues. Optionally, the fluid stream may be used to deliver light, electrical, heat or other energy sources to aid in resection and/or to cauterize the treated tissue.

While these methods are very effective and a significant advance over prior luminal tissue treatment protocols, it would be desirable to provide improvements to assist in more accurate tissue removal in both fully automated and physician assisted operating modes. At least some of these objectives will be met by the inventions described hereinafter.

SUMMARY

Embodiments of the present invention provide improved methods and apparatus for performing tissue resection, such as prostate tissue resection, by positioning an energy source within a urethra. Energy is directed radially outwardly from the energy source toward tissue that may comprise a wall of the urethra within the prostate. The energy source is moved to remove a pre-defined volume of tissue surrounding the lumen, and movement of the energy source is at least partially controlled by an automated controller.

In many embodiments, a user interface is proved that allows a physician to view an image of tissue to be treated, such prostate tissue. The image may comprise a plurality of images, and the planned treatment is shown on a display to the physician. The treatment probe may comprise an anchor, and the image shown on the screen may have a reference image maker shown on the screen corresponding to the anchor. The planned tissue removal profile can be displayed and scaled to the image of the target tissue of an organ such as the prostate, and the physician can adjust the treatment profile based on the scaled images. The treatment profile can be simultaneously overlaid on a plurality of images of the tissue to be treated. In many embodiments, sagittal and axial views of the tissue are displayed, and the treatment profile of the pre-defined volume shown on the sagittal and axial with a substantially similar scale as the images, such that the treatment can be planned.

In many embodiments, the treatment probe comprises a linkage coupled to an anchor to accurately direct energy to a targeted tissue location. In many embodiments, the linkage is fixed to the anchor with a spine extending between the anchor and the linkage to accurately direct energy to the target tissue when the anchor is placed inside the patient. The treatment probe may comprise an elongate structure having a working channel, and the elongate structure may comprise an elongate element such as a shaft. The elongate structure may comprise the spine to add stiffness and rigidity, and the anchor may be provided on a distal end of the elongate structure. A carrier such as a carrier tube moves within the working channel under control of a linkage coupled to a controller. The linkage comprises a first fixed portion to provide a reference frame and a second moving portion to drive the carrier with rotation and translation in order to direct energy to the target location when the anchor is fixed to the linkage.

In many embodiments, a coordinate reference system of the treatment probe is shown on the display, and the images shown on the display are mapped to the coordinate reference system of the treatment probe, which makes it easier for the user to plan the treatment and ensures that the treatment is properly aligned with the tissue. The treatment probe may comprise a longitudinal axis, and the image of the tissue and tissue structures shown on the display can be referenced by the user with respect to the longitudinal axis treatment coordinate reference system. A radially extending resection distance of the profile may be shown on the display with reference to a radius extending from the longitudinal axis, and the radius can vary with an angle around the axis, so as to provide a pre-define volume having a three dimensional cut profile.

In many embodiments, an energy stream marker is shown on the images shown on the display, and the energy stream marker can be moved on the screen during treatment. The energy stream position can be shown on the sagittal and axial views. The position of the energy stream can vary rotationally along the axial view so as to correspond to sweeping motion of the energy stream around the longitudinal axis of the probe, and the longitudinal position of the energy stream can move along the sagittal image of the tissue and treatment profile so as to indicate the location of the energy stream along the longitudinal axis of the treatment. The images of the moving energy stream shown on the display can be shown in real time, so as to give the user an indication of the progress and completeness of the treatment.

The images of the tissue shown on the display may comprise user identifiable tissue structures, and may comprise tissue of an organ having an identifiable tissue structure of an organ such as the prostate. The image of the target tissue shown on the display may comprise one or more of an anatomical representation of the tissue to be treated, an image of the patient to be treated, a pre-operative image of the tissue to be treated, or a real-time image of the tissue of the patient when the patient is treated. The image of the target tissue shown on the display comprises structure of the target tissue, and may comprise an image of an organ containing the target tissue.

In many embodiments, a three dimensional data of the target tissue of the patient is obtained, and may be displayed to the user as a three dimensional representation. The three dimensional data may be shown in sagittal and axial cross sections, and the cross-sections may comprise segmentation of the targeted tissue. The three dimensional data can be obtained in one or more of many ways, and may comprise ultrasound data, magnetic resonance imaging data, positron emission tomography data, or computerized axial tomography data. In many embodiments, three dimensional data of the prostate are obtained, and segmented images along sagittal and transverse planes are displayed to the user.

The images of the patient shown on the display can be aligned mapped to the treatment coordinate reference system, and the mapped treatment profile shown on the patient images. The images of the patient may comprise one or more structures of the probe inserted into the patient, and the structures of the probe in the image can be identified in order to align the image with the markers of the treatment plan shown on the display. The identified structure of the image of the patient may comprise an anchoring balloon in an expanded configuration, and the balloon can be aligned with an anchor reference marker of the treatment plan.

Additional reference markers may be provided on the images to allow treatment planning, and in many embodiments, these reference markers can be verified prior to treatment. Additional structures of the patient image can be identified and aligned with the additional reference markers of the treatment plan in order to align the patient image with the treatment plan. The patient image can be mapped to the treatment probe coordinate reference system. Alternatively or in combination, the treatment plan comprising the treatment profile and pre-defined treatment volume can be mapped from the treatment probe coordinate reference system to the patient image coordinate reference system provided by an imaging probe.

In many embodiments, the treatment probe and imaging probe are coupled in order to provide accurate alignment of the treatment probe and imaging probe. The treatment probe and imaging probe can be coupled in many ways. In many embodiments the treatment probe and imaging probe are coupled with a common base. Alternatively or in combination, magnets can be provided to couple the imaging probe to the treatment probe. A first arm can extend from the base to the elongate treatment probe, and a second arm can extend from the base to the elongate imaging probe. The first arm and the second arm may each comprise a first movable configuration in which the arm can be moved to insert the probe into the patient and a second locked configuration in which movement of the arm is inhibited. The second arm may comprise actuators to allow fine movement and positioning of the imaging probe in order to align the imaging probe with the treatment probe and target tissue.

In many embodiments, angle sensors are provided to determine an angular orientation of one or more of the imaging probe of the treatment probe. Each angle sensor can be connected to the probe, for example fixed to the probe, such that the angle sensor can be used to determine an orientation of the elongate axis of the probe and rotation of the probe around the elongate axis. Each angular sensor may comprise one or more of a goniometer or an accelerometer, and may comprise a three dimensional angle sensor such as a three dimensional accelerometer.

The treatment probe and the imaging probe can be inserted into the patient in one or more of many ways. In many embodiments, the imaging probe is inserted into a first side of the patient and the treatment probe is inserted into a second side of the patient. The imaging probe may comprise a transrectal ultrasound probe inserted from a posterior side of the patient and the treatment probe is inserted into the urethra of the patient from an anterior side of the patient.

In many embodiments, the treatment probe is configured to image the target tissue. The treatment probe comprises an elongate structure having a working channel sized to receive an endoscope and a carrier of a carrier tube, and the carrier is configured to direct and scan a light beam on the treatment area to determine a profile of the tissue removed, and carrier may be configured to release a fluid stream comprising a waveguide and scan the light pattern the fluid stream comprising the waveguide. The profile of removed tissue can be determined based on locations of the light beam from endoscope images. Alternatively or in combination, the carrier may comprise at least one acoustic transducer to measure the location of remaining tissue and provide a tissue resection profile. The longitudinal location of the carrier and angular orientation of the carrier can be determined based on controller commands to the linkage used to position the carrier in relation to the anchor.

In many embodiments, a manifold is connected to a proximal end of the elongate structure, and a coupling joint is provided between the linkage and the manifold to allow the linkage to be decoupled from the patient when the elongate structure and anchor remain placed in the patient. The manifold comprises a plurality of ports and a plurality of channels that are coupled to the treatment site, for one or more of flushing, insufflation, or inflation of the anchoring balloon. The manifold that remains connected to the elongate structure having the working channel when the linkage is not connected has many advantages. The elongate structure can be configured in many ways, and the elongate structure may comprise an elongate tubular shaft structure that defines a working channel, a plurality of channels and a sheath. The working channel, the plurality of channels and the sheath of the elongate structure may extend from the manifold to the working site. In many embodiments, the elongate structure comprises a stiff element to add stiffness and rigidity, such as a spine extending from the manifold to the anchor and the spine may comprise a stiff or rigid tubular member. The manifold allows fluid delivery to the treatment site with the elongate structure with the one or more fluid delivery channels and a sheath extending around the spine. The surgical site can be accessed with surgical tools and imaging apparatus such as an endoscope when the anchor comprises an expanded configuration. The elongate structure can be advanced to the treatment site and the anchor expanded prior to coupling the linkage to the elongate structure.

In a first aspect, embodiments provide method for tissue resection. The method comprises positioning an energy source within tissue. Energy is directed radially outwardly from the energy source toward the tissue. The energy source is moved to remove a pre-defined volume of tissue, wherein movement of the energy source is at least partially controlled by an automated controller In another aspect, embodiments provide a method for tissue resection of an organ such as the prostate. An energy source is positioned within a urethra having a lumen. Energy is directed radially outwardly from the energy source toward a wall of the urethra within the prostate. The energy source is moved to remove a pre-defined volume of tissue surrounding the lumen, wherein movement of the energy source is at least partially controlled by an automated controller.

In many embodiments, the automated controller controls movement of the energy source based on a predetermined plan.

In many embodiments, the automated controller controls movement of the energy source based on a predetermined plan.

In many embodiments, the predetermined plan is input by a user based on pre-operative images of the prostate.

In many embodiments, the automated controller controls movement of the energy source based on real time assessment of the prostate.

In many embodiments, the real time assessment comprises interstitial, laser guided imaging.

In many embodiments, the real time assessment comprises acoustic distance measurement.

In many embodiments, the real time assessment comprises interstitial sound guided differentiation.

In many embodiments, the automated control further comprises pulse width modulation.

In many embodiments, a user overrides the automated control.

In many embodiments, an image of a prostate is provided on a display coupled to a processor, the display capable of being viewed by a user. A plurality of input parameters is received corresponding to an axial length and a radial distance of the pre-defined volume of tissue. A predefined tissue removal profile of the predefined volume is shown on the image of the prostate on the display based on the plurality of input parameters.

In many embodiments, the plurality of input parameters comprises one or more of a longitudinal distance of the removal profile, a radial distance of the removal profile, an angular distance of the removal profile around a longitudinal axis of the removal profile, an axis of the removal profile, a central location of the removal profile, or a user defined input removal profile in response to the user moving a pointer over the image of the prostate.

In many embodiments, the image of the prostate comprises an axial view of the prostate and a sagittal view of the prostate, and an axial view of the predefined tissue removal profile is shown on the axial view of the prostate and sagittal view of the tissue removal profile is shown on the sagittal view of the prostate.

In many embodiments, the axial view of the predefined removal profile is adjusted based on the radial distance and the angular distance of the predefined removal profile, and the axial view of the predefined removal profile is adjusted based on the axial distance and the radial distance of the predefined removal profile.

In many embodiments, the tissue removal profile shown on the image of the prostate comprises dimensions scaled to the image of the prostate shown on the display such that dimensions of the tissue removal profile shown on the display correspond to dimensions of the image of the prostate shown on the display.

In many embodiments, a treatment reference marker is shown with the image of the prostate and wherein the tissue removal profile is shown on the display in relation to the treatment reference marker based on the plurality of input parameters.

In many embodiments, the treatment reference marker shown on the display corresponds to an anchor connected to the energy source.

In many embodiments, the treatment reference marker shown on the display corresponds to an expandable anchor connected to the energy source and wherein the expandable anchor comprises a first narrow profile configuration sized for insertion into the lumen and a second wide profile configuration to inhibit passage through the lumen when placed in a neck of a bladder of the patient and wherein the treatment reference marker shown on the display comprises an image of an expandable anchor in a wide profile configuration on a superior end of the image of the prostate.

In many embodiments, the image of the prostate shown on the display comprises an image of the prostate of the patient or an anatomical representation of a prostate suitable for use with a plurality of patients.

In many embodiments, the image of the image of the prostate of the patient shown on the display comprises a transrectal ultrasound image of the prostate of the patient.

In many embodiments, a nozzle is identified among a plurality of nozzles to treat the patient with a pressurized fluid stream based on a radial distance of the tissue removal profile input into the processor.

In many embodiments, the tissue is coagulated with a light beam at a radial distance and an angular distance of a portion of the tissue removal profile subsequent to removal of the tissue with the pressurized fluid steam and wherein the angular distance corresponds to a posterior portion of the removal profile.

In many embodiments, the fluid stream comprises a divergent stream of a substantially incompressible fluid and wherein the light beam comprises a divergent light beam.

In many embodiments, a treatment axis of the pre-defined treatment volume is aligned with an axis of the patient based on an image of the prostate and energy emitted radially from the probe.

In many embodiments, the axis of the pre-defined volume comprises an anterior-posterior axis of the treatment volume, and the anterior-posterior axis of the treatment volume is aligned with an anterior posterior direction of the patient based on visualization of the tissue and an angle of energy emitted radially from the probe in order to rotationally align the treatment energy emitted from the probe with the anterior-posterior direction of the patient.

In many embodiments, the image comprises an ultrasound image showing one or more of deflection of the tissue or a fluid stream in response to pressurized fluid released from a nozzle, and an angle of the fluid stream around an elongate axis of a treatment probe is adjusted to align the treatment axis with the axis of the patient.

In many embodiments, the image comprises an optical image showing a light beam emitted radially from the probe illuminating the tissue and wherein an angle of the light beam around an elongate axis of the treatment probe is adjusted to align the treatment axis with the patient.

Many embodiments further comprises a processor, and the processor comprises instructions for the user to adjust an angle of the energy radially emitted from the treatment probe around an elongate axis of the treatment probe to align the energy radially emitted with an axis of the patient, and the processor comprises instructions to input the angle in response to a user command when the angle of the energy is aligned with the axis of the patient, and the processor comprises instructions to rotate the treatment axis based on the angle input into the processor.

In many embodiments, an angular rotation sensor determines a rotation of the treatment probe around an elongate axis of the probe in relation to an axis of the patient, and a treatment axis of the pre-defined treatment volume is rotated in response to the rotation of the treatment probe and wherein the patient is placed on a patient support such that an anterior posterior direction of the patient is aligned with a direction of gravitational pull.

In many embodiments, the angular rotation sensor comprises one or more of an accelerometer or a goniometer.

In another aspect, embodiments provide a tissue resection. A carrier has a proximal end and a distal end. At least one energy source on the carrier is spaced proximally to be positioned in the tissue when for delivering energy radially outwardly. An automated controller controls movement of the at least one energy source to effect volumetric tissue removal.

In another aspect, embodiments provide a tissue resection apparatus to resect tissue of an organ such as the prostate. The apparatus comprises a carrier having a proximal end and a distal end. At least one energy source on the carrier is spaced proximally to be positioned in the urethra when for delivering energy radially outwardly. An automated controller controls movement of the at least one energy source to effect volumetric tissue removal.

In many embodiments, the automated controller controls movement of the energy source based on a predetermined plan.

In many embodiments, the predetermined plan is input by a user based on pre-operative images of the prostate.

In many embodiments, the automated controller controls movement of the energy source based on real time assessment of the prostate obtained from an input device.

In many embodiments, the input device comprises an interstitial, laser guided imaging device.

In many embodiments, the input device comprises an interstitial, laser guided imaging device.

In many embodiments, the input device comprises an interstitial sound guided differentiation detector.

In many embodiments, the automated controller further comprises a pulse width modulation device.

Many embodiments further comprise means for the user to override the automated controller.

Many embodiments further comprise a processor comprising instructions configured:
to provide an image of a prostate on a display visible to a user; and
to receive a plurality of input parameters corresponding to an axial length and a radial distance of the pre-defined volume of tissue;
wherein a predefined tissue removal profile of the pre-defined volume is shown on the image of the prostate on the display based on the plurality of input parameters.

In many embodiments, the plurality of input parameters comprises one or more of a longitudinal distance of the removal profile, a radial distance of the removal profile, an angular distance of the removal profile around a longitudinal axis of the removal profile, an axis of the removal profile, a central location of the removal profile, or a user defined input removal profile in response to the user moving a pointer over the image of the prostate.

In many embodiments, the image of the prostate comprises an axial view of the prostate and a sagittal view of the prostate, and wherein an axial view of the predefined tissue removal profile is shown on the axial view of the prostate and sagittal view of the tissue removal profile is shown on the sagittal view of the prostate.

In many embodiments, the processor comprises instructions to adjust the axial view of the predefined removal profile based on the radial distance and the angular distance of the predefined removal profile and wherein the processor comprises instructions to adjust the axial view of the predefined removal profile based on the axial distance and the radial distance of the predefined removal profile.

In many embodiments, the tissue removal profile shown on the image of the prostate comprise dimensions scaled to the image of the prostate shown on the display such that dimensions of the tissue removal profile shown on the display correspond to dimensions of the image of the prostate shown on the display.

In many embodiments, the processor comprises instructions to show a treatment reference marker with the image of the prostate and to show the tissue removal profile on the display in relation to the treatment reference marker based on the plurality of input parameters.

In many embodiments, the treatment reference marker shown on the display corresponds to an anchor connected to the energy source.

In many embodiments, the treatment reference marker shown on the display corresponds to an expandable anchor connected to the energy source and wherein the expandable anchor comprises a first narrow profile configuration sized for insertion into the lumen and a second wide profile configuration to inhibit passage through the lumen when placed in a neck of a bladder of the patient and wherein the treatment reference marker shown on the display comprises an image of an expandable anchor in a wide profile configuration on a superior end of a sagittal image of the prostate.

In many embodiments, the treatment reference marker shown on the display comprises a fixed reference marker, and the processor comprises instructions to show a movable marker that moves in relation to the fixed reference marker and the treatment profile to show a location of an energy stream to a target tissue in real time.

In many embodiments, the movable marker is shown a plurality of images, the plurality of images comprising a sagittal image along a sagittal axis of treatment and an axial image transverse to the axis of treatment, and wherein the movable marker moves along the axis of treatment in the sagittal image and the movable marker rotates around the axis in the axial image and wherein the fixed reference marker is displayed on each of the plurality of images in relation to the movable marker.

In many embodiments, the image of the prostate shown on the display comprises an image of the prostate of the patient or an anatomical representation of a prostate suitable for use with a plurality of patients.

In many embodiments, the image of the image of the prostate of the patient shown on the display comprises a transrectal ultrasound image of the prostate of the patient.

In many embodiments, the processor comprises instructions to identify a nozzle among a plurality of nozzles to treat the patient with a pressurized fluid stream based on a radial distance of the tissue removal profile input into the processor.

In many embodiments, the processor comprises instructions to coagulate tissue with a light beam at a radial distance and an angular distance of a portion of the tissue removal profile subsequent to removal of the tissue with the pressurized fluid steam and wherein the angular distance corresponds to a posterior portion of the removal profile.

In many embodiments, the fluid stream comprises a divergent stream of a substantially incompressible fluid and wherein the light beam comprises a divergent light beam.

In many embodiments, a treatment axis of the pre-defined treatment volume is aligned with an axis of the patient based on an image of the prostate and energy emitted radially from the probe.

In many embodiments, the axis of the pre-defined volume comprises an anterior-posterior axis of the treatment volume and wherein the anterior-posterior axis of the treatment volume is aligned with an anterior posterior direction of the patient based on visualization of the tissue and an angle of energy emitted radially from the probe in order to rotationally align the treatment energy emitted from the probe with the anterior-posterior direction of the patient.

In many embodiments, the image comprises an ultrasound image showing one or more of deflection of the tissue or a fluid stream in response to pressurized fluid released from a nozzle and wherein an angle of the fluid stream around an elongate axis of a treatment probe is adjusted to align the treatment axis with the axis of the patient.

In many embodiments, image comprises an optical image showing a light beam emitted radially from the probe illuminating the tissue and wherein an angle of the light beam around an elongate axis of the treatment probe is adjusted to align the treatment axis with the patient.

Many embodiments further comprise a processor and wherein the processor comprises instructions for the user to adjust an angle of the energy radially emitted from the treatment probe around an elongate axis of the treatment probe to align the energy radially emitted with an axis of the patient and wherein the processor comprises instructions to input the angle in response to a user command when the angle of the energy is aligned with the axis of the patient and wherein the processor comprises instructions to rotate the treatment axis based on the angle input into the processor.

In many embodiments, an angular rotation sensor determines a rotation of the treatment probe around an elongate axis of the probe in relation to an axis of the patient and wherein a treatment axis of the pre-defined treatment volume is rotated in response to the rotation of the treatment probe and wherein the patient is placed on a patient support such that an anterior posterior direction of the patient is aligned with a direction of gravitational pull.

In many embodiments, the angular rotation sensor comprises one or more of an accelerometer or a goniometer.

Many embodiments further comprise a processor comprising instructions configured:
to provide a plurality of images of a tissue on a display visible to a user, each image of the plurality comprising a plane of a three dimensional representation of the tissue;
to receive input from the user to define a treatment profile along said each image of the plurality of images; and
to determine a three-dimensional treatment profile based on the treatment profile along said each of the plurality of images.

In many embodiments, the processor comprises instructions to interpolate among treatment profiles of the plurality of images to determine the three-dimensional treatment profile.

Many embodiments further comprise a non-pulsatile pump coupled to the carrier and the automated controller to provide a pulsed energy stream comprising a plurality of sequential pulses.

Many embodiments further comprise a pulsatile pump coupled to the carrier and the automated controller to provide a pulsed energy stream comprising a plurality of sequential pulses.

In many embodiments, the automated controller is configured to move the pulsed energy delivery stream such that the plurality of sequential pulses overlap at a target location of tissue to be removed.

In many embodiments, the automated controller is configured to move the pulsed energy delivery stream such that the plurality of sequential pulses do not overlap at a target location of tissue to be removed.

In another aspect, embodiments provide an apparatus to treat tissue of a patient. An elongate treatment probe to treat a patient extends along an axis. The elongate treatment probe comprises an outer elongate structure having a working channel and an inner carrier rotatable and translatable within the working channel to position and orient an energy source to release energy toward a target tissue. An elongate imaging probe, the elongate imaging probe extends along an axis. A coupling couples the elongate treatment probe to the elongate imaging probe when the elongate treatment probe and the elongate imaging probe have been inserted into the patient.

Many embodiments further comprise a first linkage connected to the inner carrier and a second linkage connected to the imaging probe, wherein one or more controllers is configured to move the first linkage together with the second linkage to move the inner carrier along a treatment axis and move the imaging probe along an imaging probe axis in order to view interaction of the carrier with tissue as the carrier moves along the axis.

In many embodiments, the coupling comprises:
a base;
a first arm extending from the base and connected to a proximal end of the elongate treatment probe; and
a second arm extending from the base and connected to a proximal end of the elongate imaging probe;
wherein the base supports the elongate treatment probe and the elongate imaging probe when the first arm comprises a stiff configuration and the second arm comprises a stiff configuration.

In many embodiments, the second arm comprises an actuator to manipulate the imaging probe under user control when the first arm maintains a position and orientation of the elongate treatment probe.

In many embodiments, the coupling is configured to maintain alignment of the elongate treatment probe in relation to the elongate imaging probe when the elongate imaging probe and the elongate treatment probe have been inserted from opposite sides of the patient.

In many embodiments, the coupling is configured to maintain an alignment of the axis of the elongate treatment probe with the axis of the elongate imaging probe when the nozzle is advanced proximally and distally and rotated.

In many embodiments, the coupling is configured to align the axis of the treatment probe parallel with the axis of the imaging probe.

In many embodiments, the coupling is configured to maintain a fixed position and orientation of the elongate imaging probe in relation to the elongate imaging probe.

In many embodiments, the coupling comprises a stiff arm coupled to the elongate treatment probe and a second stiff arm coupled to the elongate imaging probe, the first stiff arm fixedly coupled to the second stiff arm, and wherein the elongate treatment probe comprises stiffness to inhibit deflection transverse to the treatment probe axis and the elongate imaging probe comprises stiffness to inhibit deflection transverse to the elongate imaging probe axis.

In many embodiments, the coupling comprises magnets to maintain a fixed position and orientation of the elongate imaging probe in relation to the elongate imaging probe.

In many embodiments, the coupling comprises a plurality of magnets arranged at a plurality of axial locations along one or more of the elongate treatment probe or the elongate imaging probe.

In many embodiments, the coupling is configured to couple the elongate treatment probe to the elongate imaging probe through a wall of a first lumen extending over a portion of the elongate treatment probe and a wall of a second lumen extending over a portion of the elongate imaging probe.

In many embodiments, the elongate imaging probe is configured for insertion into a rectum of the patient and the elongate treatment probe is configured for insertion into a urethra of the patient and wherein the coupling is configured to align the elongate treatment probe with the elongate imaging probe when the elongate treatment probe is placed within the urethra and the elongate imaging probe is placed within the rectum.

In many embodiments, the elongate structure comprises a spine to add stiffness to the probe such that the elongate structure inhibits deflection of the probe transverse to the axis.

In many embodiments, the elongate imaging probe comprises at least a stiff distal portion to inhibit deflection of the imaging probe transverse to the axis of the imaging probe and to fix the orientation of the axis of the elongate imaging probe in relation to the axis of the elongate treatment probe.

In many embodiments, a processor is coupled to the elongate imaging probe, the elongate treatment probe and the linkage and wherein the processor comprises instructions to determine a pressure, an axial location and an orientation of the nozzle to ablate a target location of the tissue identified on an image of the elongate imaging probe.

In many embodiments, the processor comprises instructions to determine the pressure, the axial location and orientation of the nozzle in response to the target location on the image when the elongate treatment probe has been inserted on a first side of the patient and the elongate imaging probe has been inserted on a second side of the patient opposite the first side.

In many embodiments, the processor comprises instructions to determine the pressure, the axial location and orientation of the nozzle in response to the target location on the image when the elongate treatment probe has been coupled to the elongate imaging probe through a wall of a first lumen and a wall of a second lumen extending between the elongate treatment probe and the elongate imaging probe.

In many embodiments, the processor comprises instructions to determine a first image coordinate reference of a first input target location of the image and a second image coordinate reference of a second input target location of the image and instructions to map the first image coordinate reference of the image to a first target coordinate reference of the treatment probe and to map the second input target location of the image to a second target coordinate reference of the treatment probe and wherein the processor comprises instructions to determine pressures and axial and rotational positions of the nozzle to provide a cut profile extending from the first input target location to the second input target location.

In another aspect, embodiments provide an apparatus to treat tissue of a patient. An arm is coupled to a base. The arm comprises a first movable configuration and a second stiff configuration. A treatment probe to treat a patient comprises an outer elongate structure having a working channel and an inner carrier rotatable and translatable within the working channel to position and orient a nozzle to release a pressurized stream of fluid toward the tissue. A processor comprises instructions to rotate and translate the carrier to treat the patient. A linkage is coupled to the processor and the probe to rotate and translate the probe in response to the instructions.

In many embodiments, the carrier comprises a rapid exchange carrier configured to be inserted and removed from a proximal end of the outer elongate structure and wherein the linkage comprises a rotatable and translatable elongate linkage tube having an inner dimension sized to receive the inner carrier and wherein the elongate linkage tube comprises a locking structure to lock the rapid exchange carrier within the elongate linkage tube when the elongate linkage tube rotates and translates to treat tissue.

Many embodiments further comprise a manifold and a plurality of channels, the manifold connected to a proximal end of the outer elongate structure, the plurality of channels extending along the outer elongate structure to couple a first port of the manifold to a balloon anchor with a first channel and to couple a second port of the manifold with an opening near a distal end of the outer elongate fluid to deliver fluid to a treatment site and wherein the manifold comprises a locking structure and the linkage comprises a locking structure to connect the linkage to the manifold when the balloon has been inflated.

In many embodiments, the elongate structure comprises a spine coupled to an anchor, and wherein the spine extends between the anchor and the linkage to fix a distance from a first portion of the linkage to the anchor when the probe the carrier is rotated and translated with a second portion of the linkage to position and orient the nozzle to treat a target location of the patient referenced to the anchor.

In many embodiments, the elongate structure comprises is coupled to an anchor, and wherein the elongate structure extends between the anchor and the linkage to fix a distance along the elongate structure from a first portion of the linkage to the anchor when the carrier is rotated and translated with a second portion of the linkage to position and orient the nozzle to treat the patient.

In many embodiments, the elongate structure and the carrier are configured to deflect as the probe is inserted into the tissue and wherein the elongate structure maintains a substantially constant arc length between a fixed portion of the linkage and the anchor in order to maintain placement of the nozzle in relation to the anchor when nozzle is rotated and translated along the probe axis with the carrier to treat the patient.

In many embodiments, the linkage comprises an outer hand piece portion graspable and positionable with a hand of the user when the arm comprises an unlocked configuration.

In many embodiments, the linkage comprises a support coupled to the treatment probe and the arm to support the treatment probe and the linkage with the arm when the probe has been inserted into the patient.

In many embodiments, the support comprises one or more of a rigid casing of the linkage or a frame of the linkage and wherein the casing remains substantially fixed with the arm when the patient is treated.

In many embodiments, the support is coupled to the treatment probe to insert the probe in the patient and position the nozzle at a target location and orientation and wherein the support is coupled to the arm and the elongate structure in order to support the probe with the probe positioned and oriented within the patient when the arm comprises the stiff configuration.

In many embodiments, the support and arm are capable of supporting the linkage and the probe at an intended position and orientation when the arm comprises the stiff configuration in order to fix the location of the linkage when the patient is treated with the nozzle.

In many embodiments, the probe comprises an elongate structure and an inner carrier and wherein the linkage is coupled to the carrier to control a position the nozzle along an axis of the elongate structure and a rotation of the nozzle around the axis of the elongate structure.

In many embodiments, the apparatus is configured to remove living cells of the tissue in order to provide the living cells outside the patient.

In many embodiments, the apparatus is configured to remove tissue for histology.

In many embodiments, the apparatus is configured to macerate the tissue.

In many embodiments, the apparatus is configured to release a high pressure fluid stream into a gas comprising carbon dioxide (hereinafter "CO2").

In many embodiments, the apparatus comprises an optical fiber having bend radius of no more than about 5 mm.

In many embodiments, the apparatus comprises an optical fiber having a bend radius of no more than about 2 mm.

While embodiments of the present invention are specifically directed at transurethral treatment of the prostate, certain aspects of the invention may also be used to treat and modify other organs such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, as well as body lumens and passages such as the sinuses, ureter, colon, esophagus, lung passages, blood vessels, and throat. The devices disclosed herein may be inserted through an existing body lumen, or inserted through an opening created in body tissue.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 14D1 shows rapid exchange of a carrier when the linkage is coupled to the elongate element anchored to a target location of an organ, in accordance with embodiments;

FIG. 14D2 shows alignment of the distal tip of the carrier with the proximal end of the linkage to insert the carrier tube as in FIG. 14D1;

FIG. 14D3 shows the carrier advanced toward a locking structure on the proximal end of the linkage as in FIG. 14D1;

FIG. 14D4 shows the carrier locked to the linkage as in FIGS. 14D1 and 14D2;

FIGS. 15 and 16 show self cleaning with a fluid jet in accordance with embodiments;

FIGS. 21C to 21F show a plurality of axial images of a target tissue to define a three dimensional treatment plan and a user defined treatment profile in each of the plurality of images;

FIGS. 26A through 26C show jet masking in accordance with embodiments;

FIGS. 27A and 27B show variation of jet angle in accordance with embodiments;

DETAILED DESCRIPTION

Figure 1:
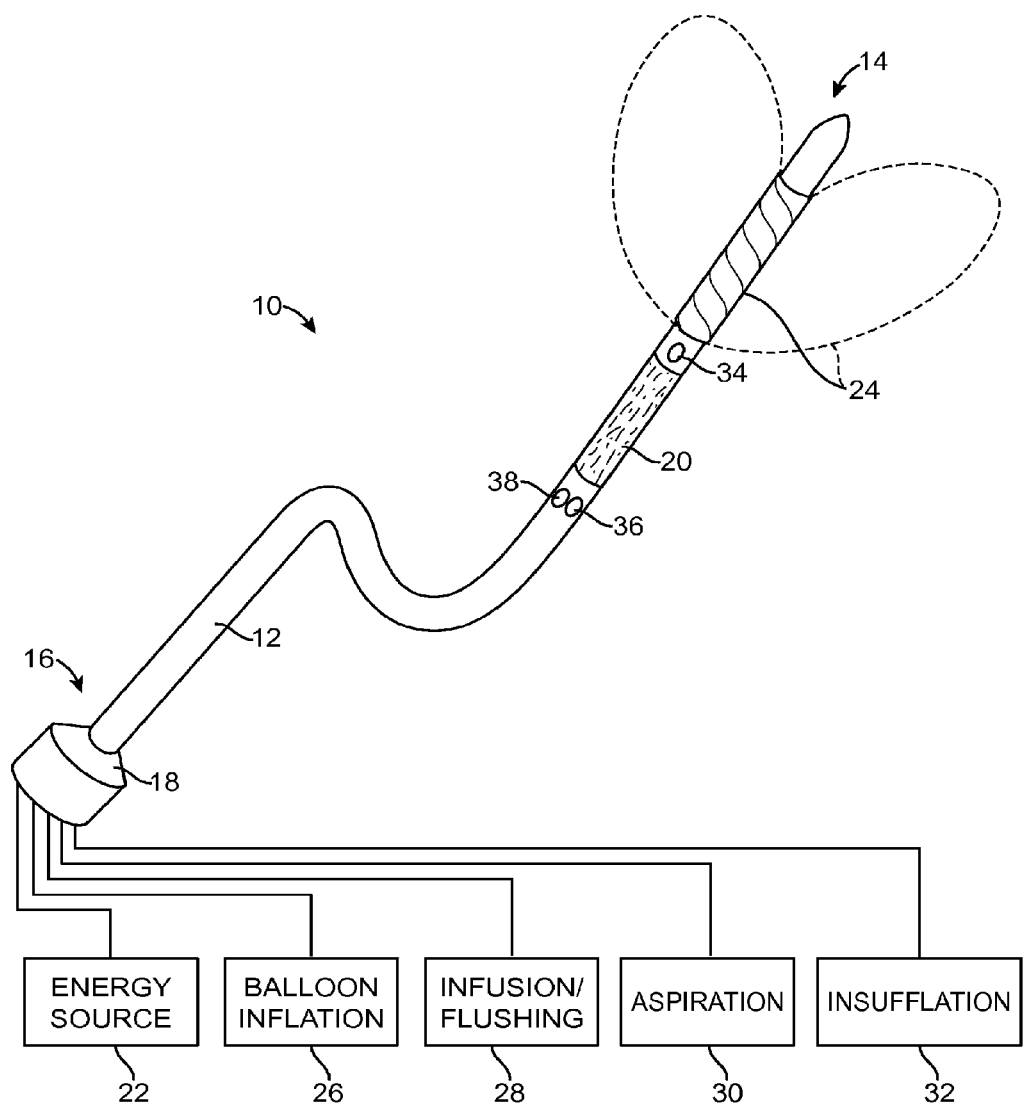
FIG. 1 is a schematic illustration of a device suitable for performing intraurethral prostatic tissue debulking in accordance with the principles of the present invention.

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described herein.

The embodiments disclosed herein can be combined in one or more of many ways to provide improved therapy to a patient. The disclosed embodiments can be combined with prior methods and apparatus to provide improved treatment, such as combination with known methods of prostate surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

Although the treatment planning and definition of treatment profiles and volumes as described herein are presented in the context of prostate surgery, the methods and apparatus as described herein can be used to treat any tissue of the body and any organ and vessel of the body such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone, etc. as well as body lumens and passages such as the sinuses, ureter, colon, esophagus, lung passages, blood vessels and throat.

The imaging and treatment probes as described herein can be combined in one or more of many ways, and in many embodiments the images of the patient can be used to define a target volume and a target profile of the volume of tissue removed. The profile of tissue removed can be planned to efficaciously remove tissue. The methods and apparatus for imaging as described herein can be used to beneficially plan for treatment. Alternatively or in combination, the imaging methods and apparatus as described herein can be used to modify the treatment in real time as the patient is treated, for example.

The visible entrainment region can be combined with the images of tissue and treatment regions shown on the display, so as to provide confirmation that the correct amount of tissue will be resected. In many embodiments, the distance of the visible entrainment region corresponds to a maximum cut depth, such that the surgeon can select the depth of the cut based on images and with adjustment of treatment parameters such as one or more of flow rate, nozzle diameter, or pressure.

The visible entrainment region as described herein comprises region of cavitation of the fluid stream emitted from the energy source such as a nozzle, and the maximum resection depth corresponds to the distance of the visible entrainment region. By visible entrainment region, it is meant that the user can visualize the entrainment region with imaging sensitive to formation of cavitation pockets, such as visible and ultrasound imaging which scatter waves in response to cavitation pockets being formed.

A plurality of carrier probes can be provided to allow the user to treat one or more of many tissues in a variety of ways. An elongate structural element having a working channel such as a shaft remains positioned in the patient when a first carrier probe is exchanged with one or more carrier probes. In many embodiments, the carrier probes can be rapidly exchanged while a linkage remains fixedly attached to the elongate element anchored to an internal structure of the patient. Each of the carrier probes inserted into the patient can be identified based on a treatment plan, for example.

As used herein a processor encompasses one or more processors, for example a single processor, or a plurality of processors of a distributed processing system for example. A controller or processor as described herein generally comprises a tangible medium to store instructions to implement a steps of a process, and the processor may comprise one or more of a central processing unit, programmable array logic, gate array logic, or a field programmable gate array, for example.

As used herein, the transverse plane of an image may be referred to as the horizontal plane of the image, the axial plane of the image, or transaxial plane of the image. An image along an axial plane may be referred to as an axial image.

As used herein, a probe encompasses an object inserted into a subject such as a patient.

As used herein like characters identify like elements.

As used herein, a real time image shown on a display encompasses an image shown within a few seconds of the event shown. For example, real time imaging of a tissue structure encompasses providing the real time image on a display within about ten seconds of the image being acquired.

As used herein, the terms distal and proximal refer to locations referenced from the apparatus, and can be opposite of anatomical references. For example a distal location of a probe may correspond to a proximal location of an elongate member of the patient, and a proximal location of the probe may correspond to a distal location of the elongate member of the patient.

Automated robotic control—where movement of the water jet is motorized and under computer control with preselected routines—allows accurate and finely detailed resections not possible with manual control. Advantages include reduced time required for procedures, fewer complications, improved outcomes and less training time needed for surgeons. Many of these improvements arise from reducing or eliminating the need for manual dexterity of the treating physician. Automatic control further allows the cutting power of the nozzle to be increased to levels not achievable with full manual control. The system may be manually controlled during less critical portions of the procedure, e.g. during initial selection of an area to operate on and for touch-ups in cutting and cautery. Even during these less critical phases of the protocols, the increased precision and smoothness provided by the automated control can provide reduction and filtering of hand jitter. Another significant advantage is that automation allows for pretesting or "dry runs" of a procedure. When a cutting routine is selected, the limits of area can be selected using a joystick or other control element to position the laser during a mock the procedure without cutting. Changes can be made before cutting commences, so that errors can be corrected before beginning the actual procedure.

Closed-loop and real-time automation are new capabilities provided by robotic automation include resection volume registration within the organ and in-situ depth and volume measurement. With the ability to input organ geometry data into the control system, e.g., from an ultrasound or other pre-operative or real time image, the cutting region can be precisely registered within the organ. This eliminates the imprecision of manual procedures with respect to important tolerances, such as to how close the resection is to the surface of the capsule and/or to the neurovascular bundle in the prostate. Additionally, the shape of the resected volume itself may be selectable and adjustable from a set of preprogrammed routines, where the details of how to control the cutting motion and pressure have been worked out in advance with extensive engineering knowledge that is then stored in the robotic surgical tool, ready for access at the push of a button by the surgeon. For example, the resected shape of tissue may comprise a pre-defined treatment profile such as one or more of domed, cubic, tear-drop, or directly from a 3D rendering of the target volume as described herein and illustrated below in the two screenshots of FIGS. 21A and 21B, for example. In addition, the surgeon can adjust the cutting parameters in real-time based on the feedback provided by the ultrasound images, which adds another layer of safety to the system.

INCORPORATION BY REFERENCE

The subject matter of FIGS. 1 to 11 and the corresponding text have been incorporated by reference as described in: U.S. application Ser. No. 12/700,568, filed Feb. 4, 2010, entitled "MULTI FLUID TISSUE RESECTION METHODS AND DEVICES", published as US 20110184391; and PCT Application PCT/US2011/023781 filed on Apr. 8, 2007, published as WO2011097505 on Nov. 8, 2011, entitled "MULTI FLUID TISSUE RESECTION METHODS AND DEVICES"; the full disclosures of which have been previously incorporated herein by reference.

Referring to FIG. 1, an exemplary prostatic tissue debulking device 10 constructed in accordance with the principles of the present invention comprises a catheter assembly generally including a shaft 12 having a distal end 14 and a proximal end 16. The shaft 12 will typically be a polymeric extrusion including one, two, three, four, or more axial lumens extending from a hub 18 at the proximal end 16 to locations near the distal end 14. The shaft 12 will generally have a length in the range from 15 cm to 25 cm and a diameter in the range from 1 mm to 10 mm, usually from 2 mm to 6 mm. The shaft will have sufficient column strength so that it may be introduced upwardly through the male urethra, as described in more detail below.

The shaft will include an energy source positioned in the energy delivery region 20, where the energy source can be any one of a number of specific components as discussed in more detail below. Distal to the energy delivery region, an inflatable anchoring balloon 24 will be positioned at or very close to the distal end 14 of the shaft. The balloon will be connected through one of the axial lumens to a balloon inflation source 26 connected through the hub 18. In addition to the energy source 22 and the balloon inflation source 26, the hub will optionally further include connections for an infusion/flushing source 28, an aspiration (a vacuum) source 30, and/or an insufflation (pressurized CO2 or other gas) source 32. In the exemplary embodiment, the infusion or flushing source 28 can be connected through an axial lumen (not shown) to one or more delivery ports 34 proximal to the balloon anchor 24 and distal to the energy delivery region 20. The aspiration source 30 can be connected to a second port or opening 36, usually positioned proximally of the energy delivery region 20, while the insufflation source 32 can be connected to an additional port 38, also usually located proximal of the energy delivery region. It will be appreciated that the locations of the ports 34, 36, and 38 are not critical, although certain positions may result in particular advantages described herein, and that the lumens and delivery means could be provided by additional catheters, tubes, and the like, for example including coaxial sleeves, sheathes, and the like which could be positioned over the shaft 12.

Figure 2A:
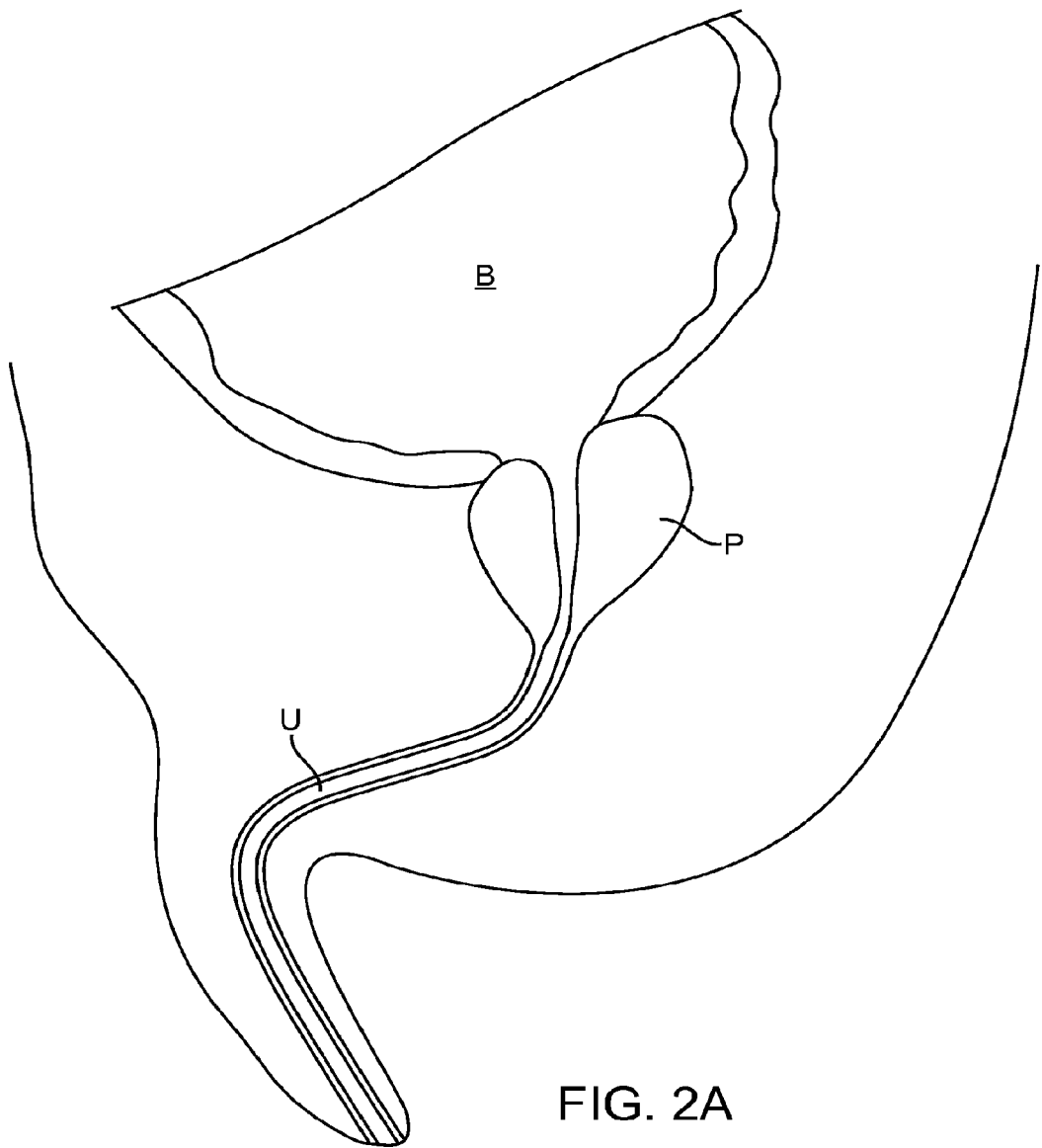
FIGS. 2A-2D illustrate use of the device of FIG. 1 in performing prostatic tissue debulking.
Figure 2B:
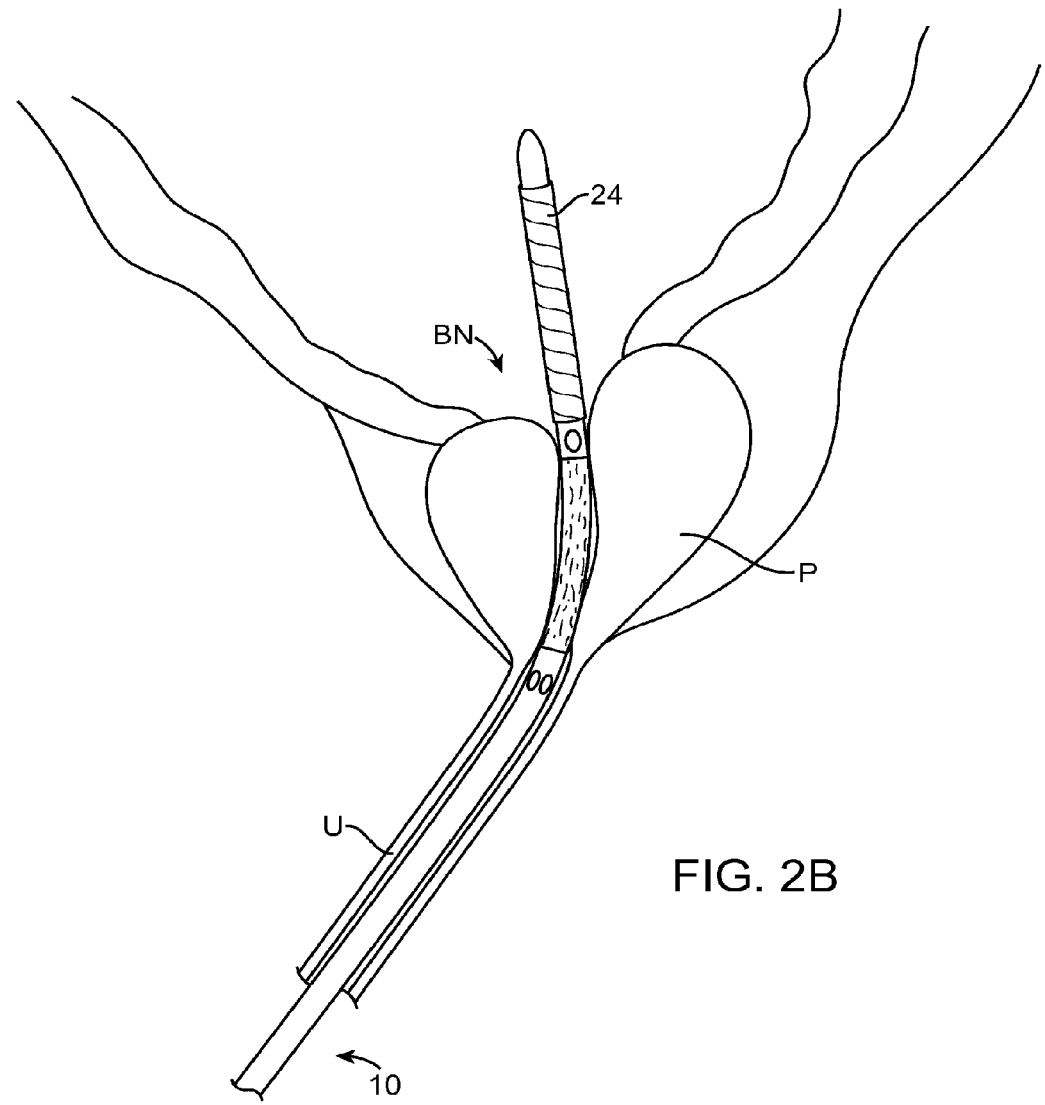
Figure 2C:
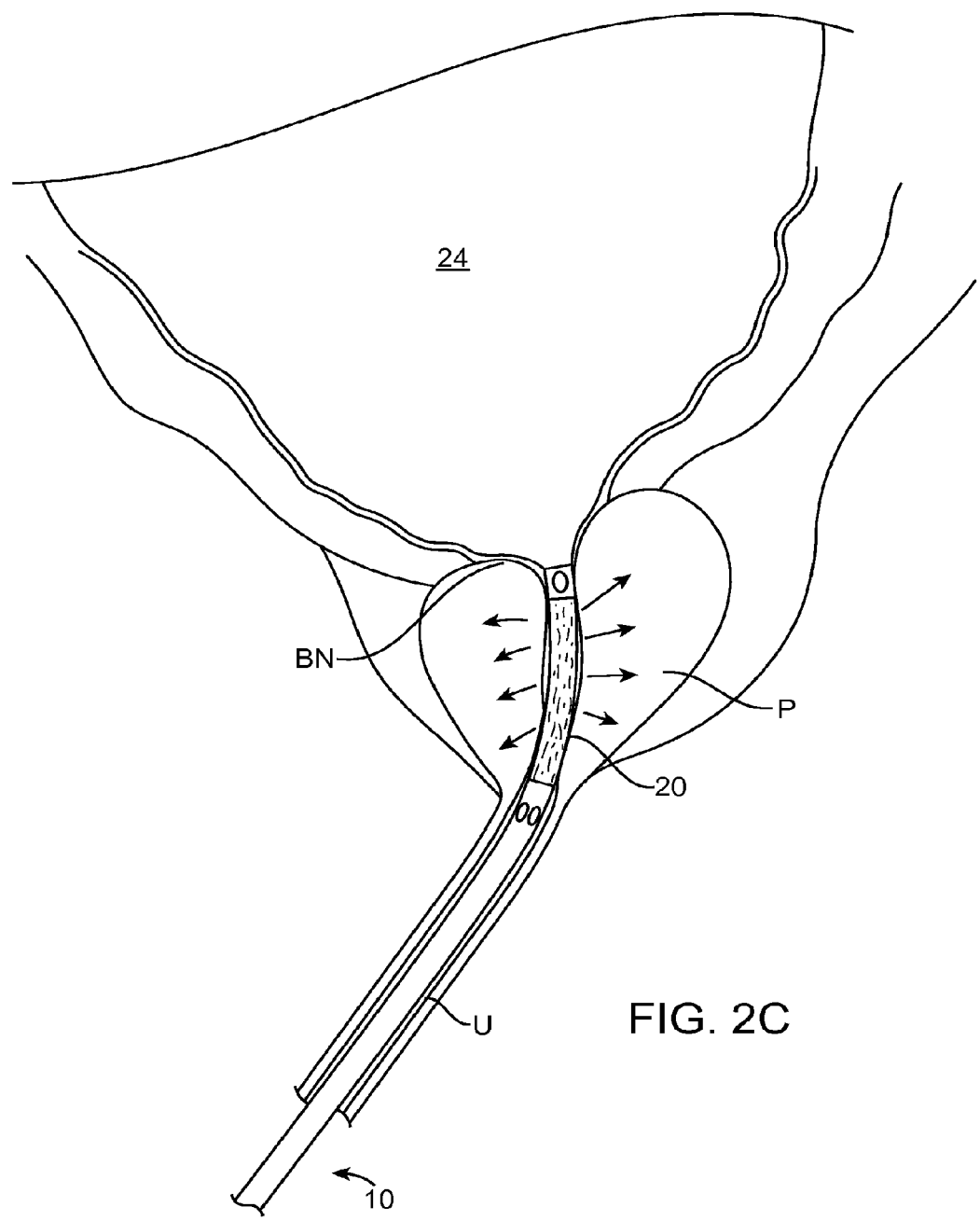
Figure 2D:
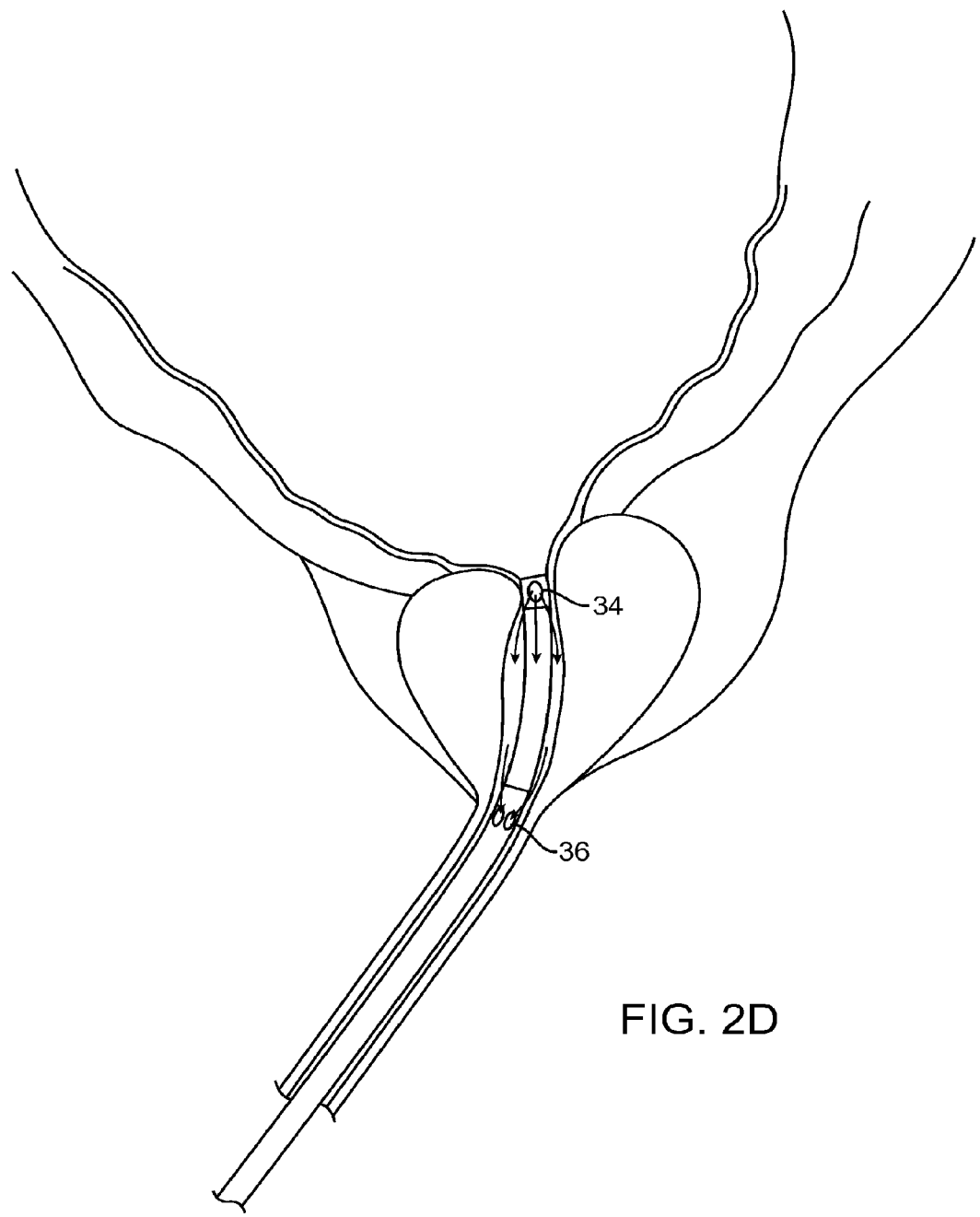

While the present embodiments are described with reference to the human prostate, it is understood that they may be used to treat mammal prostates in general. Referring now to FIGS. 2A-2D, the prostatic tissue debulking device 10 is introduced through the male urethra U to a region within the prostate P which is located immediately distal to the bladder B. The anatomy is shown in FIG. 2A. Once the catheter 10 has been positioned so that the anchoring balloon 24 is located just distal of the bladder neck BN (FIG. 2B) the balloon can be inflated, preferably to occupy substantially the entire interior of the bladder, as shown in FIG. 2C. Once the anchoring balloon 24 is inflated, the position of the prostatic tissue debulking device 10 will be fixed and stabilized within the urethra U so that the energy delivery region 20 is positioned within the prostate P. It will be appreciated that proper positioning of the energy delivery region 20 depends only on the inflation of the anchoring balloon 24 within the bladder. As the prostate is located immediately proximal to the bladder neck BN, by spacing the distal end of the energy delivery region very close to the proximal end of the balloon, typically within the range from 0 mm to 5 mm, preferably from 1 mm to 3 mm, the delivery region can be properly located. After the anchoring balloon 24 has been inflated, energy can be delivered into the prostate for debulking, as shown by the arrows in FIG. 2. Once the energy has been delivered for a time and over a desired surface region, the energy region can be stopped and the prostate will be debulked to relieve pressure on the urethra, as shown in FIG. 2D. At that time, a flushing fluid may be delivered through port 34 and aspirated into port 36, as shown in FIG. 2D. Optionally, after the treatment, the area could be cauterized using a cauterizing balloon and/or stent which could be placed using a modified or separate catheter device.

Figure 3:
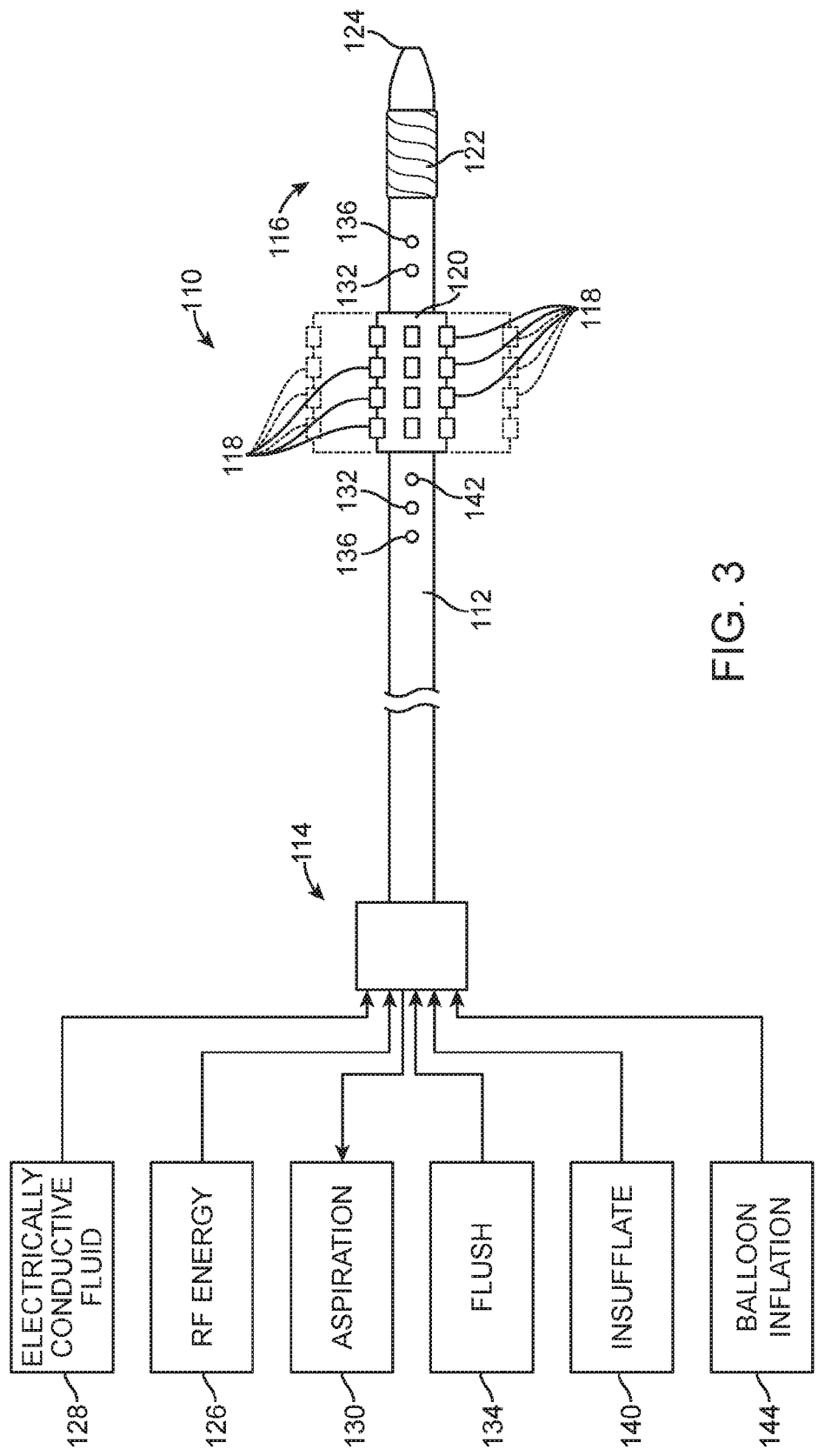
FIG. 3 illustrates a specific prostatic tissue treatment device incorporating the use of a radiofrequency saline plasma for performing prostatic tissue debulking.

Referring now to FIGS. 3-7, a number of representative energy delivery regions will be described. Referring now to FIG. 3, a first exemplary prostate resection device 110 constructed in accordance with the principles of the present invention comprises a shaft 112 having a proximal end 114 and a distal end 116. A plurality of nozzles 118 are mounted on the shaft 112 at a location spaced proximally from the distal end 116 by distance in the range from 1 cm to 5 cm. The nozzles, which are typically ceramic cores capable of generating a plasma or ports capable of directing a radially outward stream of electrically conductive fluid, may be mounted on structure 120, which allows the nozzles 118 to be moved radially outwardly, as shown in broken line in FIG. 3. An anchor 122, shown as an inflatable balloon is mounted on the distal end 116 of the shaft 112 at a location between the nozzles 118 and the distal tip 124. The expandable structure 122 will be capable of being expanded within the bladder to anchor the shaft 112 so that the nozzle array 118 lies within the prostate, as described in more detail below. The shaft 112 will include lumens, passages, electrically conductive wires, and the like, in order to deliver energy and materials from the proximal end 114 to the distal end 116 of the shaft. For example, an RF energy source 126 will be connected to the shaft 112, usually to the nozzles 118, in order to deliver RF energy to an electrically conductive fluid delivered from source 128 to the nozzles 118, typically through a lumen within the shaft 112. Other lumens, channels, or conduits will be provided in order to allow aspiration to a vacuum source 130 which is typically connected to one or more aspiration ports 132. Other conduits may be provided within the shaft 112 in order to permit introduction of a flushing fluid, such as saline, from a source 134 to ports 136. In other instances, it will be possible to connect the aspiration and flushing sources 130 and 134 to a common port so that aspiration and flushing may be conducted sequentially rather than simultaneously. Further optionally, internal lumens, conduits, or the like, may be provided in order to connect a source of insufflation 140 to one or more insufflation ports 142 on the shaft in the region of the array 118. Finally, internal lumens, conduits, or the like, may be provided for connecting balloon 122 to a balloon inflation source 144.

Figure 4:
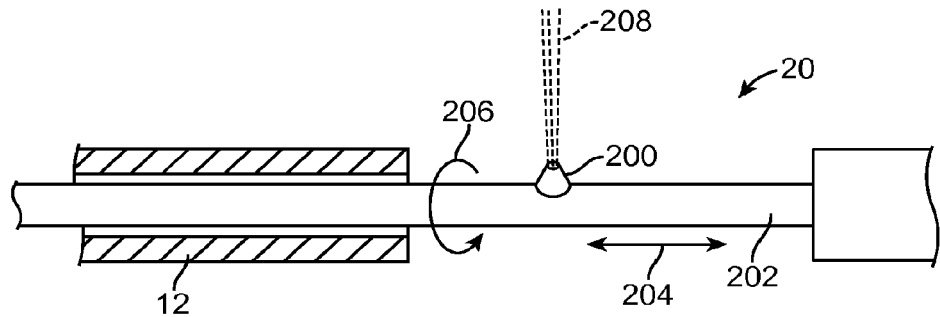
FIG. 4 illustrates an energy source suitable for use in the devices of the present invention, wherein the energy source delivers a fluid stream for tissue resection.

As shown in FIG. 4, an exemplary energy delivery region 20 can be formed by a high pressure nozzle 200 which is carried on a delivery tube 202 which is disposed within the shaft 12. Carrier tube 202 may be axially translated as shown by arrow 204 and/or rotated as shown by arrow 206 so that the fluid stream 208 emanating from the nozzle 200 can be scanned or rastered over all or a selected portion of the urethra within the prostate. Specific pressures and other details for such high pressure water treatment are described, for example, in Jian and Jiajun, supra.

Figure 5:
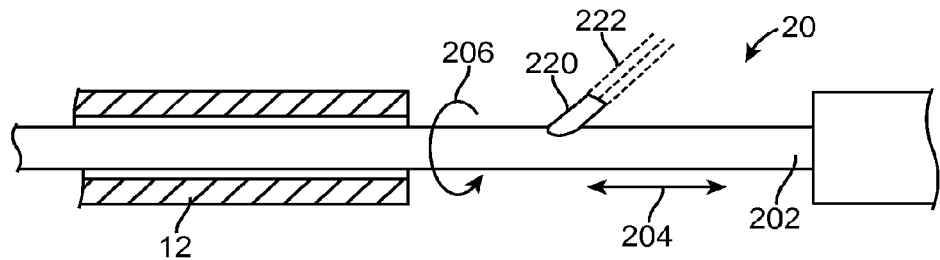
FIG. 5 illustrates an energy source suitable for use in devices of the present invention, wherein the energy source comprises a deflected optical waveguide for delivering laser energy to the prostatic tissue.

Referring now to FIG. 5, the energy source within the energy delivery region 20 may comprise a fiber-optic waveguide or fiber bundle 220 carried on the rotating and translating shaft 202. The optical waveguide 220 transmits laser or other coherent optical energy in a beam 222 which may be scanned or rastered over the urethral wall and prostatic tissue by rotating and/or translating the carrier tube 202.

Figure 6:
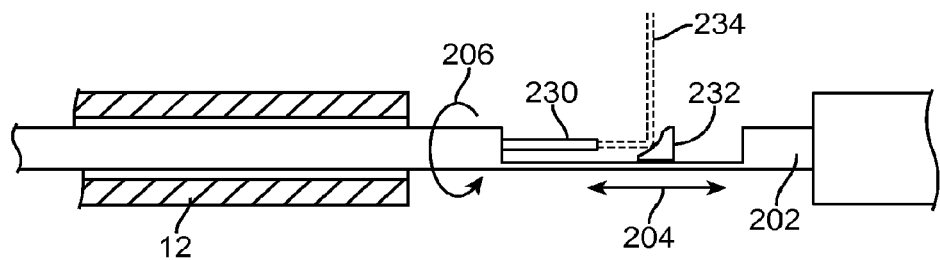
FIG. 6 illustrates a device similar to that shown in FIG. 5, except the optical waveguide directs laser energy at a mirror which laterally deflects the laser energy.

As shown in FIG. 6, laser energy from an optical waveguide or fiber bundle 230 may be directed axially against a mirror 232, where the waveguide and mirror are both carried on the rotating and axially translating carrier tube 202. Again, by rotating and/or translating the carrier tube 202, the emanating beam 234 can be scanned or rastered over the urethral wall.

Figure 7:
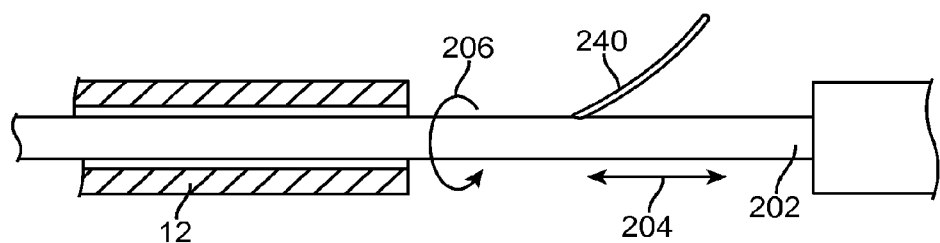
FIG. 7 illustrates an energy source suitable for use in the devices of the present invention, wherein the energy source comprises a laterally projecting electrode which can engage the urethral wall and prostatic tissue to deliver radiofrequency energy for tissue ablation.

Referring now to FIG. 7, in yet another embodiment, the rotating and axially translating tube 202 may carry an electrode 240 which projects laterally from the tube. The electrode 240 will be adapted for connection to a radiofrequency energy source so that, when the electrode contacts the urethral wall and prostatic tissue, radiofrequency energy can be delivered, either in a monopolar or bipolar mode. The radiofrequency energy can thus ablate the tissue over selected volumes and regions of the prostatic tissue. Optionally, by changing the nature of the radio frequency energy, the electrode 240 could also be used to cauterize the tissue after it has been treated.

In one embodiment of the present invention, the device is configured to selectively resect tissue, causing the removal of some tissue compositions while leaving other tissue compositions intact. For example, the prostate and nearby regions comprise a variety of tissue compositions, including glandular prostate tissue, intra-prostate vessels, fibromuscular stroma, capsular tissue, sphincter muscles, seminal vesicles, etc. When treating BPH or other prostate conditions, it is desirable to remove glandular prostate tissue and leave other tissues, such as vessels and capsular tissue, substantially undamaged.

As referred to herein, the term resection is meant to include any removal of tissue, including removal of one or more conglomerates of tissue cells, removal of fractions of tissue cells, etc.

One advantage of treating BPH by selective tissue resection is the reduced need (or no need) for cauterization, since there is little or no damage to intra-prostate blood vessels and as a result there is limited bleeding. Another advantage is a decreased chance of incontinence or impotence, since selective resection decreases the risk of perforating or otherwise damaging surrounding tissues, such as the prostate capsule, sphincter muscles, seminal vesicles, etc.

When using a fluid stream to resect tissue, selective tissue resection may be accomplished by varying one or more parameters of the fluid stream, such as the pressure within a nozzle or other fluid delivery element, or the flow rate of the fluid in the stream, so that it resects some tissue compositions while leaving other tissue compositions substantially undamaged.

In one embodiment, the fluid stream parameters may be configured to leave non-target tissues substantially undamaged even when those tissues are exposed to the fluid stream for an extended period of time, i.e., typically a period of time that is sufficient to achieve the desired resection. In another embodiment, the fluid stream parameters may be configured to resect the target tissue at a substantially higher rate than the non-target tissue, thereby limiting damage to non-target tissue. Such parameters may be adjusted, depending on the target tissue that is to be selectively resected.

In one embodiment, the rate of resection is configured to be higher for glandular tissue than for non-glandular tissue. The rate of resection may be configured by altering the pressure of the fluid, or by adjusting other fluid parameters, as described above. In particular, the rate of resection for glandular tissue may be configured to be significantly higher than that for non-glandular tissue, such that during the treatment period non-glandular tissue remains effectively undamaged. For example, the rate of resection of glandular tissue may be configured to be at least twice as high as that for non-glandular tissue. As another example, the rate of resection for glandular tissue may be configured to be at least 10 times as high as that for non-glandular tissue.

It is noted that tissue resection has a critical pressure (which is a pressure below which tissue does not resect and above which tissue can be resected) because the removal process involves tearing of the tissue, wherein tissue is stretched on a micro scale to the point where the tissue matrix ruptures or tears. Since tissue is elastic, there will be a critical breaking point. Different types of tissue will have different critical breaking points, and hence different critical pressures associated with them.

Indeed, given a particular fluid delivery element size (such as nozzle diameter), each tissue type typically has a critical pressure of the fluid stream source (hereinafter also referred to as Pcrit) below which the rate of resection approaches zero, and above which the rate of resection generally increases monotonically, and possibly exponentially. Specifically, due to differences in tissue composition, the pressure of the fluid stream source may be configured to selectively resect a particular type of tissue while leaving other tissue types with higher critical pressures generally undamaged.

Figure 8:
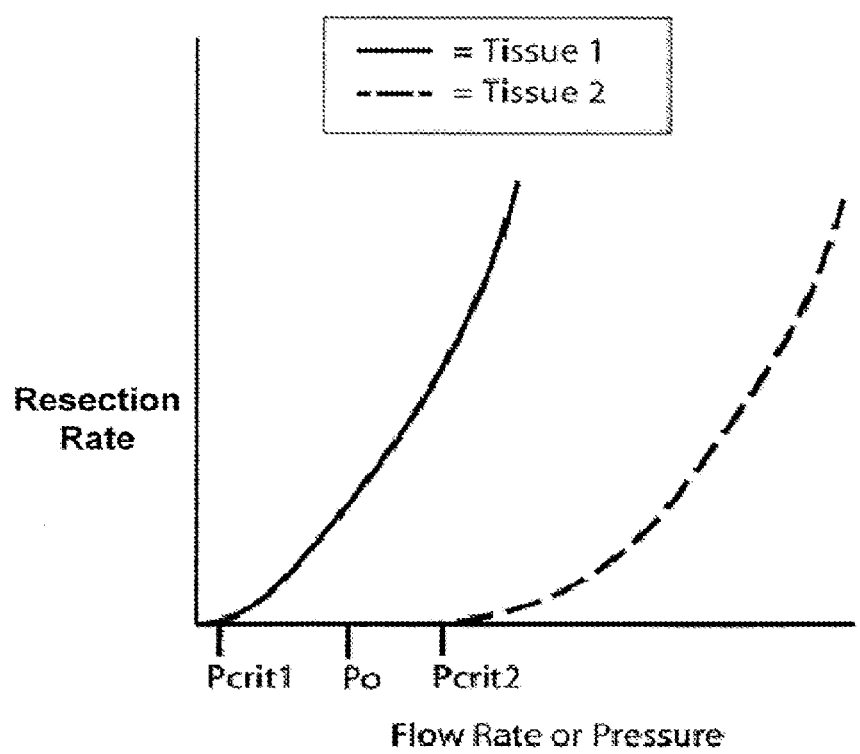
FIG. 8 is a graph of tissue resection rates demonstrating critical pressures.

An important aspect of resecting tissue in a multi-tissue environment according to the present embodiments is that it is possible to operate in a regime where one tissue type is resected and another tissue type remains substantially undamaged. This happens most strongly when operating at a pressure between the critical pressures of the two tissue types. As seen in FIG. 8, the operating pressure p0 of the fluid stream may be configured to be greater than the critical pressure of tissue 1 (p0>perit1) so that tissue 1 experiences a resection rate that is greater than zero, while keeping the pressure p0 less than the critical pressure of tissue 2 (p0<perit2) so that tissue 2 experiences a rate of resection that is substantially near zero. In such a configuration, the fluid stream is said to be configured to selectively resect tissue 1 but not tissue 2.

In one embodiment configured to treat BPH, the fluid stream source pressure is configured to be above the critical pressure of glandular prostate tissue but below the critical pressure of non-glandular prostate tissue. In such an embodiment, the pressure is sufficiently high to resect glandular tissue, but too low to substantially resect or damage non-glandular tissue such as intra-prostate blood vessels, fibromuscular stroma, capsular tissue, etc. In one embodiment, the fluid is pressurized to a pressure within the range of about 1-30,000 psi before leaving the fluid delivery element, more preferably to a pressure within the range of about 50-1,500 psi, and most preferably to a pressure within the range of about 100-1,000 psi.

The following example illustrates some tissue critical pressures for fluid stream resection. It is noted that the following configurations are provided as an example and should not be construed as limiting.

Example 1

Exemplary Critical Pressures of Different Kidney Tissue Compositions

Tissue critical pressures were measured in pig kidneys. Kidney tissue was chosen because its composition is similar to that of the prostate tissue. A columnar fluid stream of approximately 200 microns in diameter was used for tissue resection. The glandular tissue (the pink outer portion of the kidney) is very soft, and easily tears with finger pressure, while the inside of the kidney comprises tougher vascular tissue. The critical pressure for the glandular tissue with this fluid stream was found to be about 80 psi, and about 500 psi for the vascular tissue, as seen in Table 1 below.

Table 1 of Different critical pressures of glandular and vascular tissues in pig kidney.

| Tissue | $P_{crit}$ (psi) |
|---|---|
| Glandular | 80 |
| Vascular | 500 |

For example, experiments show that when resecting pig kidney using a nozzle of approximately 200 microns in diameter with liquid source pressure of about 500 psi, the rate of resection over a 10 cm area is about 1 cm per 30 sec for glandular tissue (i.e., removal of 10 cc per 30 sec), and less than about 0.1 cm per 180 sec for vascular tissue, which is about a sixty-fold difference in resection rates. Thus, within the same resection time period, more glandular tissue will be resected than vascular tissue. Thereby, the resection time period can be configured to allow resection of glandular tissue without substantial damage to vascular tissue. The rate of resection may be adjusted by varying the fluid source pressure and/or the size of the nozzle. For example, the rate of resection for glandular tissue may be adjusted to about 1 cc per min, 5 cc per min, 10 cc per min, 30 cc per min, or other rates. As noted above, it is understood herein that varying the size of the nozzle may necessitate varying the fluid source pressure in order to cause the fluid stream to impinge with sufficient force upon tissue to achieve desired resection rates.

Figure 9A:
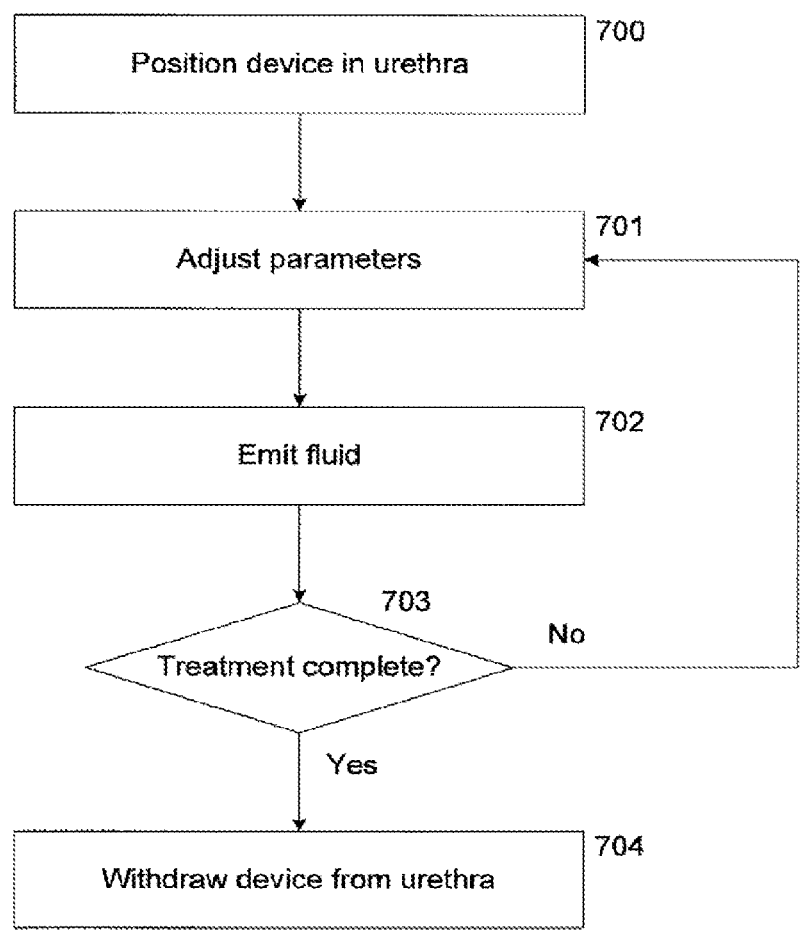
FIG. 9a is a flow diagram illustrating selective and controlled resection.

FIG. 9a is a flow diagram illustrating a method for selective prostate resection, according to one embodiment. At step 700, the device is positioned and anchored in the urethra, as described above. At step 701, various fluid parameters such as the pressure of the fluid source, shape of the fluid stream, etc., are configured to resect a specific tissue type, such as glandular prostate tissue. By configuring the fluid parameters one can control fluid force, rate of resection, treatment time, area of tissue to be resected, etc., in order to achieve controlled and selective resection. After the parameters are configured, at step 702, the device is configured to discharge a fluid stream to resect the target tissue. At step 703, if it is determined that the treatment is complete, the device is withdrawn from the urethra U at step 704.

However, if at step 703 it is determined that the treatment is not yet complete, then the fluid parameters may be re-configured as needed, as described in step 701, and the cycle of steps repeats until treatment is complete. In particular, re-configuration of the fluid parameters is advantageous in an embodiment where it is desired to resect two different types of tissues for a complete treatment. In such an embodiment, the fluid parameters may be adjusted to take into account the change in the type of target tissue that is to be resected.

Typically, after some or all of the glandular tissue has been resected, other tissue types such as vascular or capsular tissue will be exposed to the fluid stream. While the fluid stream parameters are configured to selectively resect glandular tissue, it is also contemplated that the fluid parameters may be dynamically adjusted during the resection procedure to take into account the gradual exposure of non-glandular tissue and to fine-tune the resection selectivity as needed. After the fluid parameters are thusly re-configured at step 701, then at step 702 the re-configured fluid stream is emitted to continue tissue resection, and the operation continues until the treatment is complete.

Specifically, it is noted that when treating the prostate from within the urethra, the urethral wall is interposed between the source of the fluid stream (such as a nozzle or other fluid delivery element) and the target glandular prostate tissue that is to be resected.

Therefore, in one embodiment, the fluid stream parameters are initially configured to resect and penetrate a portion of urethral tissue (e.g., the urethral wall). However, since the composition of glandular prostate tissue is weaker than that of the urethral tissue, it is desirable to avoid resecting glandular tissue with the same fluid stream force as that used to resect the urethral wall. To accomplish this, the fluid stream may be used for a period of time that is sufficient to resect and penetrate the urethral wall, and not longer. Thereafter, a fluid stream of reduced strength may be used to resect glandular prostate tissue.

Figure 9B:
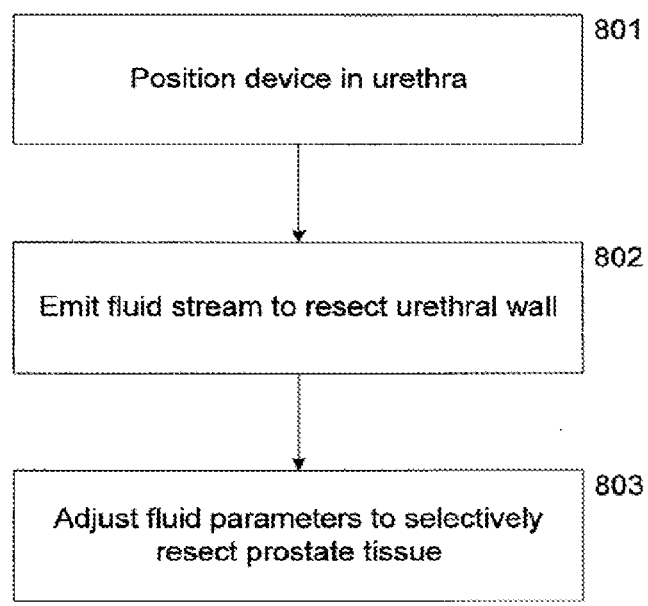
FIG. 9b is a flow diagram illustrating selective resection, wherein the fluid stream is configured to penetrate the urethral wall before resecting the prostate tissue.

FIG. 9b is a flow diagram illustrating a method for selective prostate resection, wherein the fluid stream is configured to first penetrate and resect the urethral wall, according to one embodiment. At step 801, the device is positioned and anchored in the urethra, as described above. At step 802, the device is configured to discharge a fluid stream of sufficient force to resect and penetrate the urethral wall. At step 803, after the fluid stream has penetrated the urethral wall, the fluid stream is adjusted to a level that selectively resects the desired prostate tissue while leaving intra-pro state blood vessels, capsules, and other non-glandular tissue substantially undamaged.

In addition, it is contemplated that the shape of the fluid stream also affects selective resection. While the fluid stream is exemplarily shown in FIG. 10a as a columnar fluid stream 333 or diverging fluid stream 334, it is contemplated that the fluid stream may be of any shape or configuration that allows resection according to the present embodiments. In particular, there are numerous advantages to both the columnar fluid stream configuration and the diverging fluid stream configuration, as will be described further below.

In a columnar fluid stream configuration 333, the device emits the fluid stream as a substantially focused rod-like fluid column that has a substantially zero divergence angle. In one embodiment, the columnar fluid stream is configured as a generally straight or non-diverging fluid stream. In such configuration, the device emits the fluid stream substantially as a cylinder or other non-diverging shape, thereby transmitting energy to the tissue over an area or spot size that is largely independent of the tissue distance from the fluid delivery element. Optionally, the fluid stream may be adjusted to converge, for example if the fluid delivery element comprises multiple nozzles or if the fluid contains bubbles, in order to focus the energy delivered to tissue.

Figure 10A:
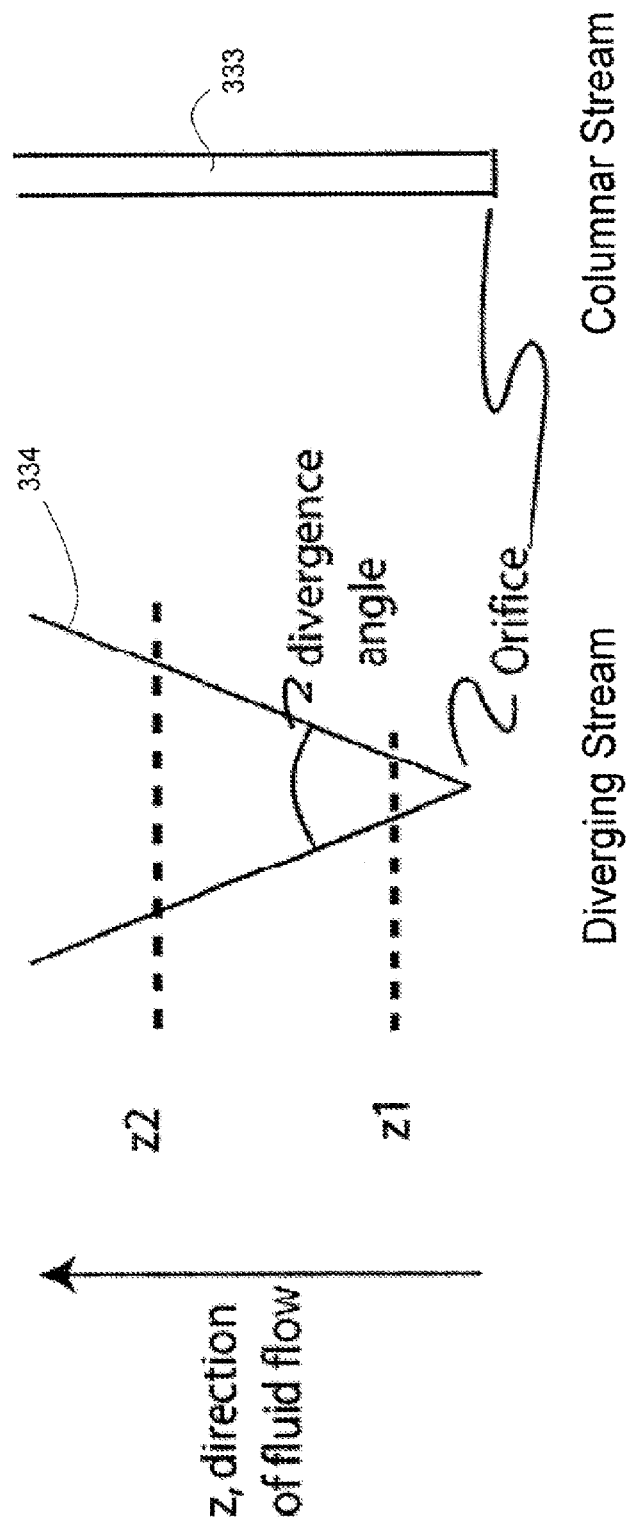
FIG. 10a illustrates a columnar fluid stream and a diverging fluid stream.
Figure 10B:
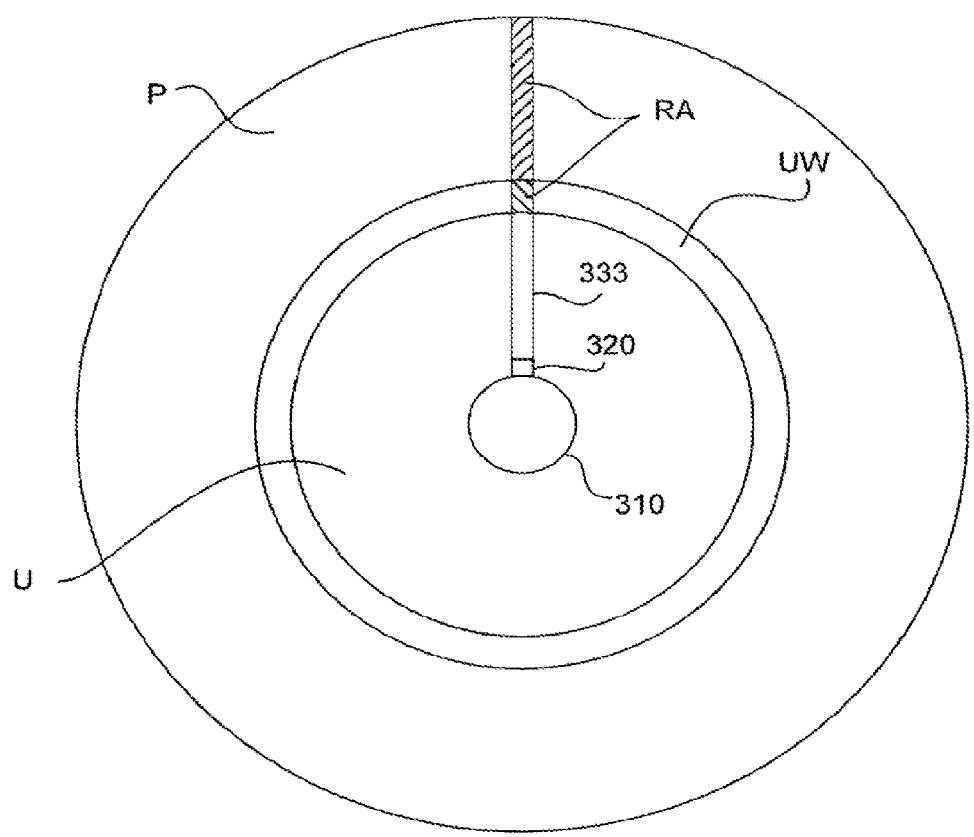
FIG. 10b illustrates a cross-sectional view of a tissue modification device configured to emit a columnar fluid stream.

FIG. 10b shows a cross-sectional view of the device emitting a columnar fluid stream to modify a tissue such as the prostate. An elongate element 310 (such as a shaft, as described above) of the device is disposed within the urethra U. A fluid delivery element 320 disposed on the carrier tube (not shown) within the elongate element 310 is configured to emit a columnar fluid stream 333. As understood herein, the fluid delivery element 320 may comprise a nozzle, as described above, or any other element configured to emit fluid. The columnar fluid stream 333 is configured to resect tissue, such as the urethral wall UW and the prostate tissue P, within a resection area RA.

One characteristic of the columnar fluid stream configuration is that the resection area RA remains substantially constant for some distance from the fluid delivery element 320, since the width of the resection area RA is substantially independent of the fluid distance from the fluid delivery element 320. This is advantageous because the resection area RA remains focused and constant as the fluid stream 333 travels away from the fluid delivery element 320, thereby transmitting energy to the tissue at a focal area. The concentration of energy within a focused resection area RA is particularly advantageous when resecting or penetrating tough tissue, such as the urethral wall UW. In one embodiment, the columnarity of the fluid stream may be varied by introducing pressure fluctuations in the fluid delivery. For example, the columnarity of the fluid stream may be varied by mechanically and controllably introducing a generally solid object in the fluid delivery path, such as behind an aperture of the fluid delivery element 320 or in the path of the fluid stream after it exits an aperture of the fluid delivery element 320. In another example, the columnarity of the fluid stream may be varied by introducing a vibrating element in the fluid pathway, such as a piezoelectric element or the like, to create pressure fluctuations.

In another embodiment, the fluid stream is configured as a diverging fluid stream 334, as seen in FIG. 10a. A diverging fluid stream 334 is one in which the fluid exits a fluid stream source, such as the fluid delivery element 320, and diverges substantially in a cone, wherein the tip of the cone is at the fluid stream source. The rate of resection of a diverging fluid stream 334 can be represented as a function of the distance z from the fluid emitting fluid delivery element 320 to the tissue that is to be resected. As shown in FIG. 10a, z2 is further away from the orifice than z1, and accordingly the rate of resection at z1 is higher than the rate of resection at z2.

The diverging fluid stream 334 may be characterized by the angle of divergence of the fluid stream. In one embodiment, the angle of divergence is configured to be about 0-90 degrees, more preferably about 2-45 degrees, more preferably about 4-20 degrees, and most preferably about 7 degrees, while it is also contemplated that the angle of divergence may be varied as needed.

Additionally, the diverging fluid stream 334 may be characterized by the cross-sectional shape of the fluid stream. Generally, the diverging fluid stream 334 has a cross-sectional area, or spot-size, that increases at distances further from the fluid stream source (e.g., fluid delivery element 320), thereby proportionally reducing the force of the fluid stream per unit area. This increase of spot-size generally results in greater resection rates of tissue closer to the fluid stream source.

In one embodiment, the cross-sectional shape of the diverging fluid stream 334 is configured as a generally narrow rectangle (for a fan-shaped fluid stream). In another embodiment, the cross-sectional shape of the diverging fluid stream 334 is configured as generally a circle (for a conical-shaped fluid stream), wherein the smallest cross-sectional area is at the fluid stream source. It is noted that the cross-sectional shape of the diverging fluid stream 334 may be configured as any shape that encloses a non-zero area (e.g., an ellipse, or an irregular shape).

Figure 10C:
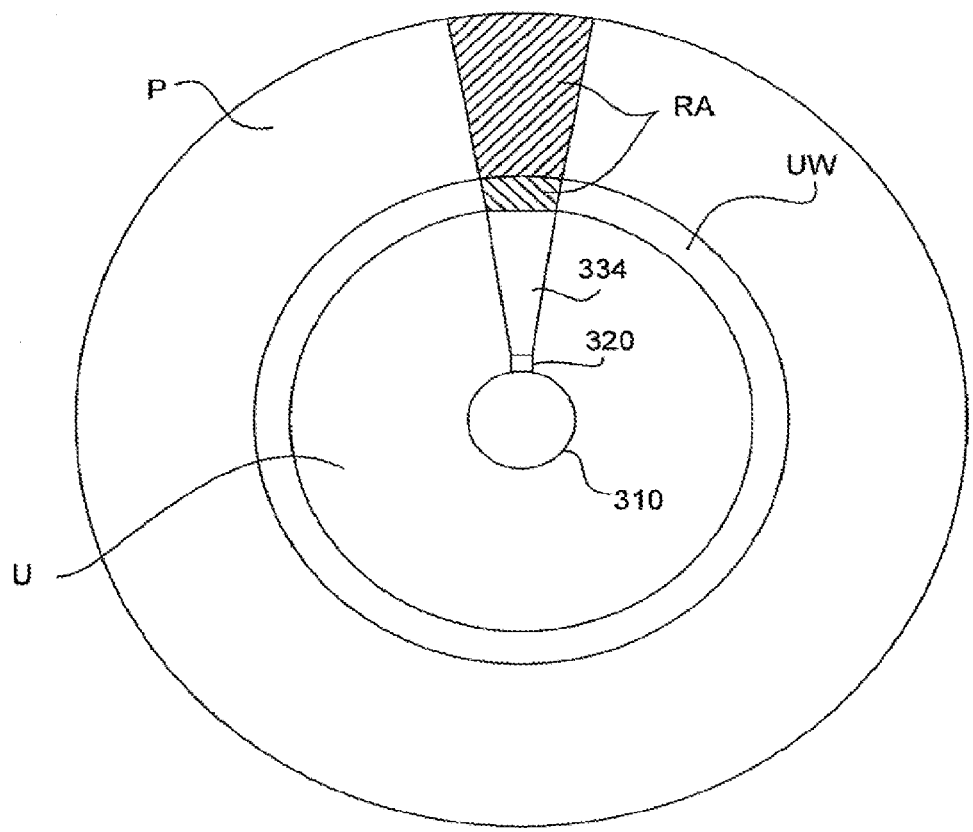
FIG. 10c illustrates a cross-sectional view of a tissue modification device configured to emit a diverging fluid stream.

FIG. 10c shows a cross-sectional view of the device emitting a diverging fluid stream to modify tissue such as the prostate. An elongate element 310 of the device is disposed within the urethra U. A fluid delivery element 320 disposed on the carrier tube (not shown) within the elongate element 310 is configured to emit a diverging fluid stream 334. The diverging fluid stream 334 is configured to resect tissue such as the urethral wall UW and the prostate tissue P within a resection area RA. The resection area RA covered by the diverging fluid stream 334 increases as the fluid stream travels away from the fluid delivery element 320, thereby proportionally reducing the strength of the fluid stream per unit area.

A characteristic of the diverging fluid stream 334 is that the resection width increases as a function of distance from the fluid delivery element 320, while the rate of resection per unit area decreases as a function of distance from the fluid delivery element 320. This is because the total energy delivered in the fluid stream is generally constant (not taking into account any decrease in fluid speed), yet the energy is delivered over a larger area. Thus, the energy delivered per area decreases, which is a key parameter upon which the rate of resection depends. Therefore, the rate of resection per unit area decreases as a function of distance.

Furthermore, in a diverging fluid stream 334 the volumetric rate of resection may be substantially constant as a function of distance. That is, while the rate of resection per unit area decreases, the total area resected increases proportionately, and hence the total resected volume remains substantially constant. It is noted that if the areal rate of resection as a function of areal energy density is non-linear and monotonically increasing with energy, then the volumetric rate of resection will decrease as function of distance from the fluid delivery element 320. It is further noted that any slowing of the fluid stream particles (for example, liquid droplets) will also decrease the volumetric resection rate as a function of distance.

Figure 11:
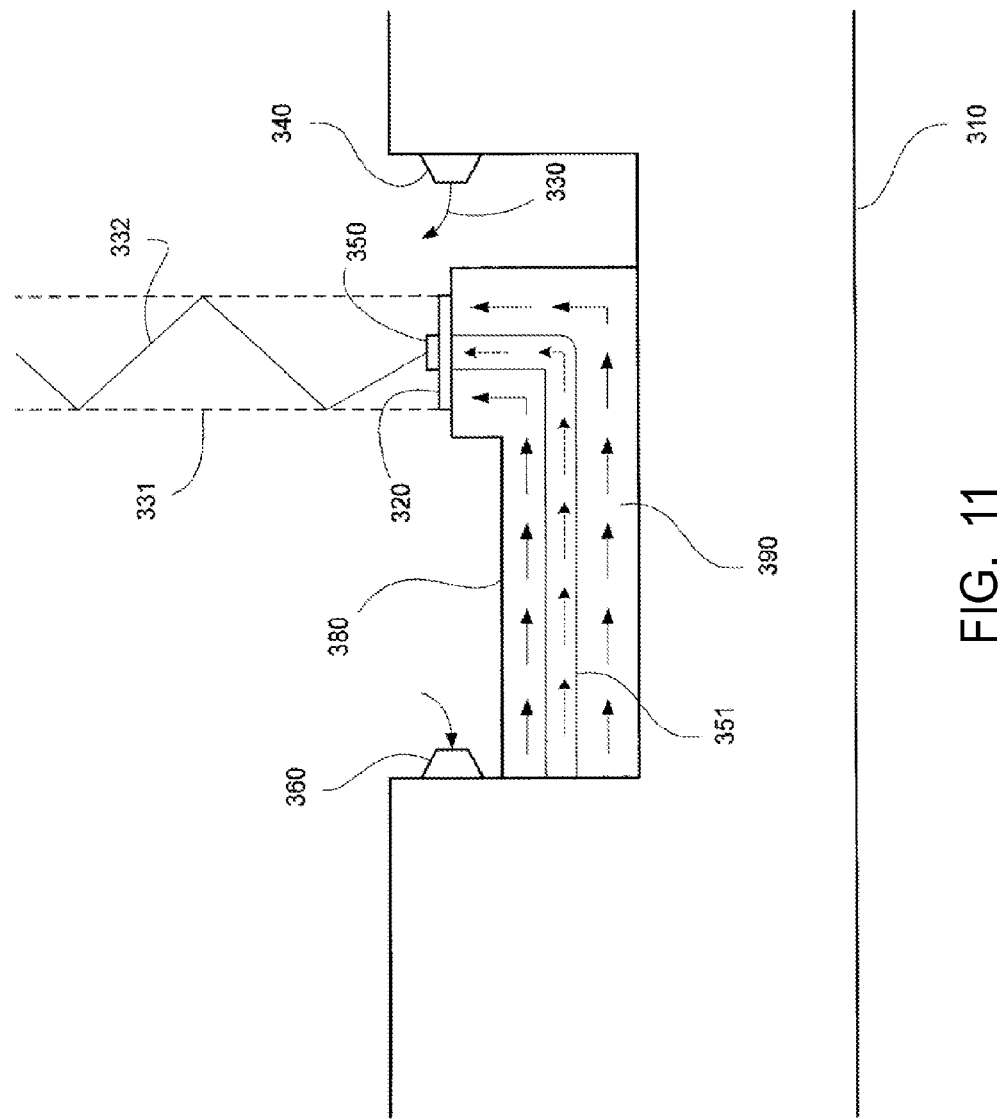
FIG. 11 illustrates a tissue modification device that uses a fluid stream for tissue resection, wherein the fluid stream may optionally act as a conduit for electromagnetic energy.

Referring now to FIG. 11, the device comprises an elongate element 310, such as a shaft, configured to be inserted into a body region. The elongate element 310 comprises a window exposing a carrier tube 380 and other components described below. The window reveals a carrier tube 380 and a high pressure fluid delivery element 320 disposed on the carrier tube 380. The fluid delivery element 320 is connected to a fluid source (not shown) via a fluid lumen 390 which delivers fluid from the source to the fluid delivery element 320.

Optionally, when the elongate element 310 is introduced through the urethra, the elongate element 310 may be covered by a sheath or other cover (not shown). When fully covered with the sheath, the window is protected so that it reduces scraping and injury to the urethra as the elongate element 310 is advanced. Once in place, the sheath is retracted, exposing the window. The carrier tube 380 may then be rotated and advanced and/or retracted so that the fluid is delivered through the fluid delivery element 320.

Additionally and optionally, the device may comprise a shield element (not shown) that is positioned to substantially cover the fluid delivery element 320 while maintaining a space between the fluid delivery element 320 and the shield element. This in return effectively maintains that space between the fluid delivery element 320 and any tissue that might impinge on the shield element. In one embodiment, the shield element is a substantially flat sheet-like element positioned over the fluid delivery element 320. The shield element is positioned or shaped such that it allows the carrier tube 380 to move within the elongate element 310 as needed. For example, the shield element may be curved to follow a curvature of the carrier tube 380. The shield element comprises an opening to allow the fluid stream emitted by the fluid delivery element 320 to travel unobstructed through the opening and impinge on the tissue. The opening may be circular, or it may comprise other shapes. One advantage of such a shield element is that it protects the fluid delivery element 320 from being damaged during insertion or removal procedures and/or during treatment. Another advantage of the shield element is that, during or after fluid emission, fluids that are returning back towards the fluid delivery element 320 may travel through the shield element opening (or through other paths around the shield element) and into the space between the shield element and the fluid delivery element 320. Such returned fluids may then be channeled out of that space such that fluid emission is not obstructed or hindered by such returned fluids.

The shield element may further be configured such that the space between the shield element and the fluid delivery element 320 is in continuous communication with a waste disposal lumen via a low-flow-resistance fluid path. This creates a low-flow-resistance path between the fluid delivery element 320 and an external destination of such waste, such that waste and fluids leaving the fluid delivery element 320 may easily leave the region surrounding the fluid delivery element 320. Low resistance in this case is understood to mean a flow resistance that is lower in comparison with a flow resistance of the fluid delivery element 320. This configuration advantageously prevents back-pressure at the fluid delivery element 320, which would otherwise reduce flow, and thereby allows the fluid stream emitted by the fluid delivery element 320 to travel substantially undisturbed by waste and return fluids.

The fluid delivery element 320 may be a single nozzle, a plurality of nozzles, or an array of nozzles of various configurations. The fluid delivery element 320 is configured to emit a fluid radially outwardly as a fluid stream 331, with sufficient force so that upon contact with the tissue the fluid stream 331 resects the tissue. The fluid stream 331 may be perpendicular to the elongate element 310, or it may be configured to be at various angles relative to the elongate element 310.

The carrier tube 380 may be axially translated, rotated, oscillated, or rotationally oscillated relative to the elongate element 310 so that the fluid stream 331 can be scanned or rastered to resect a desired area or volume of the tissue. The desired area or volume may be spherical, cylindrical, or any other predetermined area or volume of arbitrary shape and dimension.

Additionally and optionally, when the device is not being used to resect tissue, the carrier tube 380 may be positioned so that the fluid delivery element 320 and/or any other elements (such as visualization or cauterization elements) are positioned away from the window, thereby reducing the risk of damage to such elements, as well as reducing any risk of unintentional resection of the tissue.

The device further comprises at least one insufflation port 340 disposed on the elongate element 310. The insufflation port 340 is connected via one or more lumens to an insufflation source (not shown), wherein the insufflation source delivers a fluid 330 into the body region through the insufflation port 340 in order to expand the surrounding tissue and create a working space. The device further comprises at least one removal port 360 for the removal of debris products, such as resection products, resection fluid, other waste products, or a mixture thereof. The elongate element 310 may include lumens, passages, electrically conductive wires, and the like, configured to deliver energy and/or materials from the proximal end to the distal end of the elongate element 310 and/or to remove debris and waste products, details of which are described above.

Optionally, in addition to the fluid delivery element 320, the device may comprise an electromagnetic energy delivery port 350 disposed on the carrier tube 380 and positioned near or within the fluid delivery element 320. Electromagnetic energy 332 is delivered to the energy delivery port 350 by means of one or more conduits 351, such as optical fibers or other waveguides within the carrier tube 380 and the elongate element 310, as also described in greater detail above. The electromagnetic energy 332 may be radiofrequency energy, coherent or non-coherent light, or any other modality of electromagnetic energy. The energy delivery port 350 is configured to deliver the energy 332 through the interior of the fluid stream 331 so that the electromagnetic energy 332 may resect the tissue in lieu of, or in combination with, the fluid resection.

Additionally and optionally, the various electromagnetic energy modalities described above may be configured to cauterize the tissue, in combination with tissue resection, or independently thereof. Since selective tissue resection as disclosed herein generally causes little or no damage to remaining tissue such as vascular tissue and therefore causes limited or no bleeding, such cauterization need only be used on a limited basis, if at all. It is contemplated that when electromagnetic energy is delivered to the tissue by the fluid stream 331 for cauterization, the fluid source pressure may be adjusted to be generally below the critical pressure for tissue resection such that no additional tissue is resected.

Alternatively or additionally, cauterization may be achieved using other means, for example using a cauterizing balloon and/or stent placed in contact with tissue using a catheter device, as described above.

Furthermore, the device may comprise optional deflective elements, for example positioned within the interior or the elongate element 310 and away from the window, configured to deflect fluid, emitted by the fluid delivery element 320, back towards the fluid delivery element 320, thereby removing any debris that may have accumulated on the fluid delivery element 320 and/or energy delivery port 350 during tissue resection. Furthermore, the fluid delivery element 320 in combination with the deflective elements may be configured to clean a part of, or substantially the entirety of, the fluid delivery element 320, any visualization or cauterization elements, and/or carrier tube 380. The deflective element may be configured to be substantially flat or concave. Alternatively the deflective element may be configured as any shape or design.

Additionally, the deflective element may act be configured as a protective element for the fluid delivery element. The fluid delivery element may be positioned at a specific location relative to the protective element that protects the prostate from unexpected fluid emissions and protects the fluid delivery element 320 from, for example, clogging or obstruction by tissue, especially during insertion and removal from the body.

The carrier tube 380 comprises a carrier. The carrier may optionally comprise a tubular structure. Although reference is made to a carrier tube 380 in accordance with embodiments, the carrier may comprise a substantially non-tubular cross-section, for example a rectangular cross section, extending along a substantial portion of the carrier as described herein. Therefore, it is to be understood that although the carrier tube shown and described in the drawings, the carrier may comprise a non-circular carrier in each of the drawings and supporting text as described herein.

Figure 12:
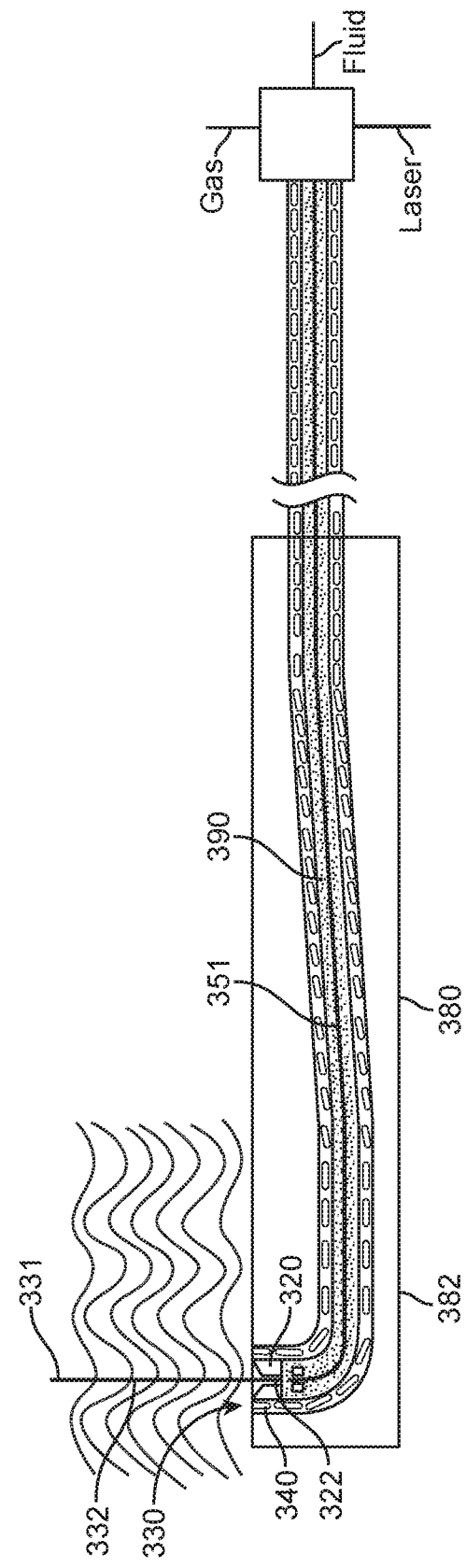
FIG. 12 shows a component of treatment probe 350 in accordance with embodiments.

FIG. 12 shows a component of treatment probe 350 in accordance with embodiments. A carrier tube 380 comprises a concentric configuration of a first fluid delivery port and a second fluid delivery port. Fluid delivery element 320 releases fluid stream 331. Fluid stream 331 defines an axis extending from the fluid delivery element 320 outward. The fluid stream 331 may comprise a diverging stream 334 or a columnar stream 333 as described herein. Fluid delivery element 320 comprises a nozzle 322. Nozzle 322 may comprise a substantially circular cross section. The nozzle 322 may comprise an internal channel having the circular cross section in which the internal channel extends cylindrically. The internal channel extends along an axis corresponding to the axis of the fluid stream 331.

Concentrically disposed around the fluid delivery element 320 is a port 340. The port 340 comprises a substantially annular channel extending circumferentially around fluid delivery element 320 and nozzle 322. Port 340 may comprise an insufflation port as described herein. Port 340 releases fluid 330 in a substantially concentric arrangement with fluid stream 331. The substantially concentric arrangement has the advantage of providing a protective jacket around fluid stream 331 with first fluid 330 extending outward from port 340 so as to beneficially direct the treatment stream toward the tissue. Energy conduit 351 extends from a source of energy such as a laser toward fluid delivery element 320. The energy conduit may comprise an optical fiber or a plurality of optical fibers coupled to a laser, for example. The optical fiber can extend toward nozzle 322 and can be concentrically aligned with the axis defined by nozzle 322 so as to provide efficient energy transmission of the light energy emitted from the optical fiber through the nozzle 322. A structure can be provided near the distal end of the optical fiber in order to align the optical fiber with the channel of nozzle 322. The concentric alignment of the optical fiber, the nozzle and the port 340 can provide therapeutic treatment of the patient that allows visualization and treatment of the patient. The fluid release from port 340 may comprise a liquid, for example saline, or a gas, for example CO2. The fluid delivered through port 340 can be user selectable with the interface as described herein.

The fluid stream 331 can provide an optical wave guide directed toward the tissue. In many embodiments the fluid stream 331 comprises an index of refraction greater than the fluid released through port 340. The wave guide media can be a liquid or gas and the jacketing media released from port 340 can be a liquid or gas. An intermediate media can be located between the probe and the target tissue. The intermediate media can be a liquid or gas, for example, one or more of saline, air or carbon dioxide. In many embodiments the intermediate media comprises a fluid release from nozzle 322 and a fluid release from annular port 340.

Figure 13A:
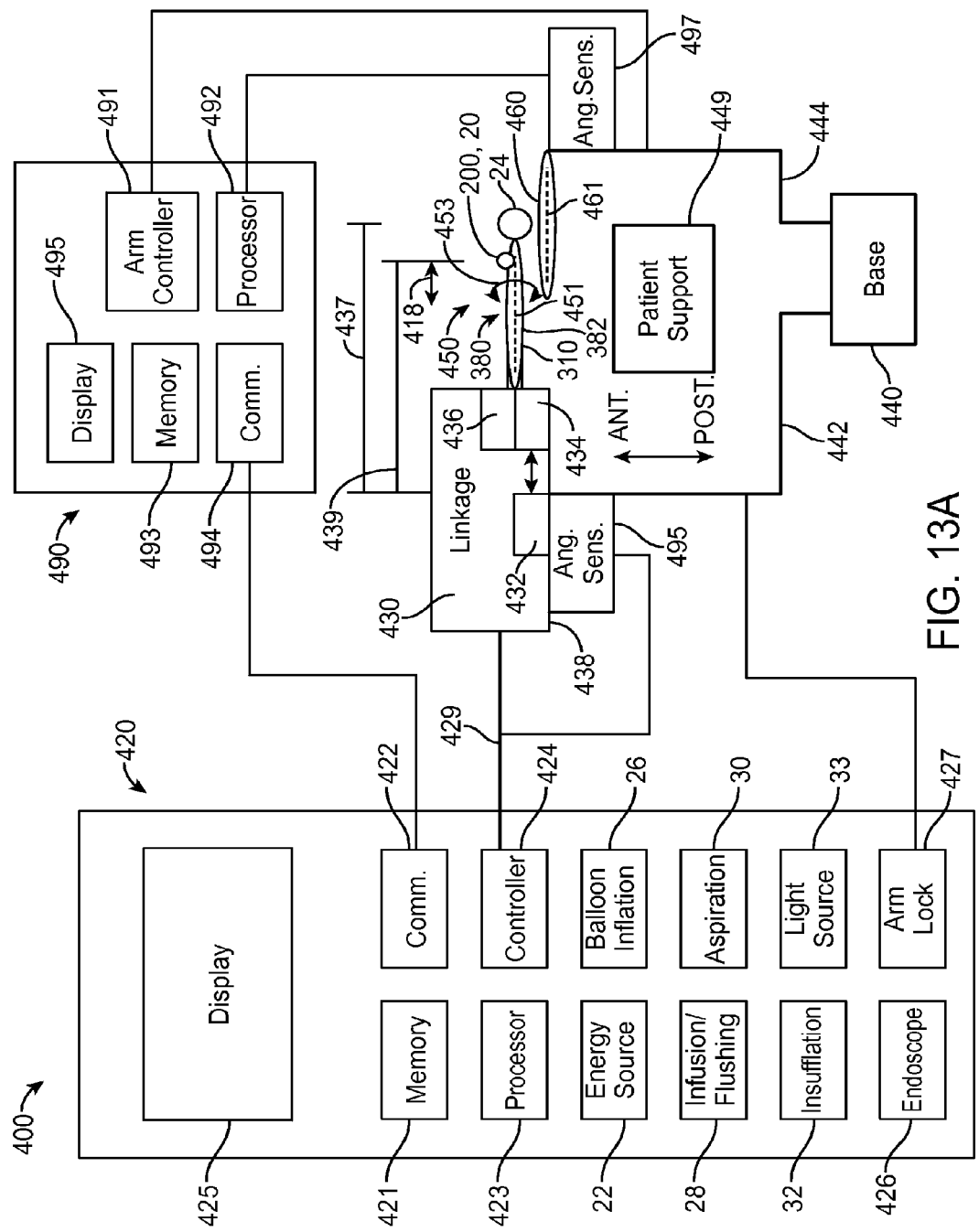
FIGS. 13A and 13B show a system that treat a patient in accordance with embodiments.
Figure 13B:
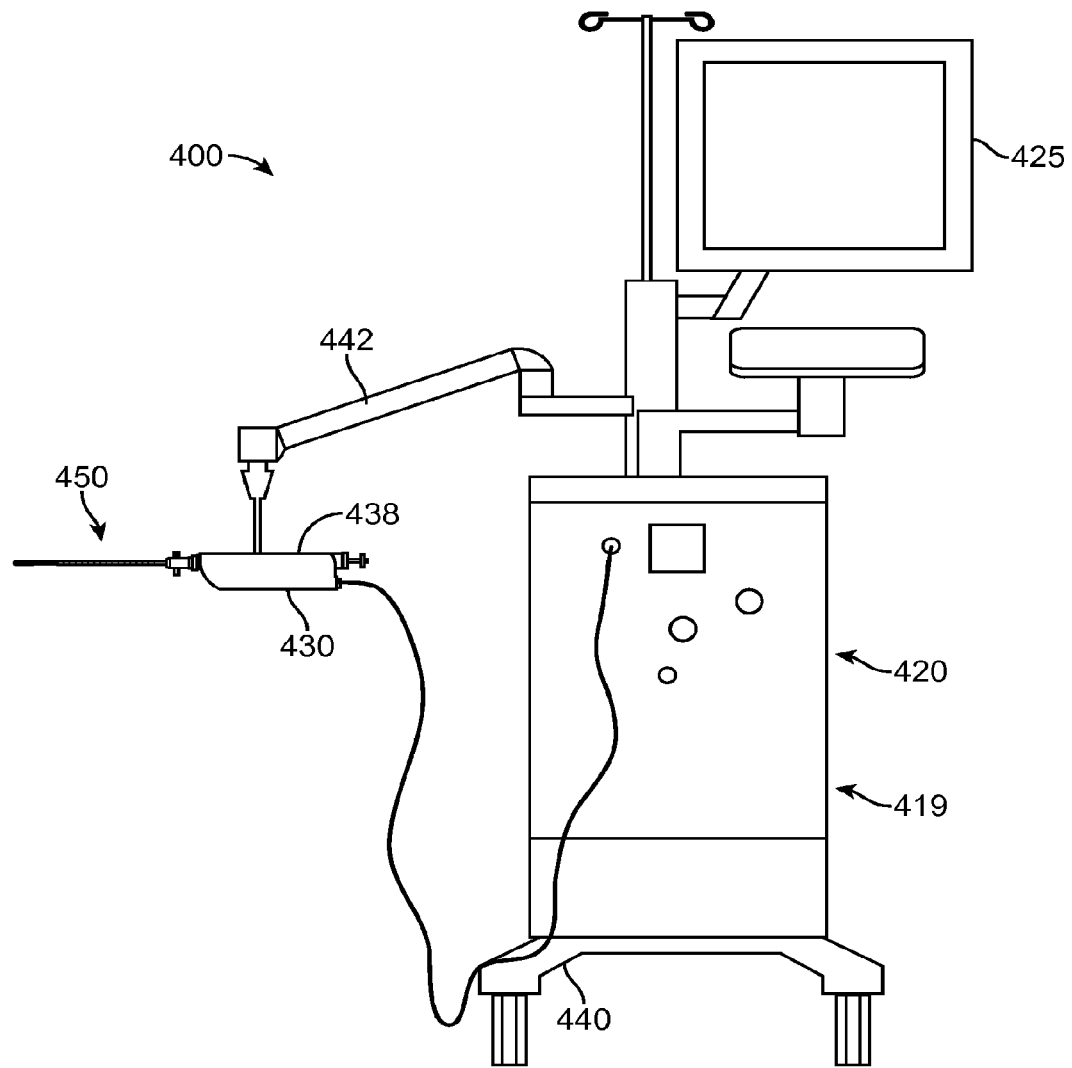

FIGS. 13A and 13B show a system that treat a patient in accordance with embodiments. The system 400 comprises a treatment probe 450 and may optionally comprise an imaging probe 460. The treatment probe 450 is coupled to a console 420 and a linkage 430. The imaging probe 460 is coupled to an imaging console 490. The patient treatment probe 450 and the imaging probe 460 can be coupled to a common base 440. The patient is supported with the patient support 449. The treatment probe 450 is coupled to the base 440 with an arm 442. The imaging probe 460 is coupled to the base 440 with an arm 444.

The patient is placed on the patient support 449, such that the treatment probe 450 and ultrasound probe 460 can be inserted into the patient. The patient can be placed in one or more of many positions such as prone, supine, upright, or inclined, for example. In many embodiments, the patient is placed in a lithotomy position, and stirrups may be used, for example. In many embodiments, the treatment probe 450 is inserted into the patient in a first direction on a first side of the patient, and the imaging probe is inserted into to the patient in a second direction on a second side of the patient. For example, the treatment probe can be inserted from an anterior side of the patient into a urethra of the patient, and the imaging probe can be inserted trans-rectally from a posterior side of the patient into the intestine of the patient. The treatment probe and imaging probe can be placed in the patient with one or more of urethral tissue, urethral wall tissue, prostate tissue, intestinal tissue, or intestinal wall tissue extending therebetween.

The treatment probe 450 and the imaging probe 460 can be inserted into the patient in one or more of many ways. During insertion, each arm may comprise a substantially unlocked configuration such the probe can be desirably rotated and translated in order to insert the probe into to the patient. When a probe has been inserted to a desired location, the arm can be locked. In the locked configuration, the probes can be oriented in relation to each other in one or more of many ways, such as parallel, skew, horizontal, oblique, or non-parallel, for example. It can be helpful to determine the orientation of the probes with angle sensors as described herein, in order to map the image date of the imaging probe to treatment probe coordinate references. Having the tissue image data mapped to treatment probe coordinate reference space can allow accurate targeting and treatment of tissue identified for treatment by an operator such as the physician.

In many embodiments, the treatment probe 450 is coupled to the imaging probe 460. In order to align the treatment with probe 450 based on images from imaging probe 460. The coupling can be achieved with the common base 440 as shown. Alternatively or in combination, the treatment probe and/or the imaging probe may comprise magnets to hold the probes in alignment through tissue of the patient. In many embodiments, the arm 442 is a movable and lockable arm such that the treatment probe 450 can be positioned in a desired location in a patient. When the probe 450 has been positioned in the desired location of the patient, the arm 442 can be locked with an arm lock 427. The imaging probe can be coupled to base 440 with arm 444, can be use to adjust the alignment of the probe when the treatment probe is locked in position. The arm 444 may comprise a lockable and movable probe under control of the imaging system or of the console and of the user interface, for example. The movable arm 444 may be micro-actuable so that the imaging probe 440 can be adjusted with small movements, for example a millimeter or so in relation to the treatment probe 450.

In many embodiments the treatment probe 450 and the imaging probe 460 are coupled to angle sensors so that the treatment can be controlled based on the alignment of the imaging probe 460 and the treatment probe 450. An angle sensor 495 is coupled to the imaging probe 450 with a support 438. An angle sensor 497 is coupled to the imaging probe 460. The angle sensors may comprise one or more of many types of angle sensors. For example, the angle sensors may comprise goniometers, accelerometers and combinations thereof. In many embodiments, angle sensor 495 comprises a 3-dimensional accelerometer to determine an orientation of the treatment probe 450 in three dimensions. In many embodiments, the angle sensor 497 comprises a 3-dimensional accelerometer to determine an orientation of the imaging probe 460 in three dimensions. Alternatively or in combination, the angle sensor 495 may comprise a goniometer to determine an angle of treatment probe 450 along an elongate axis of the treatment probe. Angle sensor 497 may comprise a goniometer to determine an angle of the imaging probe 460 along an elongate axis 461 of the imaging probe 460. The angle sensor 495 is coupled to a controller 424. The angle sensor 497 of the imaging probe is coupled to a processor 492 of the imaging system 490. Alternatively, the angle sensor 497 can be coupled to the controller 424 and also in combination.

The console 420 comprises a display 425 coupled to a processor system in components that are used to control treatment probe 450. The console 420 comprises a processor 423 having a memory 421. Communication circuitry 422 is coupled to processor 423 and controller 422. Communication circuitry 422 is coupled to the imaging system 490. The console 420 comprises components of an endoscope coupled to anchor 24. Infusion flushing control 28 is coupled to probe 450 to control infusion and flushing. Aspiration control 30 is coupled to probe 450 to control aspiration. Endoscope 426 can be components of console 420 and an endoscope insertable with probe 450 to treat the patient. Arm lock 427 of console 420 is coupled to arm 422 to lock the arm 422 or to allow the arm 422 to be freely movable to insert probe 450 into the patient. The console 420 comprises a light source 33.

The console 420 may comprise a pump 419 coupled to the carrier and nozzle as described herein.

The processor, controller and control electronics and circuitry can include one or more of many suitable components, such as one or more processor, one or more field-programmable gate array (FPGA), and one or more memory storage devices. In many embodiments, the control electronics controls the control panel of the graphic user interface (hereinafter "GUI") to provide for pre-procedure planning according to user specified treatment parameters as well as to provide user control over the surgery procedure.

The treatment probe 450 comprises an anchor 24. The anchor 24 anchors the distal end of the probe 450 while energy is delivered to energy delivery region 20 with the probe 450. The probe 450 may comprise a nozzle 200 as described herein. The probe 450 is coupled to the arm 422 with a linkage 430.

The linkage 430 comprises components to move energy delivery region 20 to a desired target location of the patient, for example, based on images of the patient. The linkage 430 comprises a first portion 432 and a second portion 434 and a third portion 436. The first portion 432 comprises a substantially fixed anchoring portion. The substantially fixed anchoring portion 432 is fixed to support 438. Support 438 may comprise a reference frame of linkage 430. Support 438 may comprise a rigid chassis or frame or housing to rigidly and stiffly couple arm 442 to treatment probe 450. The first portion 432 remains substantially fixed, while the second portion 434 and third portion 436 move to direct energy from the probe 450 to the patient. The first portion 432 is fixed to the substantially constant distance 438 to the anchor 434. The substantially fixed distance 438 between the anchor 24 and the fixed first portion 432 of the linkage allows the treatment to be accurately placed. The first portion 434 may comprise the linear actuator to accurately position the high pressure nozzle in treatment region 20 at a desired axial position along an elongate axis of probe 450.

The elongate axis of probe 450 generally extends between a proximal portion of probe 450 near linkage 430 to a distal end having anchor 24 attached thereto. The third portion 436 controls a rotation angle around the elongate axis. During treatment of the patient, a distance 439 between the treatment region 20 and the fixed portion of the linkage varies with a reference distance 439. The distance 439 adjusts in response to computer control to set a target location along the elongate axis of the treatment probe referenced to anchor 24. The first portion of the linkage remains fixed, while the second portion 434 adjust the position of the treatment region along the axis. The third portion of the linkage 436 adjusts the angle around the axis in response to controller 424 such that the distance along the axis at an angle of the treatment can be controlled very accurately with reference to anchor 24. The probe 450 may comprise a stiff member such as a spine extending between support 438 and anchor 24 such that the distance from linkage 430 to anchor 24 remains substantially constant during the treatment. The treatment probe 450 is coupled to treatment components as described herein to allow treatment with one or more forms of energy such as mechanical energy from a jet, electrical energy from electrodes or optical energy from a light source such as a laser source. The light source may comprise infrared, visible light or ultraviolet light. The energy delivery region 20 can be moved under control of linkage 430 such as to deliver an intended form of energy to a target tissue of the patient.

The imaging system 490, a memory 493, communication circuitry 494 and processor 492. The processor 492 in corresponding circuitry is coupled to the imaging probe 460. An arm controller 491 is coupled to arm 444 to precisely position imaging probe 460.

Figure 14A:
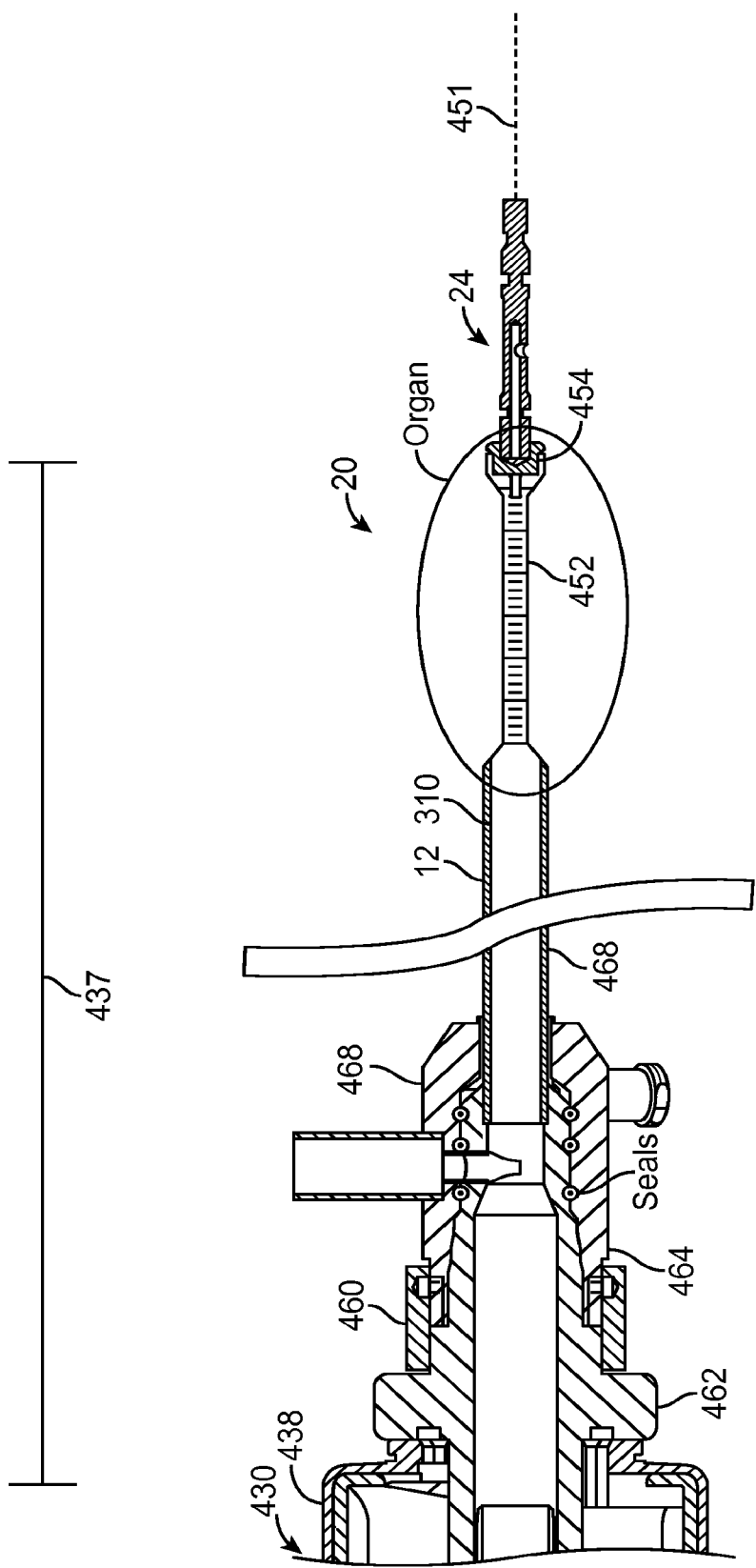
FIG. 14A shows a multipurpose sheath and manifold in accordance with embodiments.

FIG. 14A shows a multipurpose sheath and manifold in accordance with embodiments. A manifold 468 is configured to transmit a plurality of fluids to and from the working site. Manifold 468 is rigidly coupled, for example affixed, to the spine 452. A sheath 458 is located around spine 452 and can extend inward toward the manifold 468. The manifold 468 is coupled with a locking element 460 to support 438 in linkage 430. Manifold 468 can be decoupled from the linkage 430 and the support 438 so as to remove the linkage 430 and support 438 to permit additional components to be inserted into the working channel. For example, an endoscope can be inserted into the working channel to extend toward the working area of the organ, for example, the prostate. A structure 462 comprising a nose portion extends toward manifold 468. Structure 462 is shaped to engage manifold 468 and allow removal of structure 462, linkage 430 and support 438 when locking element 460 is disengaged. Manifold 468 comprises a structure 464 to engage in nose portion of structure 462. A plurality of seals are arranged on manifold 468 to allow removal of structure 462. When structure 462 has been removed an endoscope or other surgical tool can be inserted into the working space and advance toward the treatment site. For example an endoscope can be advanced toward the treatment site to be the treatment area. The manifold comprises a plurality of ports that are coupled to the treatment site to allow fluid to be transmitted and removed from the treatment site. For example when an endoscope has been placed at the treatment site. The locking element and manifold allow for removal of the linkage and treatment probes such that the manifold 468 remains coupled to sheath 458 and spine 452 within the patient.

In many embodiments treatment probes and carriers as described herein, for example tubular carriers, can be inserted and removed while the locking element 460 engages the linkage 430 and support 438. This configuration of the linkage, locking element and support allow probes to be rapidly and easily removed and reinserted to provide beneficial treatments.

The multipurpose sheath and manifold as described herein has the benefit of allowing the sheath, manifold, spine and anchor to remain attached to the patient while additional surgical tools are employed. The locking element interfaces with multiple instruments allowing for placement, visualization, and aquablation and aquabeam operations, without reintroduction or movement with respect to the tissue. Multiple sealed conduits allow for sheath ports to be used to transmit flow or pressure of varying fluids within or parallel to the working channel. The working channel may be used for visualization access to anatomy via existing rigid or flexible endoscope technology. The working channel has a large bore to accommodate many types of tools and allow for free flow of tissue and fluids. Alternate energy delivery devices may be used within the sheath or working channel as described herein.

In many embodiments the working channel is sized to allow a plurality of carriers within the working channel. For example, an endoscope carrier within the working channel and a treatment probe carrier as described herein within the working channel so as to allow visualization of the treatment site while the treatment probe performs aquablation and aqua beam operations as described herein.

Figure 14B:
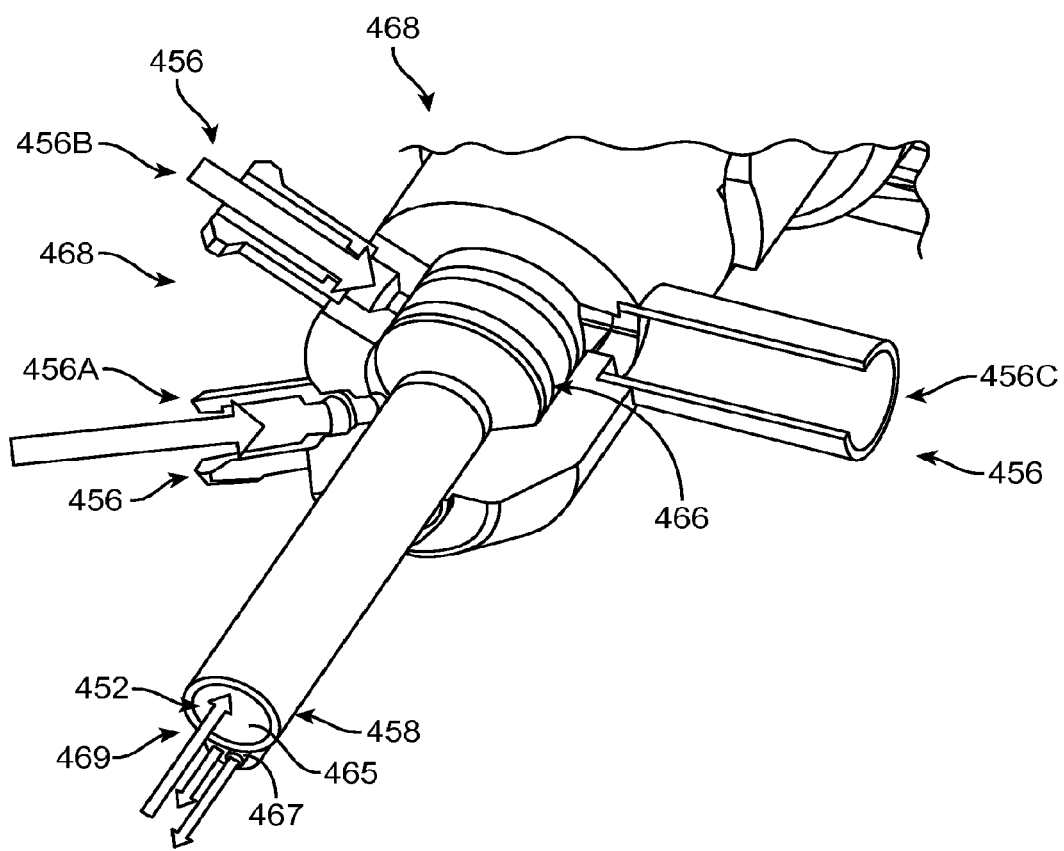
FIG. 14B shows manifold conduits of the manifold as in FIG. 14A configured for transmit and reception of multiple fluids while the manifold remains coupled to the patient in accordance with embodiments.

FIG. 14B shows manifold conduits of the manifold configured for transmitting and receiving multiple fluids while the manifold remains coupled to the patient. The manifold is coupled to a plurality of ports 456. The plurality of ports 456 may comprise an auxiliary fluid port 456A, a balloon pressure port 456B and a tissue removal port 456C. A sheath 458 extends circumferentially around spine 452. The spine 452 and sheath 458 can be rigidly coupled to the manifold portion and provide connections and channels coupled to the manifold portion. A channel 467, for example a tubular channel, is connected to port 456B to allow for inflation of the balloon. A channel 469 can be defined with sheath 458. Channel 469 can be coupled to port 456A to provide an auxiliary fluid to the treatment site. Port 456C to allow removal of tissue can be coupled to the main working channel 465. The main working channel 465 can extend from port 456C to the treatment site. A plurality of seals 466 are arranged to separate the treatment ports and channels as described herein. The manifold 468 can be decoupled from the linkage 430 and support 438 and allow balloon inflation pressure to be applied through port 456B. An auxiliary fluid can be provided through port 456A, for example, so as to flush the working channel 465. This configuration of the manifold allows the spine 452 and anchor 24 to remain in place when other instruments have been inserted into the working channel.

The plurality of manifold conduits as described herein allow tissue collection to be routed through the large bore working channel 469 to reduce flow obstructions. Balloon pressure can be transmitted from a lure fitting to the distal tip of the anchor with small diameter tubing, for example, tubing defining channel 467. An auxiliary fluid is transmitted between the sheath and spine to the treatment area with channel 469.

Figure 14C:
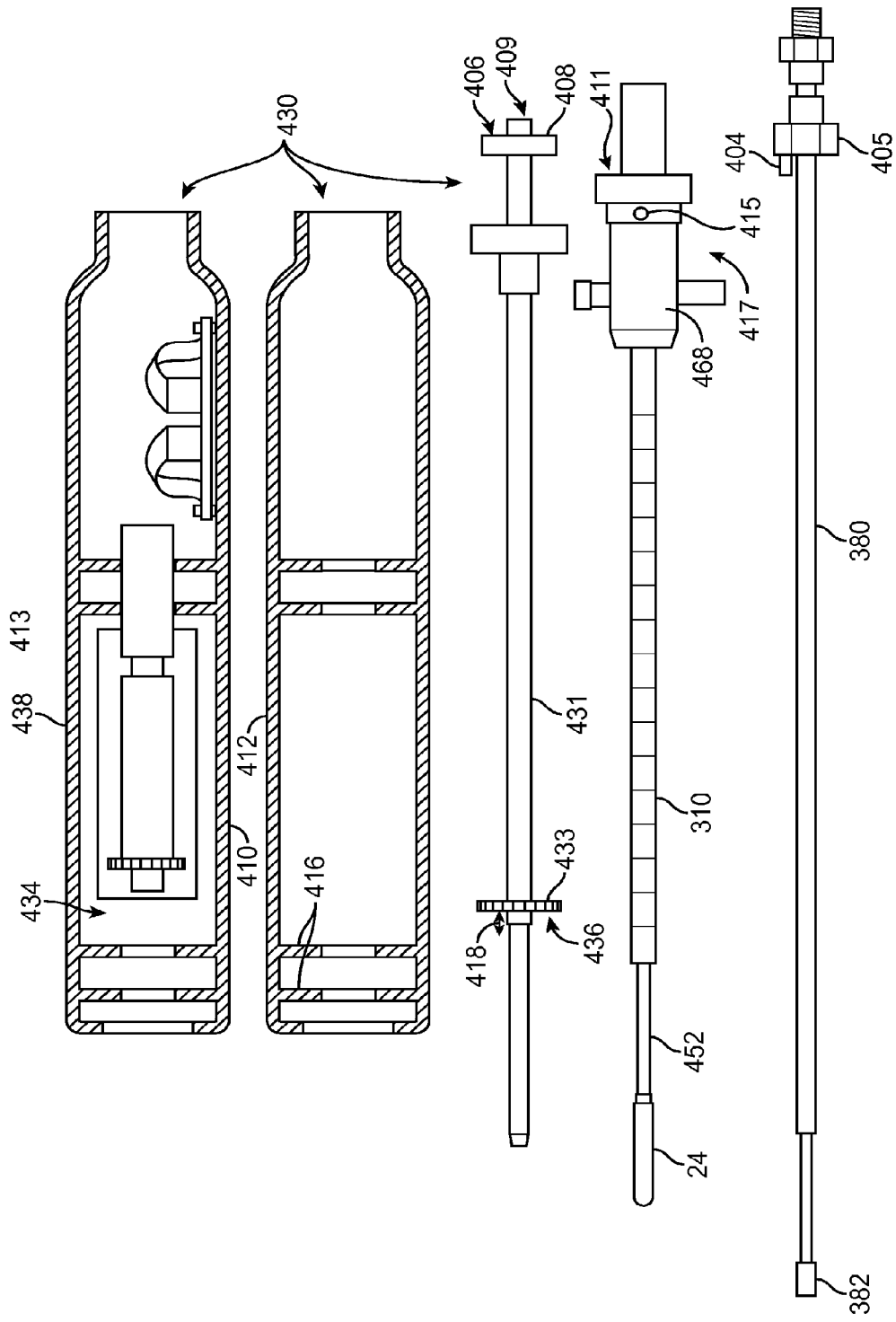
FIG. 14C shows components of treatment probe and linkage in accordance with embodiments.

FIG. 14C shows components of treatment probe and linkage disassembled prior to use. The linkage 430 comprises a casing 410 and a cover 412. The cover 412 can be placed on the lower portion of the casing 410. The cover and casing may comprise rigid materials to add stiffness. The casing and cover can be sized so as to comprise a handpiece containing the linkage 430. The linkage 430 comprises an elongate tubular structure comprising a gear 433 to engage another gear 434 of the linkage. The gear 434 can be positioned on a movable carriage 413. The elongate tubular structure may comprise second movable portion 436 of the linkage. The casing 410 may comprise the support 438 of the linkage. The gear 433 remains connected to the elongate tubular structure 431 when the linkage is disassembled. The movables portion of the linkage 430 may comprise gear 433, gear 434 and movable carriage 413 so as to advance the elongate structure 431 distally when connected to the second movable portion 436 as shown with arrows 418. The cover 412 comprises flanges 416. When the cover is placed on the casing, the elongate structure can be locked into position 431 on the linkage.

The elongate element 310 comprises a spine 452 as described herein and is shown covered with a sheath 458. The sheath 458 comprises a channel to receive the elongate element 310. The elongate element 310 comprises the working channel and can inserted into the sheath 458 such that the elongate element is covered with sheath 458. The sheath 458 and elongate element 310 are shown connected to manifold 468 as described herein.

The sheath 458 can be inserted into the patient prior to insertion of elongate element 310. In many embodiments, sheath 458 is coupled to manifold 468 when inserted into the patient.

The elongate element 310 is configured to slide into the sheath 458 such that the elongate element 310 and sheath comprise a locked configuration. The elongate element 310 comprises structure 411 configured to engage the housing 410 of the linkage, such that the elongate element 310 and housing 410 remain substantially fixed when the elongate structure 431 moves as described herein.

In many embodiments, casing 410 comprises support 438. The support 438 may comprise a substantially non-moving portion of the linkage 430 as described herein. The linkage 430 may comprise moving carriage 433 to move the carrier 382 when the casing 410 comprising support 438 remains locked to the arm and substantially non-moving as described herein.

In many embodiments, the structure 411 of the elongate element 310 comprises locking structure to form a locked joint with the casing 410 and cover 412.

In many embodiments, manifold 468 is connected to the sheath 458 and can be affixed to the sheath to inset the sheath 458 into the patient and inflate the balloon anchor 24 with the manifold 468 as described herein. The elongate element 310 comprising spine 452 may then be inserted into sheath 458. The manifold 468 and structure 411 comprises locking structures 417 to lock the manifold to the elongate element 310 when the elongate element 310 has been inserted into the manifold 468 and sheath 458. A release 415 can be pressed by the user to unlock the manifold 468 from the elongate element 310.

The elongate tubular structure 431 of the linkage 430 comprises structures to receive the carrier tube 380. An opening 409 of the elongate tubular structure 431 is sized to receive the carrier tube 380. A connection structure 408 is shown on the proximal end of the linkage, and comprises a locking structure 406 to receive a protrusion 404 of the connection structure 405 of carrier tube 308.

FIG. 14D1 shows rapid exchange of a carrier tube 380 when the linkage 430 is coupled to the elongate element 310 anchored to a target location of an organ. The elongate element 410 can be inserted or removed from the linkage by the user. The elongate element 380 can be advanced into opening 409 near connection structure 405 of the elongate tubular structure 431.

The imaging probe 460 can be mounted on a second linkage and configured to move with the nozzle of carrier 382, so as to image interaction of the energy stream from carrier 382 when tissue is treated. The images of the treatment may comprise axial images and sagittal images from the imaging probe 460. The linkage can be coupled to the controller or processor (or both) as described herein to move the imaging probe 460 synchronously along the axis with the carrier 382 and nozzle of the carrier, for example. The imaging probe 460 may comprise a trans-rectal ultrasound probe and the carrier 482 may comprise a component of the treatment probe 450 as described herein.

FIG. 14D2 shows alignment of the distal tip of the carrier 382 with the opening 409 of proximal end of the elongate tubular structure 431 to insert the carrier tube 380 as in FIG. 14D1.

FIG. 14D3 shows the carrier advanced toward a locking structure 406 on the proximal end of the linkage as in FIG. 14D1. The locking structure 406 is sized to receive protrusion 404 so as to form a locked joint 402.

FIG. 14D4 shows the carrier tube 380 locked to the linkage 430 as in FIGS. 14D1 and 14D2. The protrusion 404 has been inserted into an opening of locking structure 406 so as to form the locked joint. The joint can be unlocked by user manipulation.

Figure 14E:
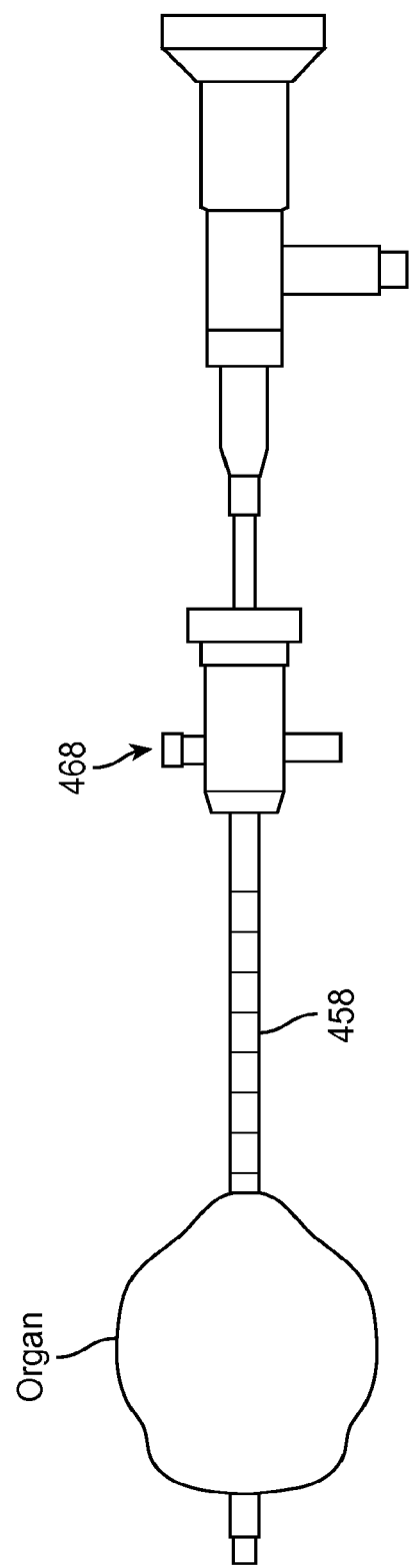
FIG. 14E shows a cytoscope inserted at least partially into an elongate element for advancement toward a bladder neck to view tissue of an organ such as the prostate, in accordance with embodiments.

FIG. 14E shows a cytoscope inserted at least partially into a sheath 458 for advancement toward an anchoring location of an organ. The anchoring location may comprise a bladder neck to view tissue of an organ such as the prostate. The sheath 458 as described herein can be advanced to a target location with visualization from the cytoscope placed within the working channel of the elongate element 310. When positioned, the anchor 24 such as a balloon can be inflated with a port of manifold 468 coupled to the sheath as described herein.

There are at least two forms of visualization possible with the embodiments as described herein. 1) The cystoscope is locked within the sheath 458. The purpose can be to view the prostate and then eventually leave the sheath as a safe channel to guide the elongate element 310 comprising spine 452 into the patient, in many embodiments without having direct visualization. The distal end of the sheath lines up near bladder neck. 2.) Once the elongate element 310 is locked into the sheath 458, ureteroscope can be used to view the patient. The ureteroscope can be inserted inside the same channel that carrier 380 goes into, for example shared channel.

Figure 14F:
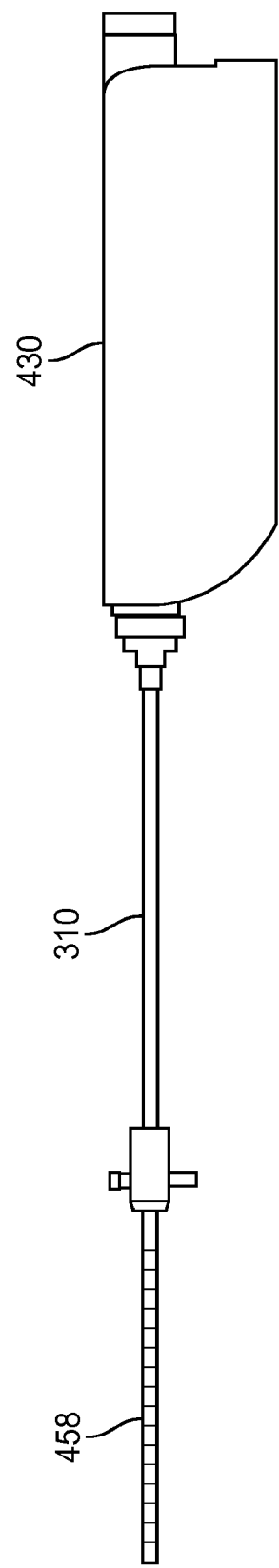
FIG. 14F shows advancement of an elongate element into a sheath.

FIG. 14F shows advancement of an elongate element 310 into a sheath 458. The manifold 468 on the proximal end of the sheath 458 may comprise a locking structure to receive a locking structure on the proximal end of elongate element 310. The elongate element 310 can be advanced into sheath 458 such that the locking elements on the sheath 458 and elongate element 310 engage.

Figure 14G:
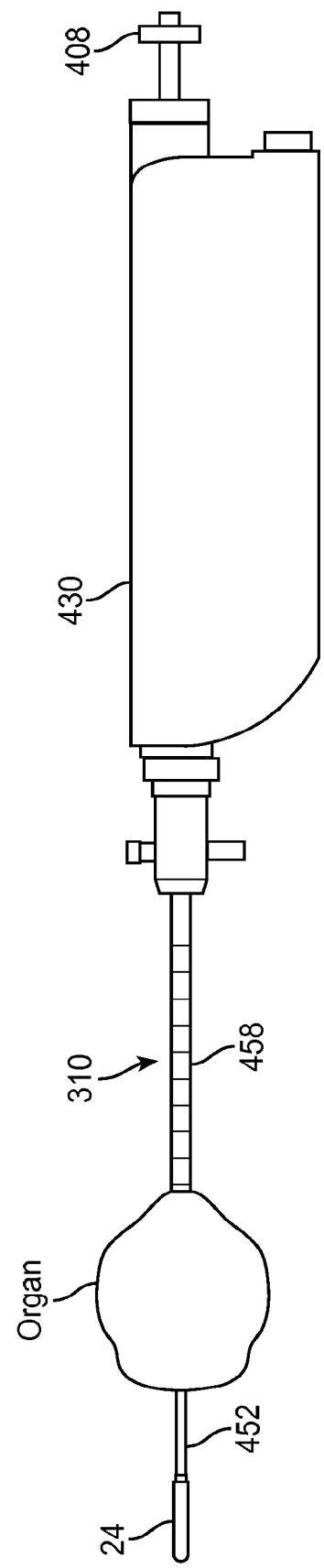
FIG. 14G shows a linkage coupled to an elongate element comprising a spine in accordance with embodiments.

FIG. 14G shows a linkage 430 coupled to an elongate element 310 comprising a spine 452. The linkage is configured to receive carrier 382 and carrier tube 380 as described herein.

Figure 14H:
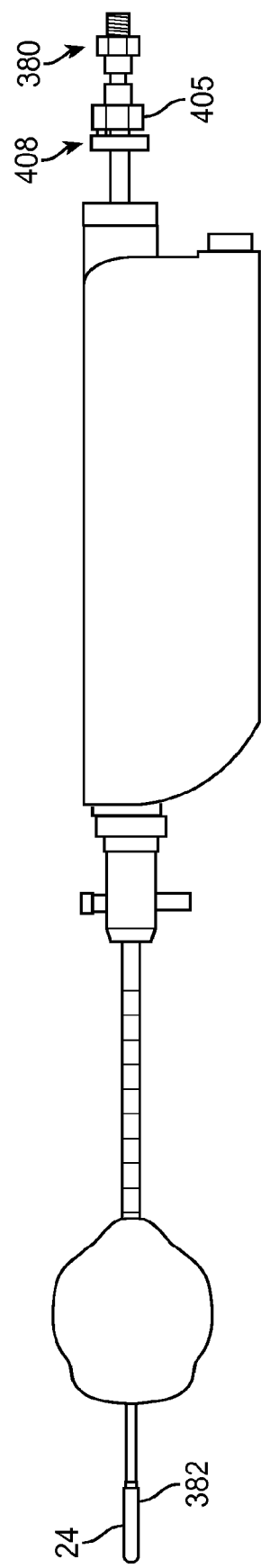
FIG. 14H shows a carrier tube and carrier inserted into the linkage tube in accordance with embodiments.

FIG. 14H shows a carrier tube and carrier inserted into the linkage tube in a locked configuration as described herein.

FIGS. 14A to 14H show a method of treating a patient in accordance with embodiments, and each of these figures shows one or more optional steps of the method.

FIGS. 15 and 16 show self cleaning with a fluid jet as described herein. The fluid jet, for example fluid stream, as described herein, can be utilized to clean the working channel and clear tissue or other ports within the multifunction sheath. The self cleaning can be automated or performed manually. Additionally, water jet intensity can be reduced to clean laser cameras or other accessory devices without having to remove the devices from the working channel. For example an endoscope can be sized to fit within the working channel or alternatively an endoscope can be sized to fit within the working channel with the linkage decoupled and to allow flushing and cleaning of the working channel. Alternatively or in combination the carrier 382 that may comprise carrier tube 380 can be sized to fit within the working channel alongside an endoscope so as to allow cleaning of the endoscope.

In many embodiments the self cleaning can be employed with the probe comprising carrier 382 that may comprise carrier tube 380 positioned within the working channel. The elongated element 310 comprising the sheath and spine can contain the carrier 382 that may comprise carrier tube 380 along a substantial portion of the carrier. The carrier 382 may comprise a rectangular end portion or a tubular end portion and may comprise a portion having a cylindrical and tubular geometry, for example. The fluid stream released from carrier 382 can extend to distance 457 with divergence, for example.

Alternatively the fluid stream may comprise a columnar fluid stream. An angle of the fluid stream 453 can be controlled with the linkage so as to rotate the fluid stream during cleaning. The fluid stream can be increased or decreased in terms of pressure.

The fluid jet can be utilized to clean the working channel and clear tissue or other parts within the multifunction sheath. This can be automated or performed manually. Additionally water jet intensity can be reduced to clean the laser camera or other accessory devices without having to remove the devices from the working channel.

Figure 17A:
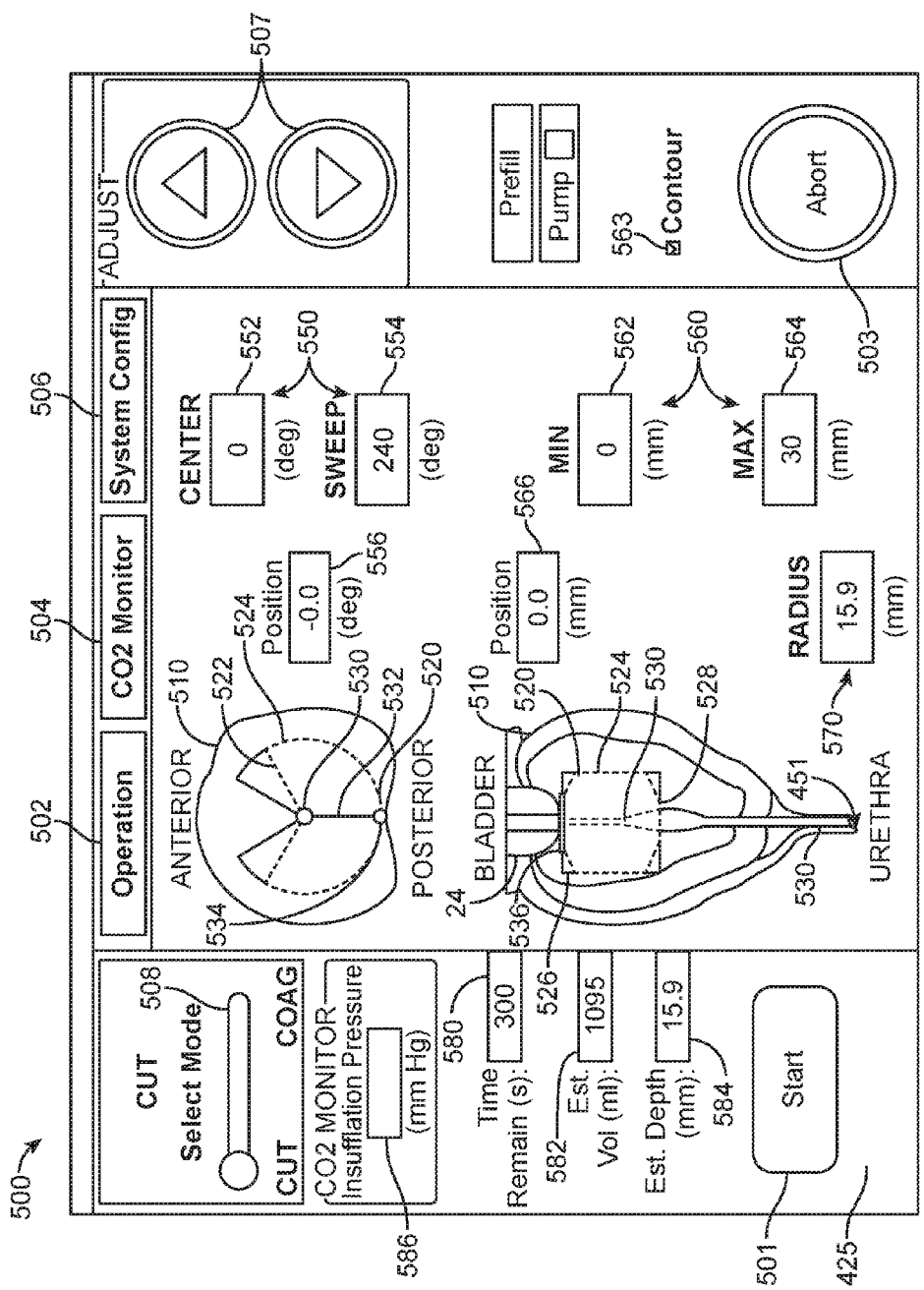
FIG. 17A shows components of user interface on the display of the patient treatment system as in FIG. 13 in accordance with embodiments.

FIG. 17A shows components of user interface 500 on the display 425 of the system 400. The display 425 may comprise a touch screen display, for example, alternatively or in combination, the display 425 can be coupled with a pointing device, a keyboard, and other known user input devices to work with processor systems. The interface 500 comprises an operation tab 502, a CO2 monitor tab 504, and a system configuration tab 506. The user interface 500 includes buttons 507 on the display to adjust up or down values entered into the computer system. An abort button 503 is provided on the user interface for the user to stop treatment of the patient. A start button 501 is provided for the user to initiate treatment of the patient. The user interface 500 comprises an image 510 of an organ such as a prostate. The image 510 shown can be an image of one or more of many organs as described herein. The image 510 may comprise, for example, an image of a prostate from an anatomical image corresponding to a prostate of a patient. The image 510 is shown in an axial transaxial cross-sectional view having an anterior and a posterior orientation, the image 510 is also shown along the longitudinal axis. The sagittal view of the image 510 along the longitudinal axis shows anchor 24 and a lumen such as the urethra. The image 510 may comprise an image of the patient to be treated, for example, an ultrasonic image of the patient. The image 510 can be shown in axial and sagittal views with the ultrasonic image sized so as to correspond with the treatment profiles shown on the display 425.

A treatment profile 520 is shown in the axial and sagittal views. The treatment profile 520 corresponds to a profile of tissue to be removed in the surface remaining subsequent to removal. The treatment profile 520 comprises a radius 522 extending from a central reference location to an outer portion of the cut tissue boundary. The treatment profile 520 comprises an outer component 524 extending circumferentially around an axis of the treatment. The treatment profile 520 extends from a first end 526 proximate the bladder and the anchor to a second end 528 toward the urethra. The treatment profile images shown on the display comprise a plurality of references to align the treatment with the anatomy of the patient. An axis 530 corresponds to a central location of the treatment and extends axially along a lumen of the patient such as the urethra. The treatment axis 530 may correspond to an anatomical reference of the patient such as the urethra or path with which the instrument is introduced to the patient. An angular reference 532 is shown extending from the central axis of the treatment profile to an outer radial boundary of the treatment profile 534. The angular component 532 corresponds to an anterior posterior location on the component of the patient and extends from the anterior to the posterior to location 534 to provide and permit alignment with the patient. As can be seen in the sagittal view, a treatment reference location 536 corresponds to a location adjacent the inflatable anchor such as a balloon 24. Reference location 536 corresponding to the expandable anchor is shown aligned with the end 526 of the treatment profile 20 in which the treatment profile is shown aligned with the axis 451 of the treatment probe.

The user interface 500 comprises a plurality of inputs. The plurality of input may comprise one or more of the following inputs as described herein.

A plurality of angular input parameters 550 may comprise input 552 and input 554, for example. The angular orientation can be set so as to align with an anterior posterior direction of the patient extending between axis 530 and marker 534. The input 552 can be used to adjust the angular orientation of the treatment around the axis 530, for example, when the patient and probe are aligned at slightly different angles. An input 552 aligns the center of the treatment profile in degrees rotationally around the axis. An input 554 provides a sweep angle from one angular extreme to another, for example, a sweep angle may comprise an angle less than 360°, for example, 240°. The sweep angle generally extends around the anterior-posterior treatment axis and extends from the anterior end treatment posterior treatment axis by a distance of approximately half the sweep angle, for example, sweeping 120° in the first direction and sweeping 120° in an opposite direction from the anterior posterior treatment axis. In many embodiments, the sweep angle is limited to less than 360 degrees to avoid sweeping the fluid stream into the spine.

The angular position of the stream can be shown in real time on the display with an output 556 of the angular position in degrees. The output angle can be shown on the display as a moving colored line, for example green, which sweeps around the axis 530. The position 566 can also be shown on the display in millimeters and degrees.

A plurality of input parameters 560 can be used to determine the extent of the treatment along axis 451 and axis 530. An input 562 determines a location of the treatment profile in relation to expandable anchor 24. A contour checkbox 563 is shown on the display. An input 564 determines a length of treatment along axis 451 and axis 530. Input 564 may comprise a longitudinal distance of the treatment extending from a first end 524 to a second end 528. An input 570 can determine a radius of the treatment profile around axis 530. Input 570, a radial distance from axis 530 radially outward to an outer boundary of the treatment profile 524. The radius may comprise a radial distance in millimeters such as the distance of 10 mm for example. Alternatively, the radius can be determined with power of a pump which can be set with arbitrary values from 1 to 10, for example.

A select mode input 508 can allow the user to set the interface from a cut mode to a coagulation mode, for example. In the cut mode, many of the inputs for the treatment can be provided so as to determine and align the treatment with the patient. In the cut mode as shown the user is able to visualize the extent of treatment with respect to the anatomy of the patient and to formulate and improve treatment strategy. The user can establish a cut profile having a predetermined profile surface and a predetermined removal volume.

The patient interface comprises additional outputs for the user to determine appropriate treatment, for example, a time remaining in the treatment can allow the user to determine the time of treatment and the time remaining in the treatment, for example, an output 580 shows the time remaining in seconds. An output 582 comprises an estimated volume of tissue removal, the estimated volume of tissue removed can be determined based on the treatment profile. An estimated radial depth of the removal can also be determined and an output 584 can show the estimated radial depth of removal. The estimated depth of removal may comprise the input radius from input 570 alternatively the estimated depth may correspond to an estimated depth from a pump power of input 570. A start button input 501 allows a user to start treatment when the physician is satisfied with the patient treatment. When insufflation is used, for example insufflation with a gas such as $CO_2$ an insufflation pressure can be set with an input 586. Alternatively, if liquid is used as described herein as a second or first fluid in combination with another liquid insufflation pressure may be set to zero or disabled. In many embodiments the insufflation may be set to zero in a first mode such as the cut mode and set to an appropriate value in a second mode such as the coagulation mode.

Figure 17B:
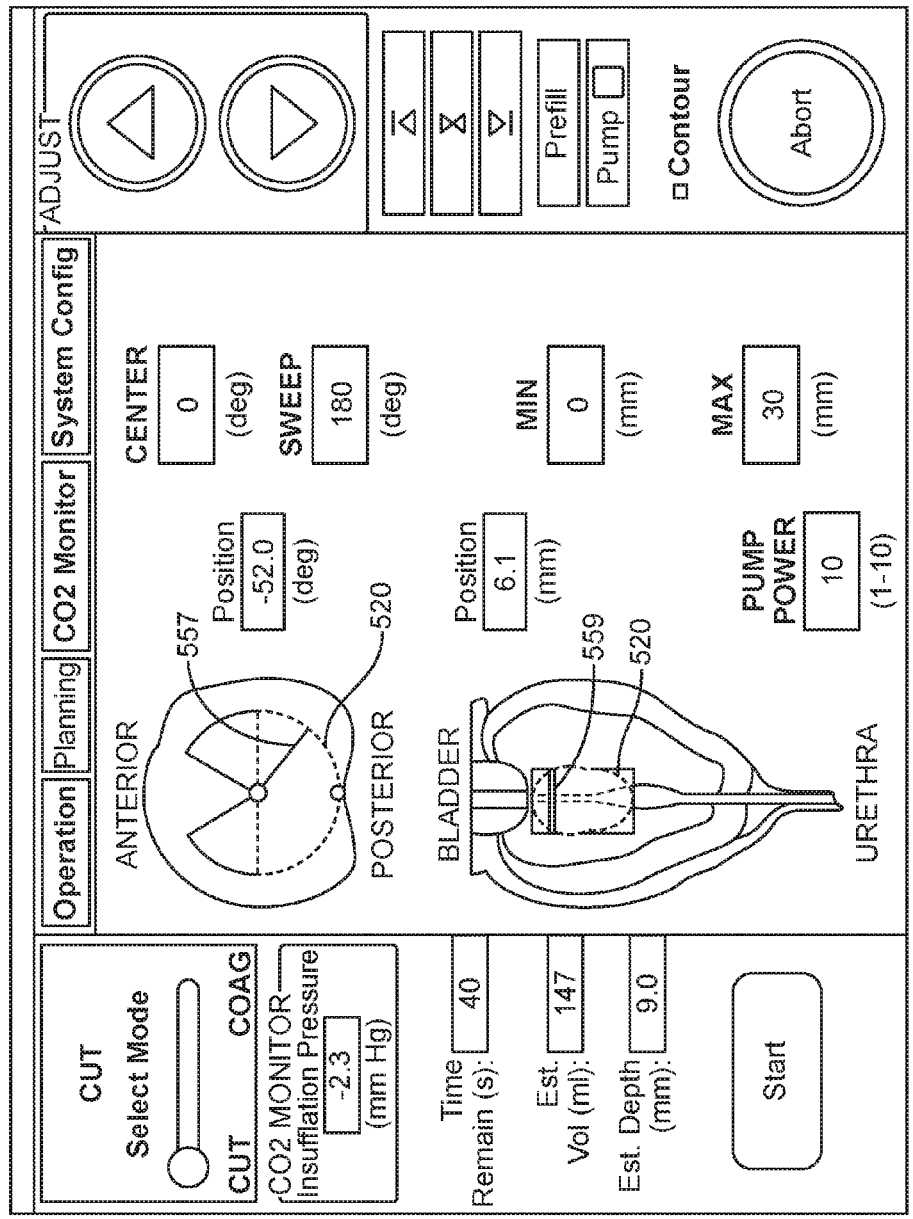
FIGS. 17B and 17C show a marker moving on a plurality of images in which movement of the marker corresponds to the position and orientation of an energy stream in accordance with embodiments.
Figure 17C:
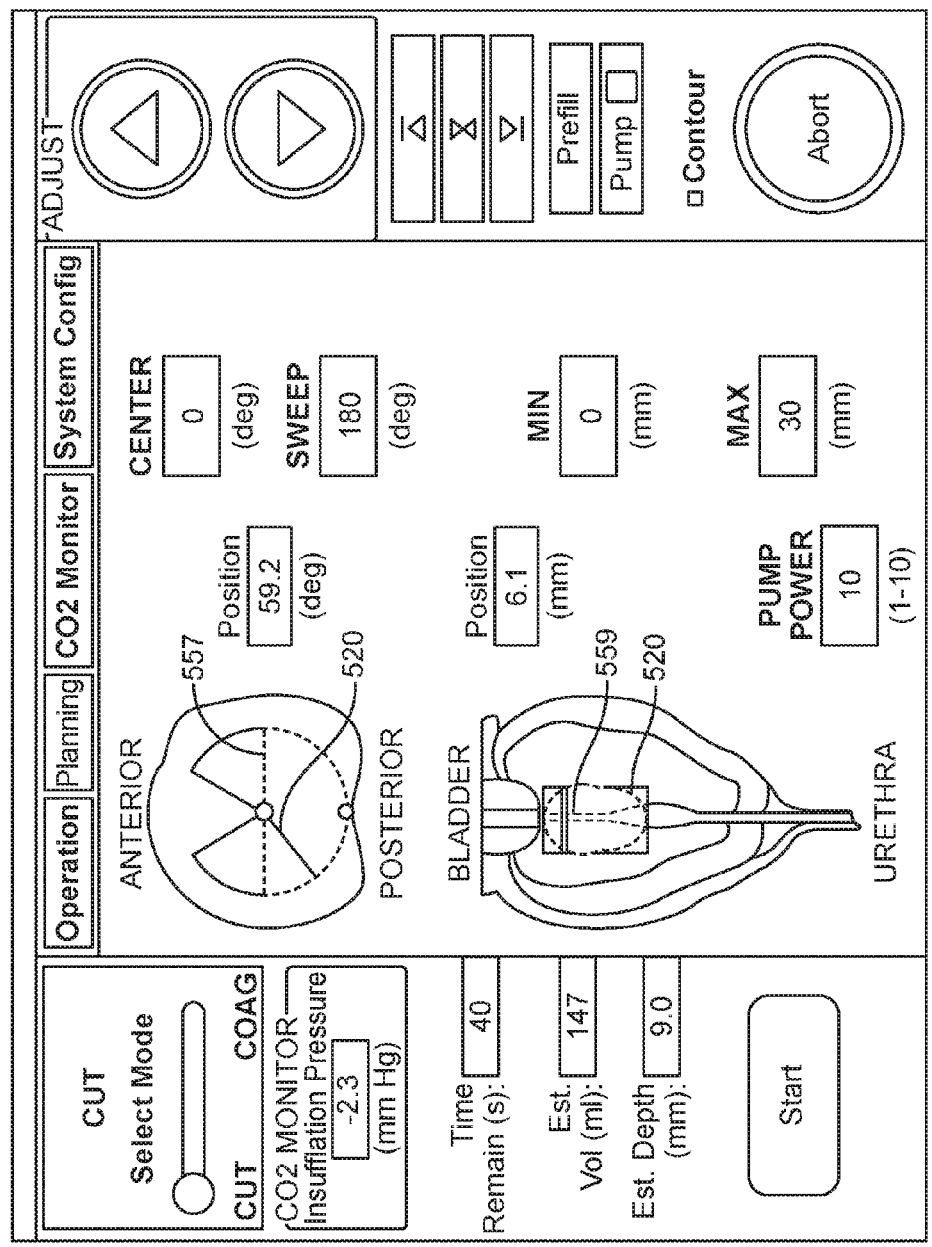

FIGS. 17B and 17C show a marker moving on a plurality of images in which movement of the marker corresponds to the position and orientation of an energy stream. The energy steam may comprise a fluidic stream from the nozzle as described herein. A radial marker 557 is shown on the axial image in relation to the resection profile 520. A longitudinal marker 559 is shown on the sagittal image in relation to resection profile 520. The radial marker 557 is shown at a first angle in FIG. 17B and a second angel in FIG. 17C so as to indicate the angle of the fluid stream from the carrier as described herein, for example. As the treatment progresses, the longitudinal maker 559 can move along the treatment axis of the sagittal image to indicate the longitudinal position of the nozzle on the carrier as the radial marker 557 sweeps rotationally around the axis on the axial image.

Figure 17D:
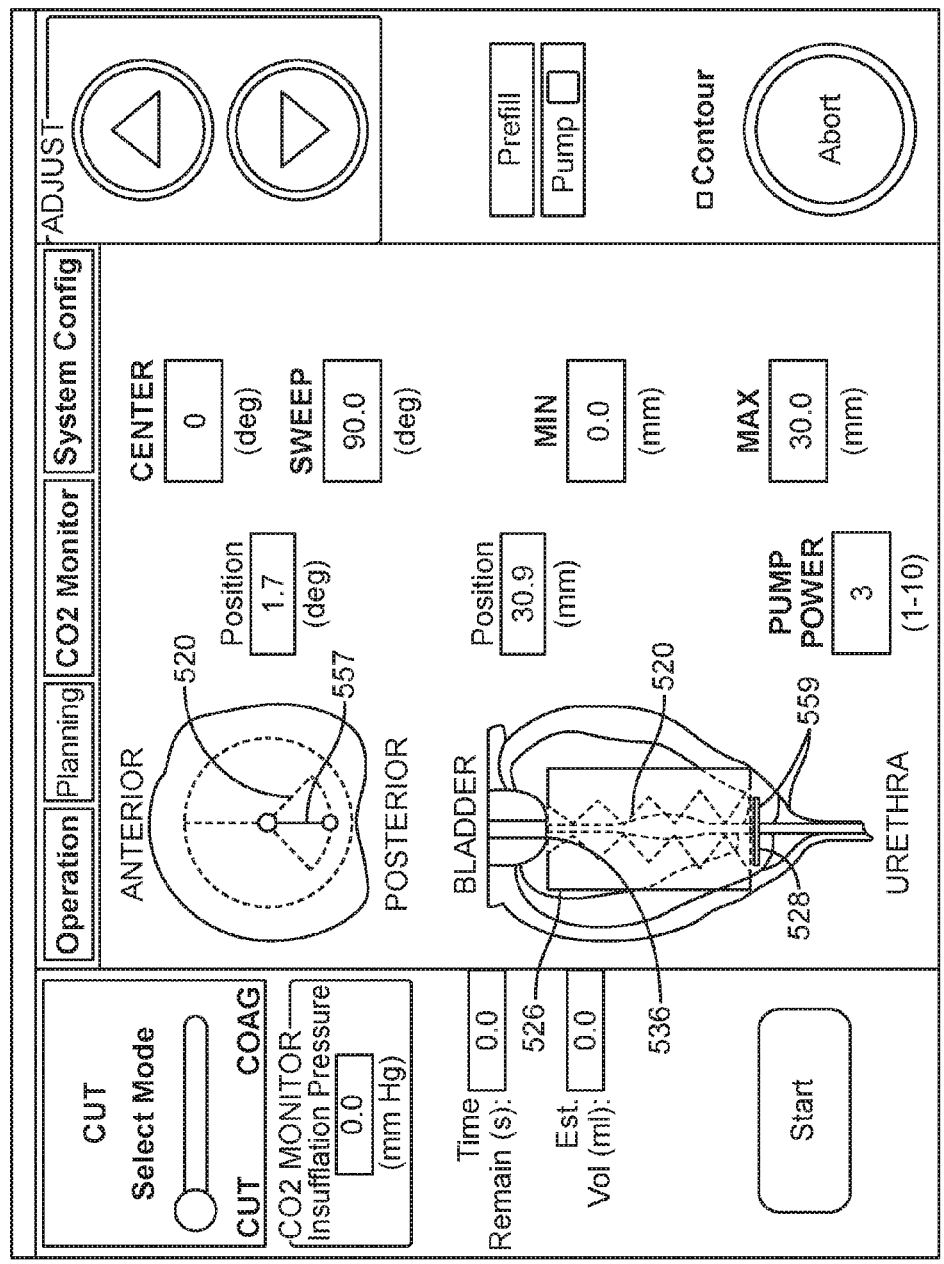
FIG. 17D shows a user defined cut profile in accordance with embodiments.

FIG. 17D shows a user defined resection profile 520. The user interface can be configured with instructions of the processor to allow the user to define a plurality of points of the treatment profile, and interpolate among the points as described herein.

Figure 17E:
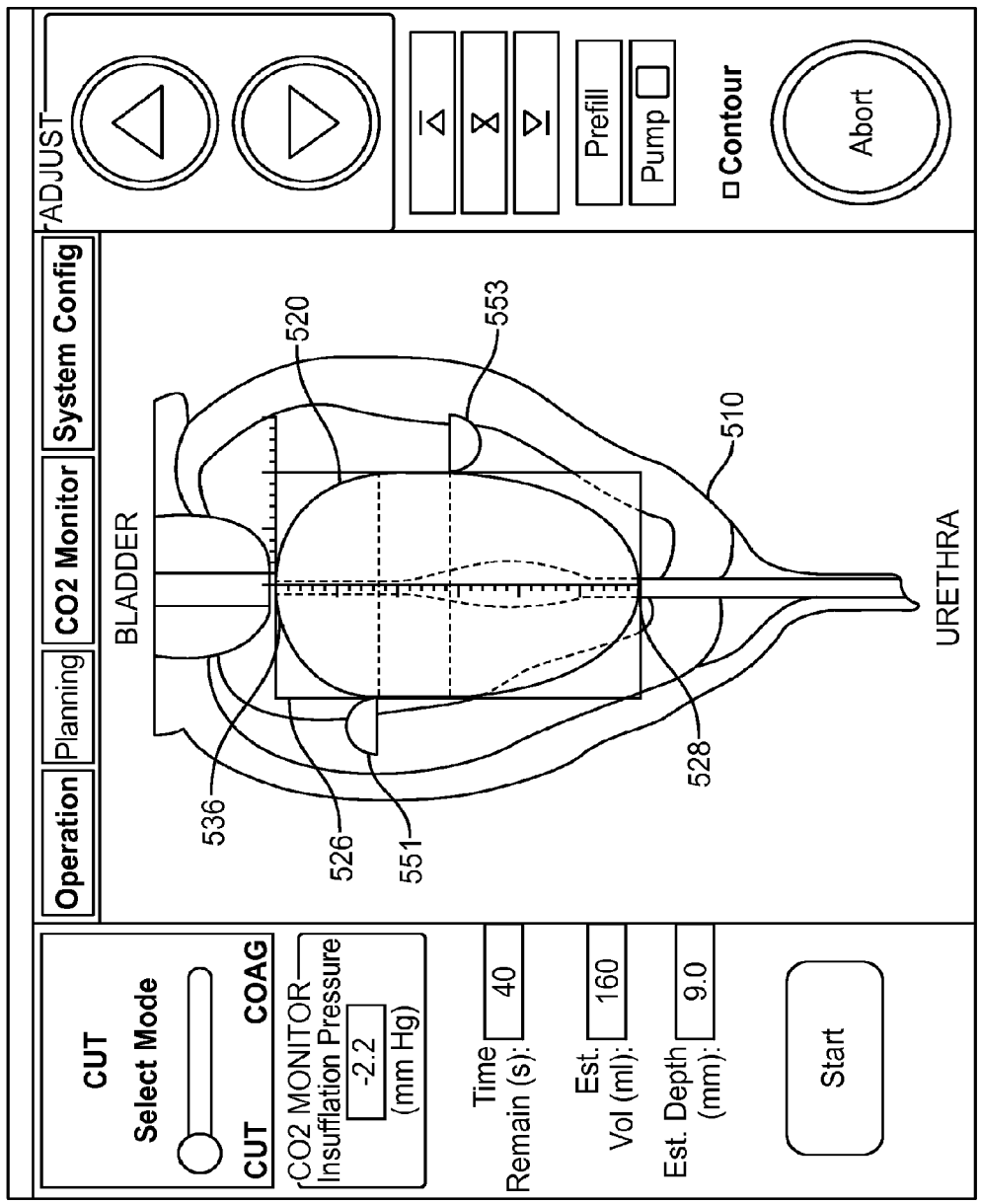
FIGS. 17E and 17F show a user interface to define a plurality of curved portions of a cut profile in accordance with embodiments.
Figure 17F:
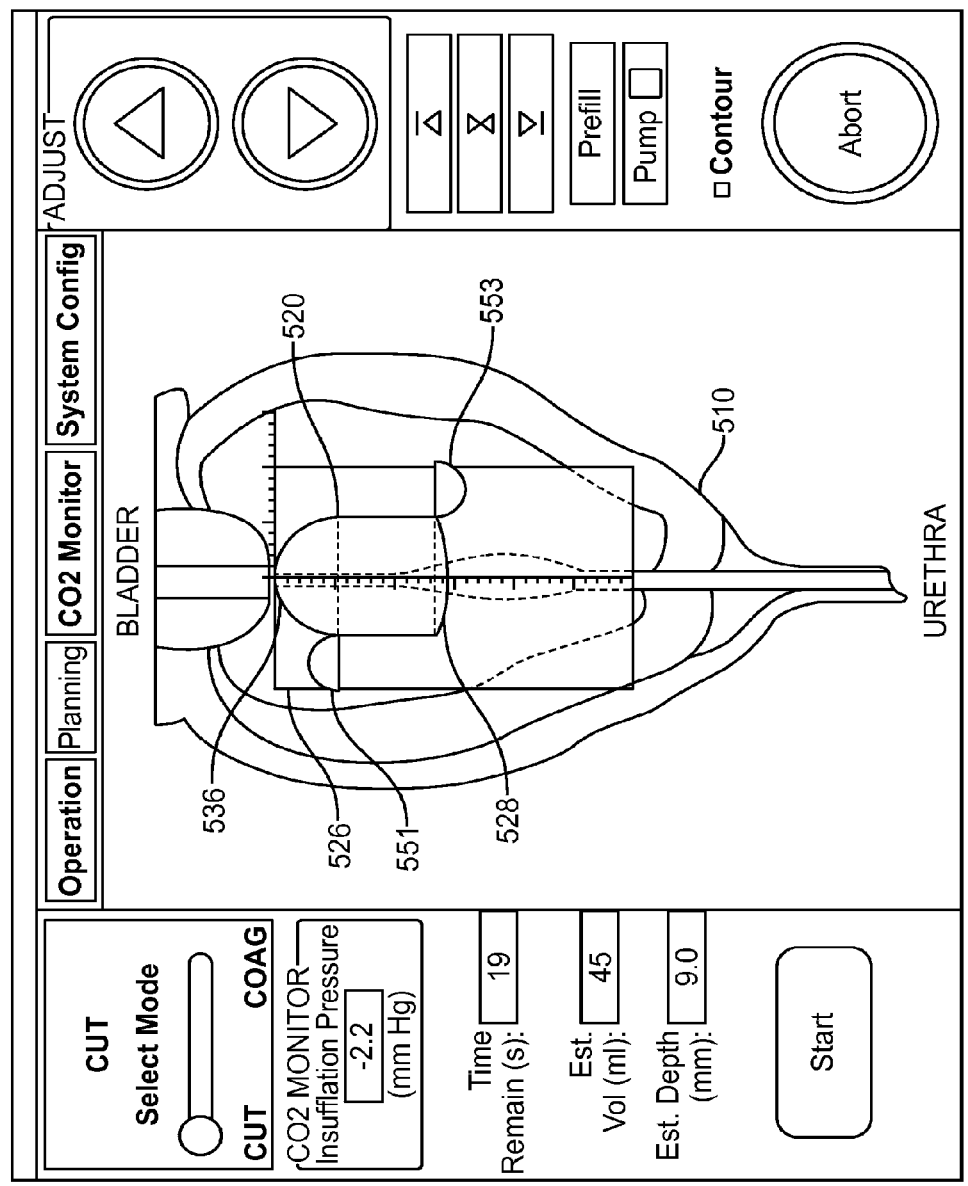

FIGS. 17E and 17F show a user interface to define a plurality of curved portions of a cut profile. A first user movable input 551 can be configured to move along the display to define a first curved portion of the profile 520, and a second user movable input 553 can be configured to move along the display to define a second curved portion of the profile 520, and the instructions of the processor can be configured to interpolate among the first curved portion and the second curved portion to define the profile 529 extending between the first curved portion and the second curved portion, for example. A first end 526 of the treatment profile can be set based on user input and a second end 528 can be set based on user input as described herein. The user can slide the first movable input 551 to determine the curved shape of the first portion based on anchoring of the cut profile with the end 526 and the location of the movable input 551 on the display. For example, the first curved shape may be determined with a spline fit extending from the first input to the end 526 constrained with angles at the end 526 and the movable input 551. The second movable input 553 can be moved similarly to define the second curved shape of the second portion, for example.

Figure 18:
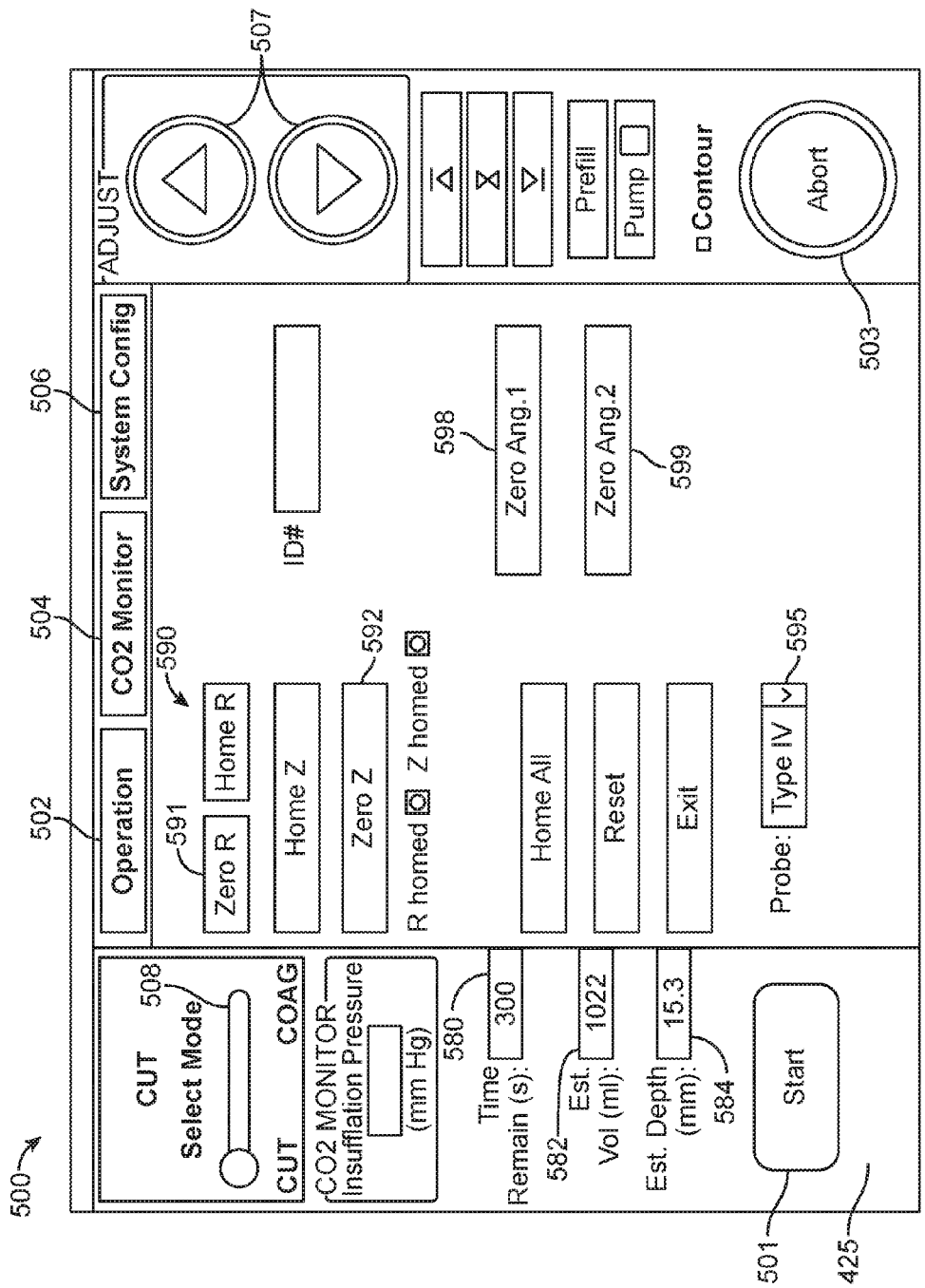
FIG. 18 shows a system configuration mode for the cutting mode input of the user interface as in FIG. 17A.

FIG. 18 shows a system configuration mode 506 for the cutting mode input 508. When the system configuration is set the user can set several parameters for the treatment prior to the treatment or during the treatment so as to align the treatment profile with a patient and to insure that the treatment probe 450 cuts tissue as intended. One or more inputs 590 allows the user to align intended treatment with the probe placed in the patient. One or more inputs 590 may comprise an input 591 to zero the treatment and align the treatment axis with an axis of the patient, for example the intended anterior posterior treatment profile can be aligned in an anterior posterior direction of the patient such that an anterior posterior axis of the treatment profile is aligned with an anterior posterior axis of the patient. Input 591 can be set based on one or more measurements for example an ultrasonic imaging measurement to determine that the probe is properly aligned with the patient. Alternatively or in combination, input 591 can be set based on angle sensors as described herein. One or more inputs 590 may comprise an input 592 to zero the treatment in the axially direction and align the treatment probe with an intended anatomic target of the patient. Input 592 allows alignment of the longitudinal axis with the intended target location of the patient, for example if treatment probe 450 has been placed insufficiently far or too deep the zero z button can be pressed such that input 592 zeros the treatment at the correct anatomical location.

The system configuration mode can also be used to set and calibrate the system. For example, an input 598 can allow the zero angle of a first angle sensor, for example, an angle sensor of the treatment probe 450 to be set to zero and properly aligned. An input 599 can be used to set the imaging probe sensor to an appropriate angle, for example, to calibrate the imaging probe.

An input 595 can allow a user to select a probe type from among a plurality of probe types, for example the probe type may comprise a plurality of nozzle types, for example, a fourth nozzle type may comprise a narrower nozzle diameter to allow treatment at a greater distance radially from the axis of the treatment probe 450. In the system configuration mode for a given profile a user can select a plurality of probe types so as to determine a time remaining, an estimated volume and an estimated depth based on the probe identified and, for example, the size of the nozzle of the probe selected.

By way of example, the input screens and parameters shown in FIGS. 17A and 18 may refer to a divergent cutting screen in which a first fluid comprises a liquid and the second fluid comprises a liquid. Alternatively a gas can be used to provide a protective jacket around a treatment beam in a treatment stream so as to extend the effective cutting distance of the treatment probe 450. The system may comprise instructions so as to perform a portion of the treatment with one configuration of the first fluid and the second fluid and a second configuration of the first fluid and second fluid so as to cut a second portion of the treatment with a gas protecting the treatment stream.

In many embodiments in which the sweep angle is limited to less than 360 degrees to avoid the spine as described herein, a first treatment can be performed at a first angular orientation of the probe about the axis, the probe rotated to move the spine out of the way in order to expose the untreated portion with the stream, and a second treatment performed. The angle of the probe for the first treatment can be measured, and the angle of the probe for the second treatment measured, and the treatment rotated to treat the untreated portion based on the first and second angles. For example, the first treatment may comprise a sweep of 240 degrees, and the second treatment may comprise a sweep of 120 degrees, such that the total treatment extends substantially around the axis of the probe and to a greater angle than would be provided if the spine were not rotated to expose the untreated portion. The probe may be rotated to a second measured angle, for example 70 degrees, and the second treatment performed with a sweep of 120 degrees. The center location can be adjusted with input 552 or software, such that the second treatment is aligned with the untreated portion.

Figure 19:
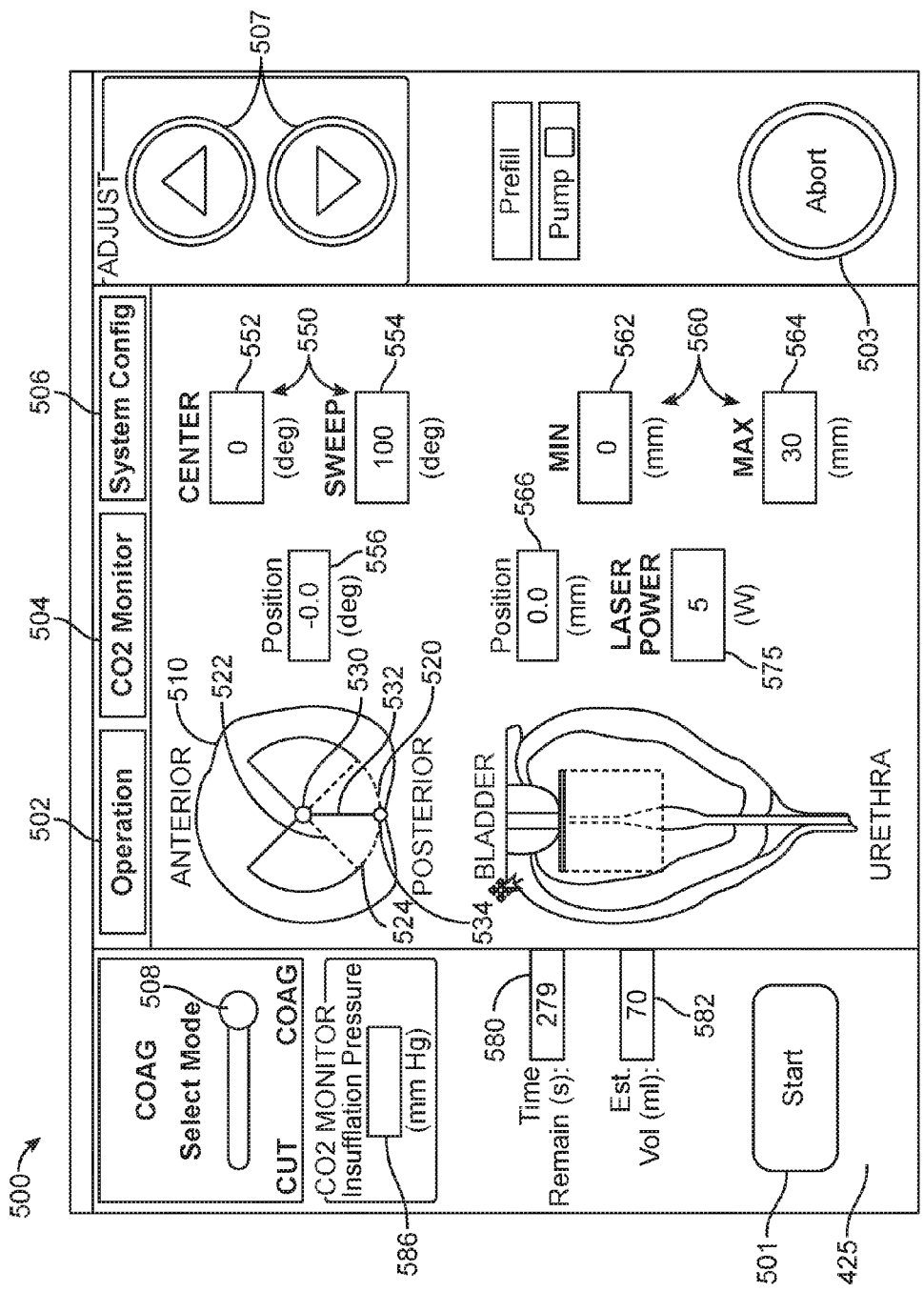
FIG. 19 shows a coagulation mode selected with input of the user interface as in FIG. 17A.

FIG. 19 shows a coagulation mode selected with input 508. With the operation tab selected with input 502, the treatment for coagulation can be set. The coagulation can be provided in many ways, for example, with a divergent stream or a columnar stream and combinations thereof. In many embodiments it may be desirable to treat only a portion of the treatment profile with coagulation. For example, a posterior portion of an organ, for example, the prostate can be selectively treated with coagulation. Work in relation to embodiments suggest that posterior treatment may result in slightly more bleeding potentially and it can be advantageous in some embodiments to selectively treat a posterior portion of a patient's anatomy, for example, the prostate. In the coagulation mode with a laser beam, the treatment input parameters are similar to those described above with respect to cutting. The sweep angle can be set with input 554, for example, to a value of 100° in which the sweep angle for coagulation is less than a sweep angle for cutting. The time of treatment remaining 580 can be shown and the user may also see a volume of treatment, for example, a coagulation volume. The user is allowed to select laser power with an input 575 and also to position the treatment similarly to what was done with the cutting and the angular extent can be lesser and the longitudinal extent can be lesser or greater, for example.

The input treatment profile can be input in one or more of many ways, for example, the image of the organ to be treated, for example, the prostate, can be provided and the user can draw an intended treatment profile on an axial view and a sagittal view of the patient. The image shown may comprise an anatomical image corresponding to anatomy of a generalized population or alternatively the images shown may comprise images of the patient. The processor system comprises instructions to map and transform the reference treatment profile on the image of the patient to the machine coordinate references of the treatment probe 450 and linkage 430 and anchor 24 as described herein. In many embodiments the images shown to the user are scaled to correspond to the treatment profile so that the treatment profile shown on the image of the anatomical organ treated corresponds to and aligns with the treatment dimensions of the image. This allows the user to accurately determine and place the intended treatment profile on the patient.

Figure 20A:
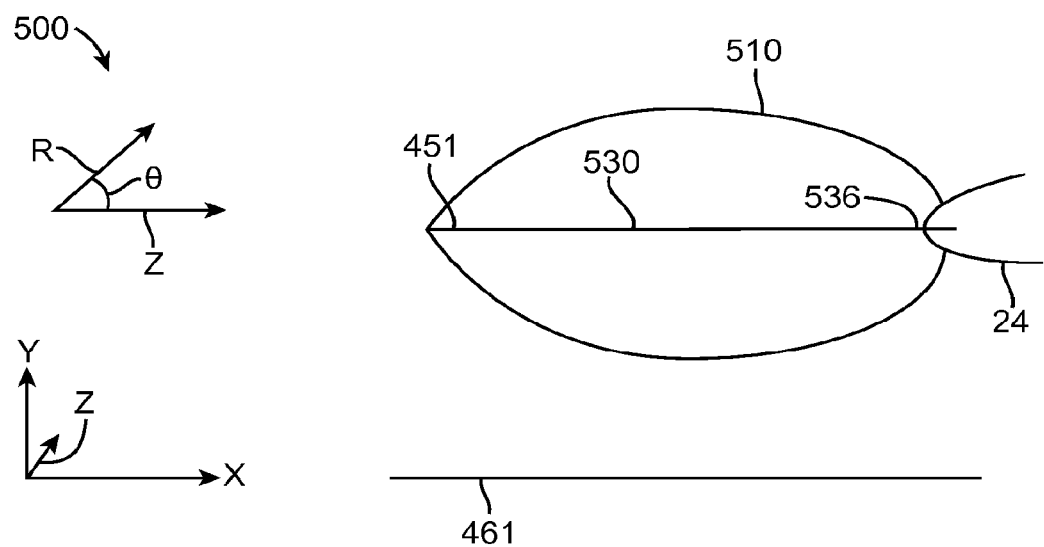
FIG. 20A shows mapping and alignment of an image of the patient with the treatment coordinate reference frame in accordance with embodiments.

FIG. 20A shows mapping and alignment of an image of the patient with the treatment coordinate reference frame. The image 510 of the organ can be obtained in one or more of many ways as described herein. The image may comprise an image reference frame, for example comprising X, Y and Z coordinate references. The treatment probe 450 comprises a treatment reference frame, for example cylindrical coordinate references R, Z, theta. The orientation of the axes of the probes can be determined as described herein. A marker reference 536, such as the anchor of the treatment probe can be identified from the image, in order to align the two images with a common known reference point. The points of the image from the image reference frame can be mapped to the coordinate reference frame and shown on the display, based on the location of the identified reference point and the orientation of the probes. A point in the image having an image coordinate reference of (X1, Y1, Z1) can be mapped to the treatment reference frame to provide treatment reference location (R1, Z1, T1). A three dimensional mapping of the patient tissue can be similarly performed, for example.

Three dimensional mapping of the tissue of the target organ can be performed, and the three dimensional mapping used to provide a three dimensional profile of the target organ. For example, a plurality of sagittal views and plurality of axial views can be provided of the three dimensional profile of the organ, and the user can draw the target treatment profile on each of the plurality of sagittal views and each of the plurality of axial views in order to provide a customized treatment of the patient. In many embodiments, the processor comprises instructions to interpolate the treatment profile among the sagittal an axial views, so as to provide a mapped three dimensional treatment profile. In many embodiments, providing additional treatment of the prostate medially may provide additional tissue removal, and the mapping as described herein can be used to provide additional removal of medial portions of the prostate tissue.

In many embodiments, the user can identify a plurality of points of a treatment profile on the image of the tissue of the patient, and the plurality of points are mapped to the treatment coordinate reference, and shown on the display so that the user can verify that the treatment coordinates of the treatment profile shown on the display treat the targeted tissue as intended by the user.

Figure 20B:
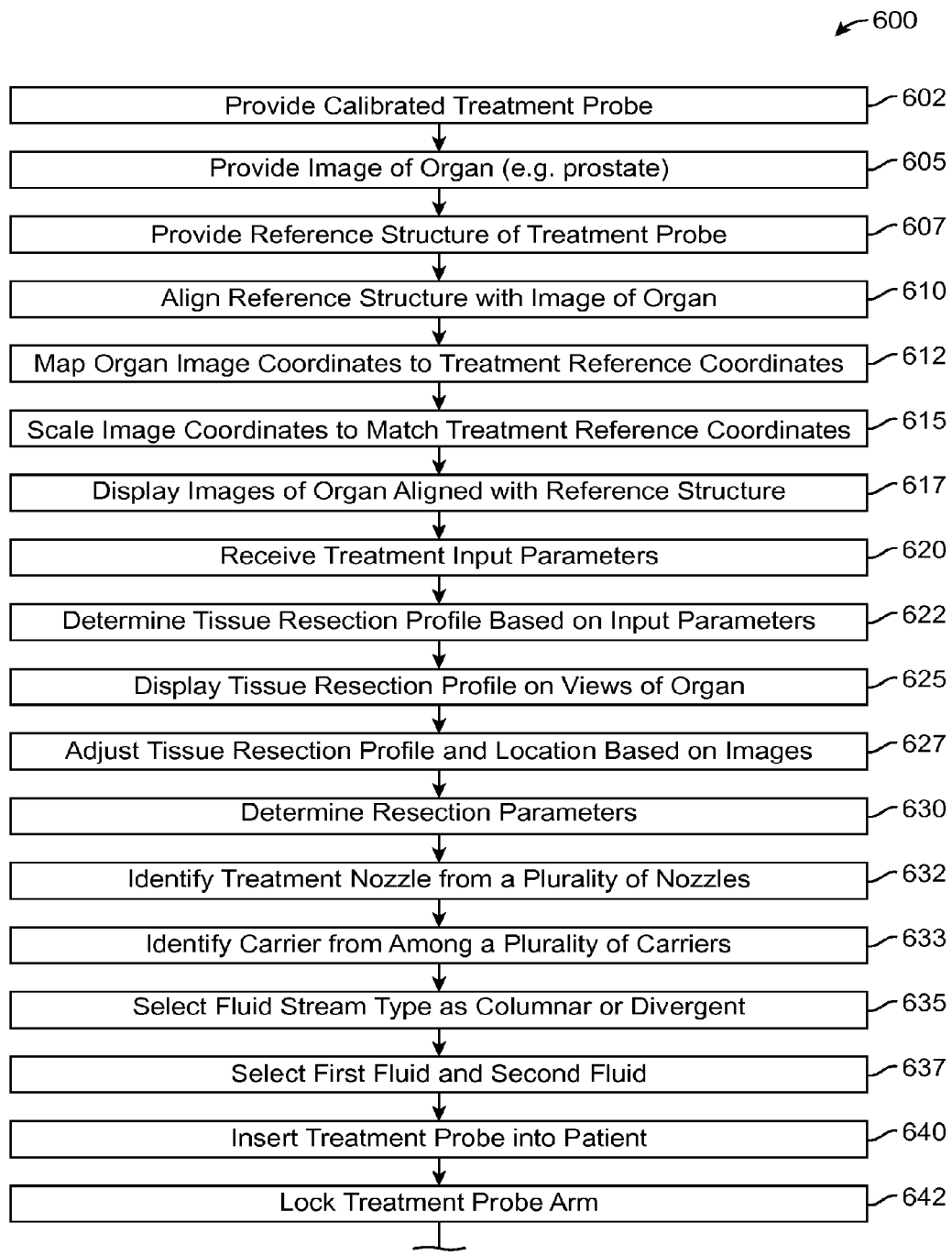
FIG. 20B shows a method of treating a patient in accordance with embodiments.
Figure 20B:
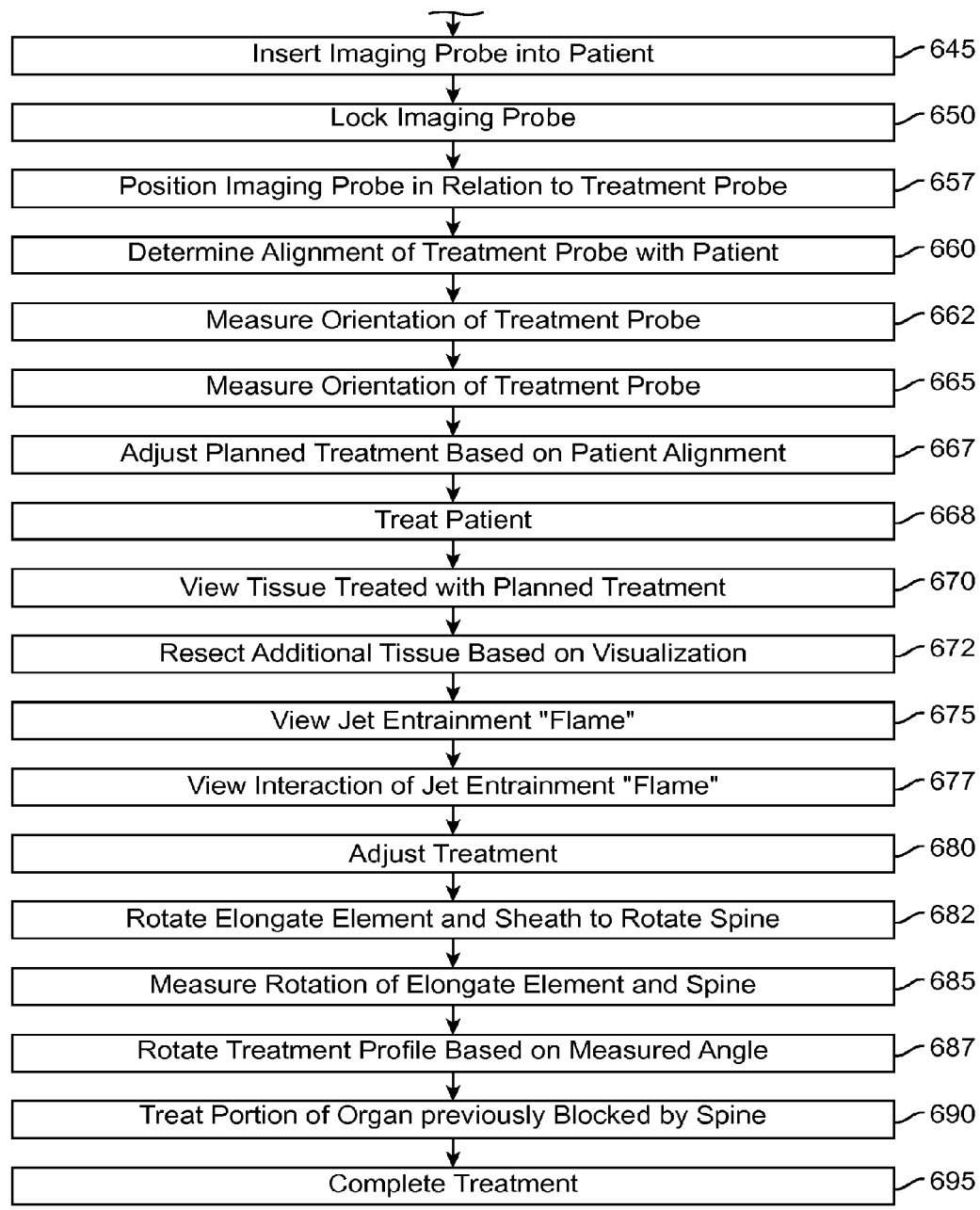

FIG. 20B shows a method 600 of treating a patient.

At a step 602, a calibrated treatment probe as described herein is provided.

At a step 605, an image of an organ (e.g. prostate) as described herein is provided.

At a step 607, a reference structure of a treatment probe as described herein is provided.

At a step 610, the reference structure is aligned with the image of the organ as described herein.

At a step 612, organ image coordinates are mapped to treatment reference coordinates as described herein.

At a step 615, image coordinates are scaled to match treatment reference coordinates as described herein.

At a step 617, images of the organ aligned with reference structure are displayed as described herein.

At a step 620, treatment input parameters are received as described herein.

At a step 622, the tissue resection profile is determined based on the input parameters as described herein.

At a step 625, the tissue resection profile is displayed on views of the organ as described herein.

At a step 627, the tissue resection profile and location are adjusted based on the images as described herein.

At a step 630, resection parameters are determined as described herein.

At a step 632, a treatment nozzle is identified from among a plurality of treatment nozzles as described herein.

At a step 633, a carrier is identified from among a plurality of carriers as described herein.

At a step 635, a fluid stream type is selected as columnar or divergent as described herein.

At a step 637, a first fluid and a second fluid are selected as described herein.

At a step 640, a treatment probe is inserted into the patient as described herein.

At a step 642, a treatment probe arm is locked as described herein.

At a step 645, an imaging probe is inserted into the patient as described herein.

At a step 650, an imaging probe is locked as described herein.

At a step 657, an imaging probe is moved in relation to the treatment probe as described herein.

At a step 660, alignment of the treatment probe with the patient is determined as described herein.

At a step 662, orientation of treatment probe is measured as described herein.

At a step 665, orientation of a treatment probe is measured as described herein.

At a step 667, the planned treatment is adjusted based on patient alignment as described herein.

At a step 668, the patient is treated as described herein.

At a step 670, tissue treated with the planned treatment is imaged and viewed as described herein.

At a step 672, the jet entrainment "fluid flame" is viewed as described herein.

At a step 675, interaction of the jet entrainment "fluid flame" is viewed as described herein.

At a step 677, additional tissue is resected based on the viewed images as described herein.

At a step 680, treatment is adjusted as described herein.

At a step 682, the elongate element and sheath are rotated amount the elongate axis to rotate the spine as described herein.

At a step 685, an angle of rotation of the elongate element and spine are measured as described herein.

At a step 687, the treatment profile is rotated around the axis based on measured angle. For example, the treatment profile can be rotate around the elongate axis of the treatment profile corresponding to the elongate axis of the elongate element and spine and sheath as described herein as described herein.

At a step 690, a portion of the organ blocked as described herein by the spine is treated.

At a step 695, treatment is completed as described herein.

Although the above steps show method 600 of treating a patient in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method 600 may be performed with the circuitry as described herein, for example one or more of the processor or logic circuitry such as the programmable array logic for field programmable gate array. The circuitry may be programmed to provide one or more of the steps of method 600, and the program may comprise program instructions stored on a computer readable memory or programmed steps of the logic circuitry such as the programmable array logic or the field programmable gate array, for example.

Figure 21A:
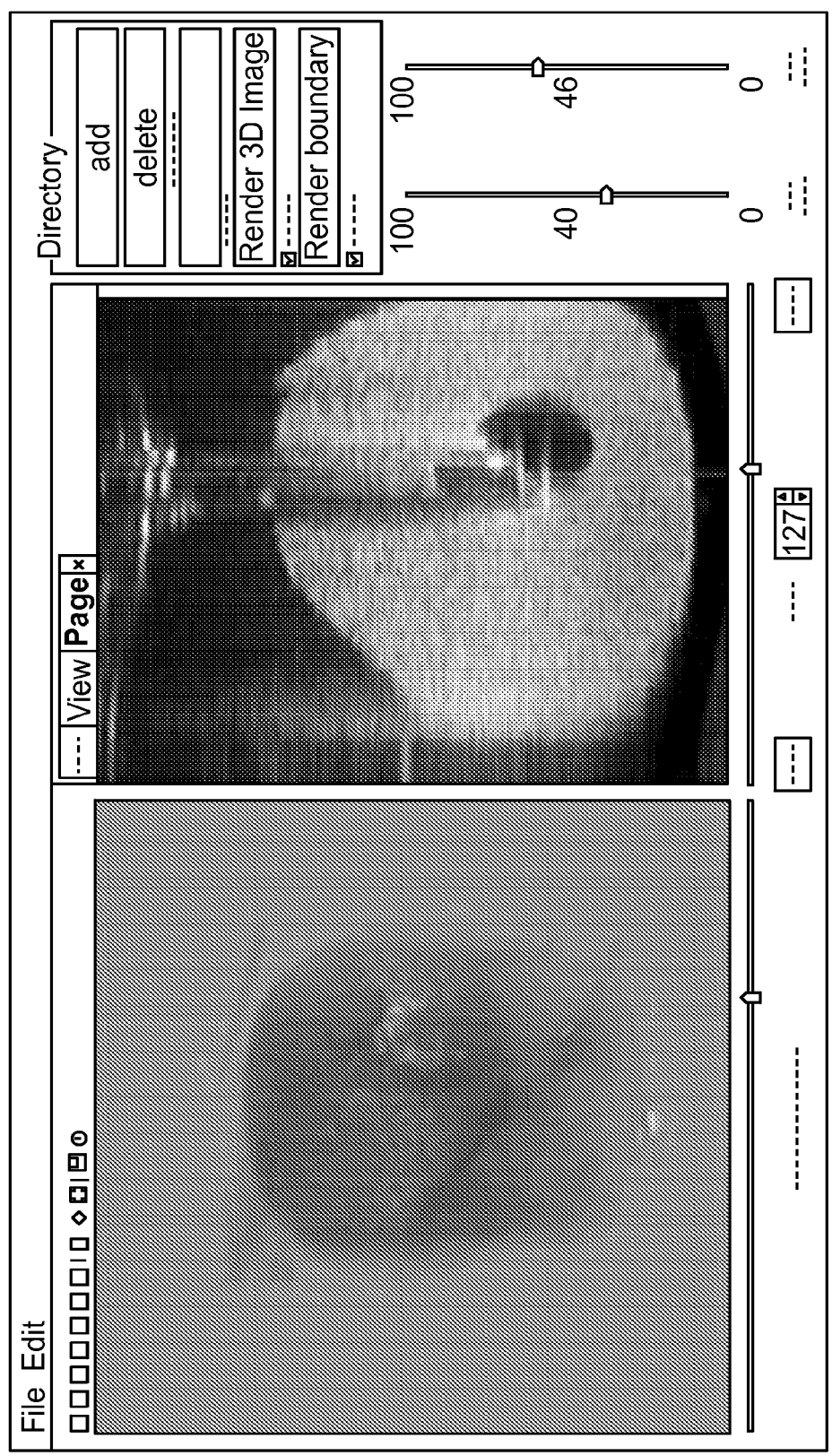
FIGS. 21A and 21B show screenshots of a 3d segmentation image used in accordance with the systems and methods of embodiments.
Figure 21B:
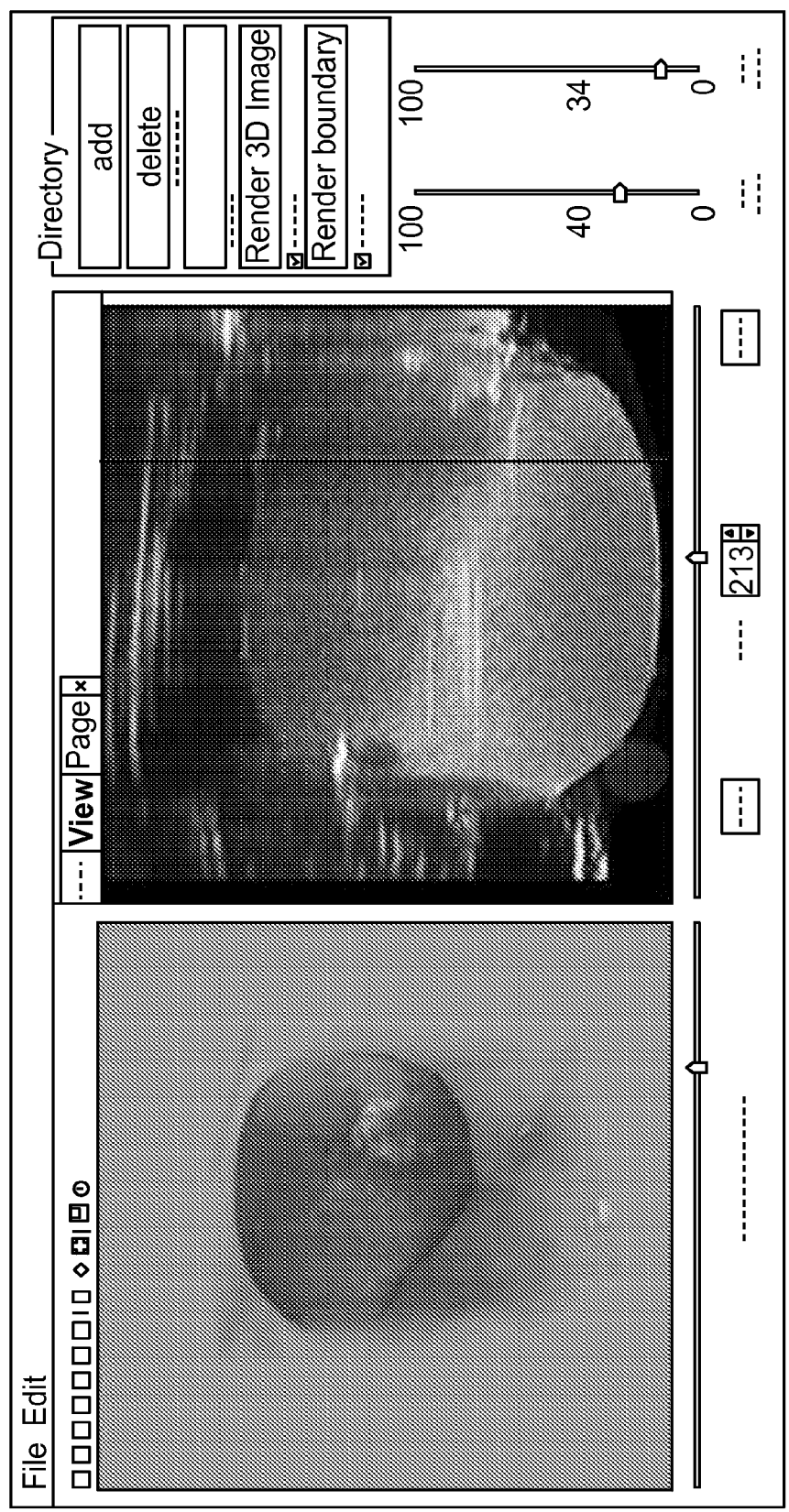
Figure 21E:
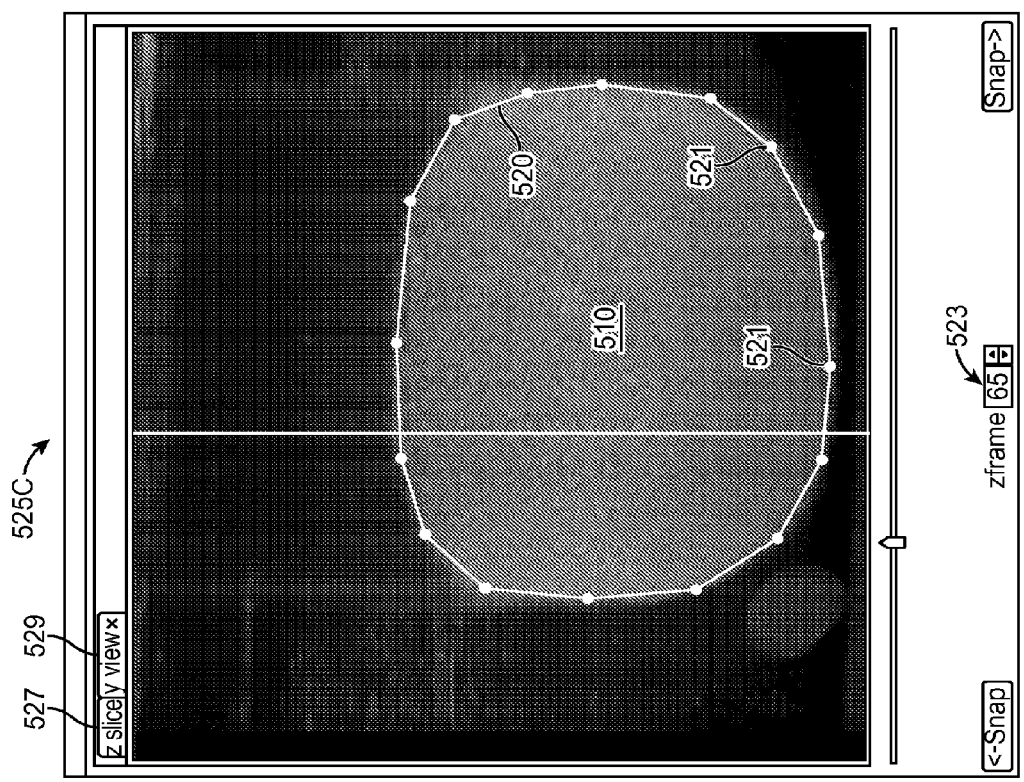
Figure 21F:
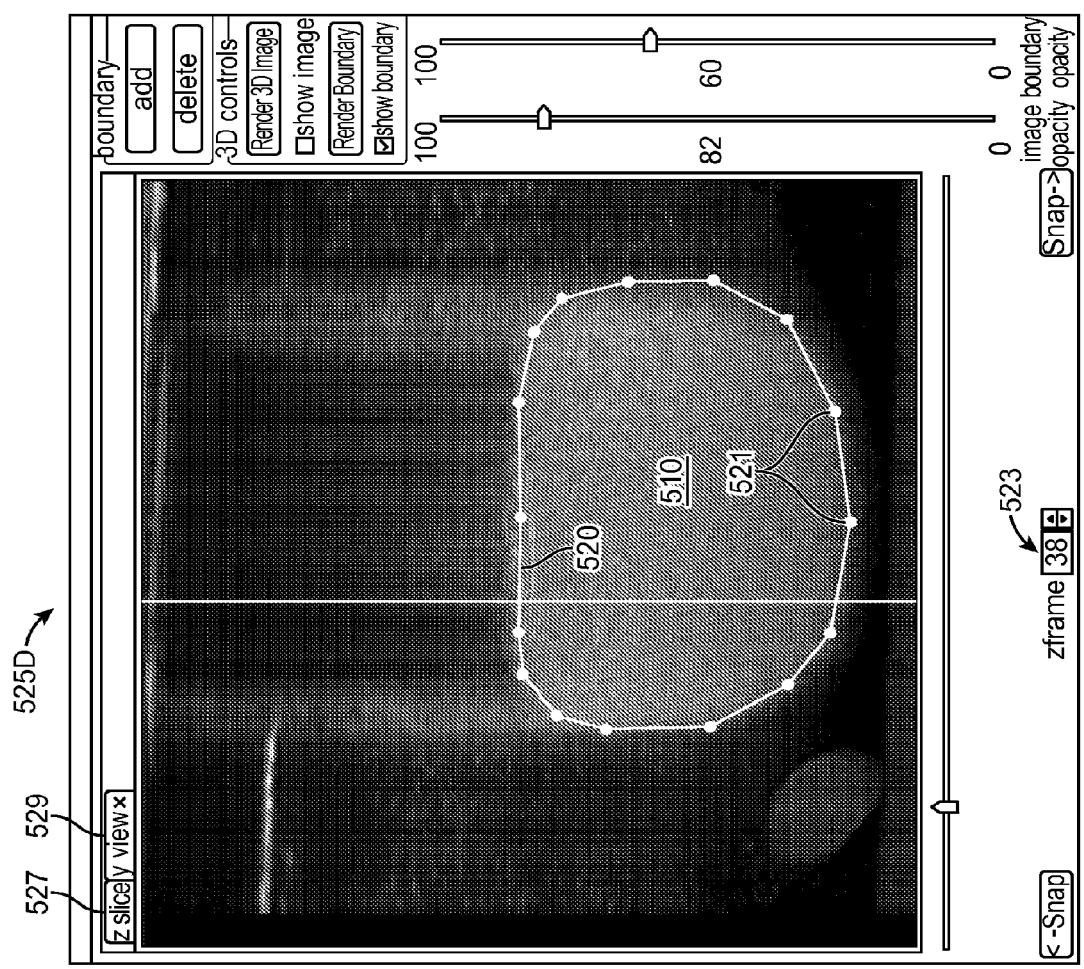

FIGS. 21A and 21B show screenshots of organ images, for example trans-rectal ultrasound prostate images, from 3D segmentation software according to embodiments of the present invention. The two dimensional images shown on the right side of FIGS. 21A and 21B, respectively. Three dimensional images of the prostate are shown on the right left of FIGS. 21A and 21B, respectively. The two dimensional images on the right side of FIGS. 21A and 21B show examples of transverse and sagittal planes, respectively, of the three dimensional prostate representations shown with the images on the left of FIGS. 21A and 21B. The transverse image may also be referred to as horizontal image, axial image, or transaxial image as described herein. Note segmentation of the sagittal plane of the prostate is depicted in light gray color, and the segmentation of the axial plane of the prostate is depicted in light gray color.

These segmented images can be provided on the display for the user to plan the treatment of the organ with images of treatment overlaid on the image of the organ as described herein, such as the treatment profiles overlaid on the image of the prostate.

The images shown in FIGS. 21A and 21B can be provided on the display 425 of interface 500. For example the axial and sagittal images can be provided on the display as described herein.

FIGS. 21C to 21F show a plurality of axial images 525 of a target tissue to define a three dimensional treatment plan and a user defined treatment profile in each of the plurality of images. The user interface comprises a first tab 527 to select a Z-slice view and a second tab 529 to select a Y-view, of a three dimensional representation of a target tissue such as an organ that may comprise the prostate. The Z-slice view may correspond to a sagittal image of the target tissue and the Y-slice view may correspond to an axial view of the target tissue. The plurality of axial images comprises a first image 525A at a first z-frame 523. The z-frame 523 may correspond to a location along an axis of the traversed by the y-slice view, and each z-frame may correspond to a location of the axial image along the z-axis. The first z-frame can be one or more of many frames.

Each image 510 comprises a user input treatment profile 520. The user input treatment profile may comprise a plurality of points that are user adjustable on the image to define the treatment profile. The first plurality of images 525A shows the treatment profile partially positioned by the user, and a plurality of treatment profile marker points 521 have yet to be placed on the target tissue location by the user. The user can adjust the location of the points with the user interface, for example with a pointing device or touch screen display. The processor as described herein comprises instructions to receive the plurality of points input by the user. The plurality of points may comprise small user movable markers such as circles, dots or X's, and the plurality of points can be connected with lines in one or more of many ways, such as with a linear interpolation corresponding to straight lines on the display or splines corresponding to curved lines shown on the display so as to connect the markers, for example.

A second image 525B of the plurality of images at a second depth is shown on the display as described herein. The second image 525B comprises points 521 aligned with the image by the user so as to define the treatment profile 520 at the second location along the z-axis corresponding to the treatment.

A third image 525C of the plurality of images at a third depth is shown on the display as described herein. The third image 525C comprises points 521 aligned with the image by the user so as to define the treatment profile 520 at the third location along the z-axis corresponding to the treatment.

A fourth image 525D of the plurality of images at a fourth depth is shown on the display as described herein. The fourth image 525C comprises points 521 aligned with the image by the user so as to define the treatment profile 520 at the fourth location along the z-axis corresponding to the treatment.

Figure 21H:
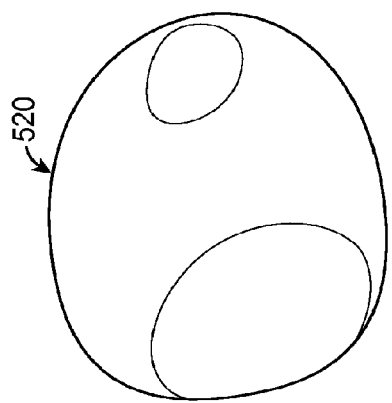
FIG. 21H shows a three dimensional treatment plan based on the plurality of images of FIGS. 21A to 21F.
Figure 21G:
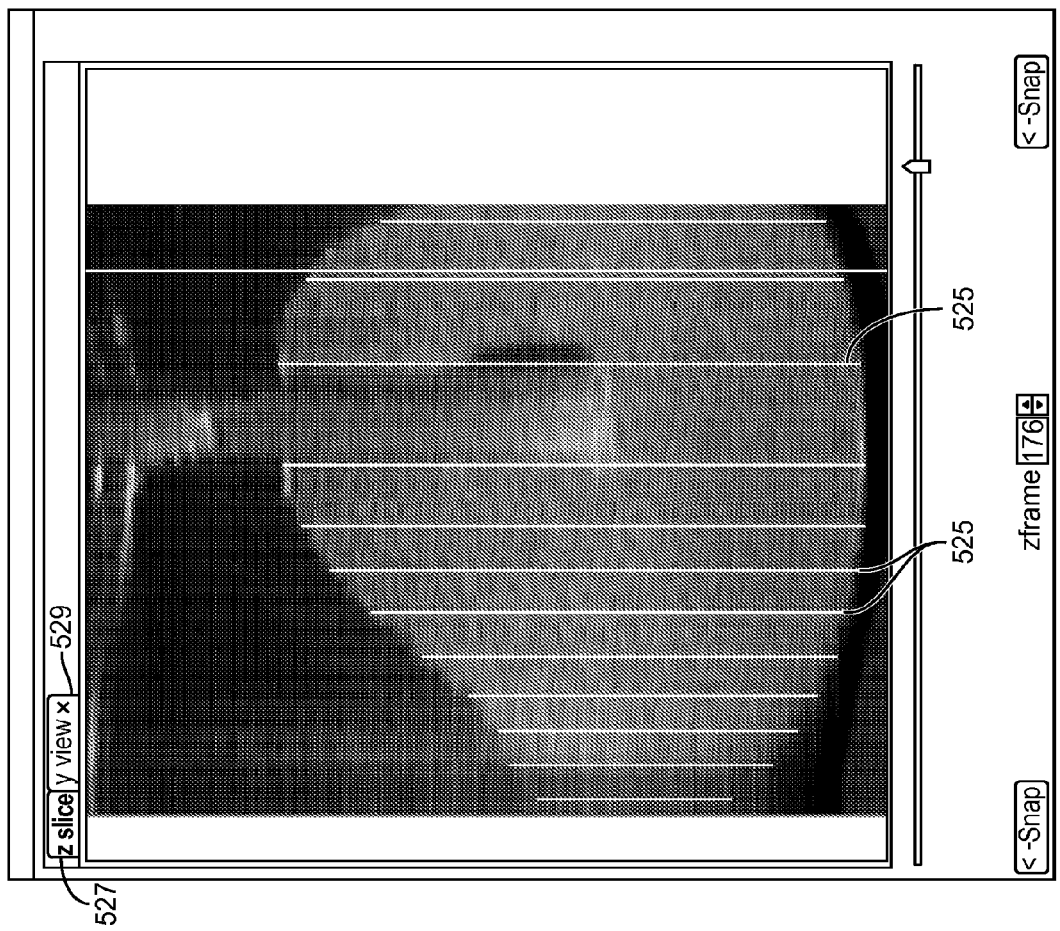
FIG. 21G shows a sagittal view of the target tissue and planes of the axial images of FIGS. 21C to 21F.

FIG. 21G shows a sagittal view of the target tissue and planes of the axial images of FIGS. 21C to 21F. The z-slice view can be selected with tab 527, so as to show a sagittal view of the target tissue. The plurality of images 525 are shown as lines extending through the sagittal view.

FIG. 21H shows a three dimensional treatment profile based on the plurality of images of FIGS. 21A to 21F. The three dimensional treatment plan may comprise a three dimensional representation of the three dimensional treatment profile 520. The three dimensional treatment profile 520 can be determined in one or more of many ways. The three dimensional treatment profile may be obtained by interpolation among the plurality of points 521 that define the treatment profile of each image, for example by linear interpolation of splines. Alternatively or in combination, the three dimensional treatment profile can be determined based on polynomial fitting to the surface points 521, for example.

Figure 21I:
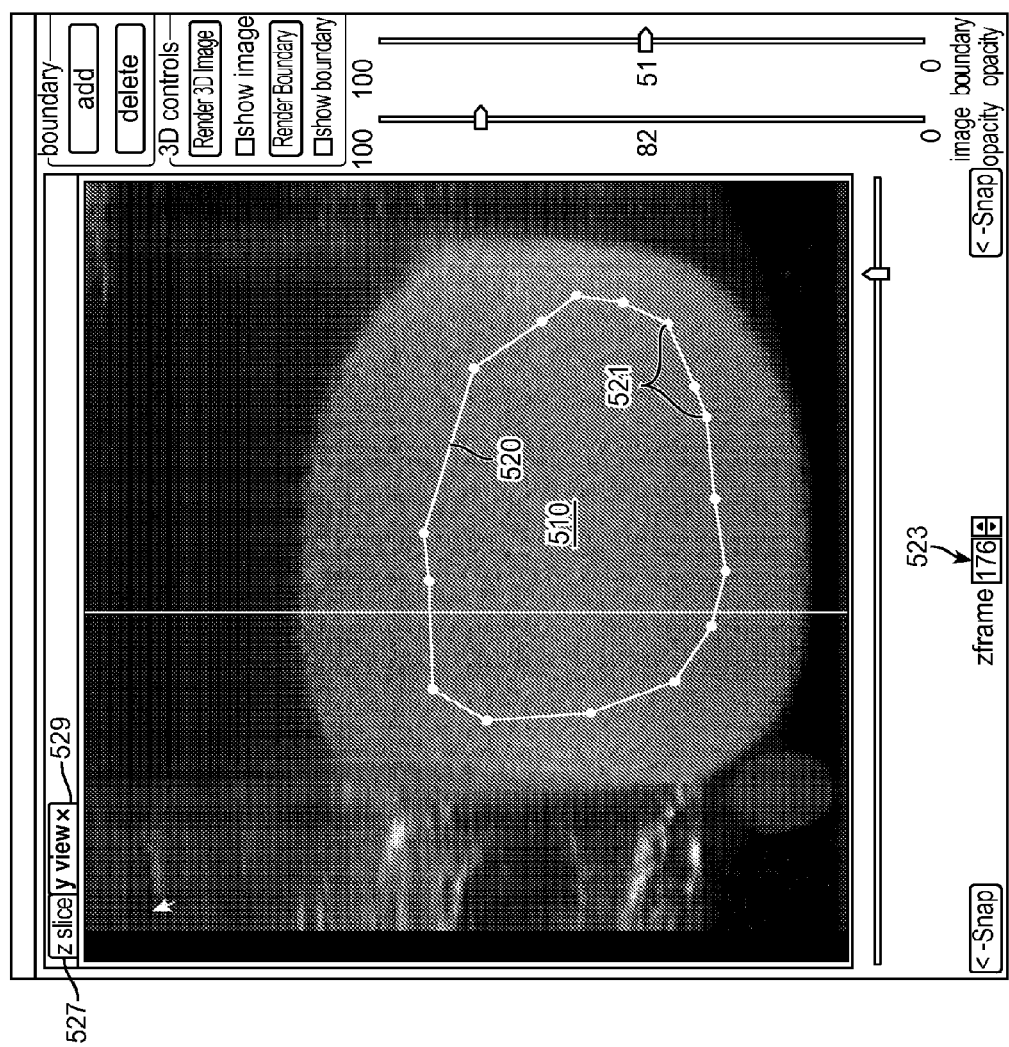
FIG. 21I shows a user input treatment profile of an image among a plurality of images.

FIG. 21I shows a user input treatment profile of an image among a plurality of images as described herein. The user can adjust the plurality of points 521 in one or more of many ways, and the user can determine the treatment profile based on patient need. The treatment profile can be selected so as not to extend to an outer boundary of a tissue structure, for example an outer structure of an organ such as a prostate as shown in FIG. 21I.

Figure 21J:
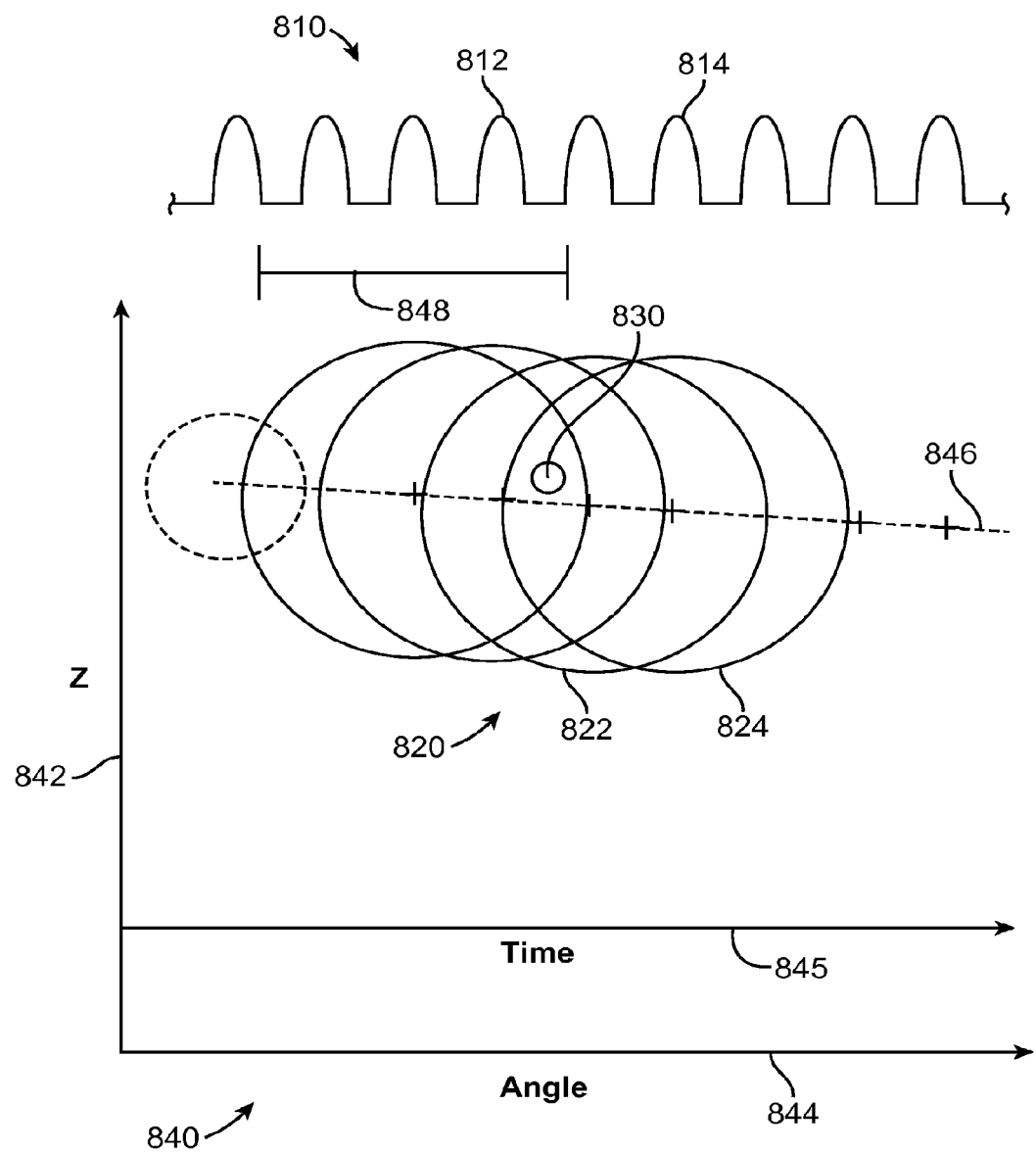
FIG. 21J shows scan patterns of the fluid stream, in accordance with embodiments.

FIG. 21J shows scan patterns 840 of the fluid stream as described herein. The fluid stream may comprise a pulsed or continuous fluid stream. The scan pattern can be based on critical pressures as described herein so as to remove a first tissue and inhibit removal of a second tissue. In many embodiments, the fluid stream comprises a plurality of pulses 810 from a pump such as a piston pump, and the pulses comprise a frequency and duty cycle. In many embodiments, the duty cycle corresponds to no more than about 50%. The plurality of pulses 810 comprises a first pulse 812 and a second pulse 814. The fluid flame may comprise an approximate cross sectional size at the location of tissue being scanned. Based on the teachings described herein, a person of ordinary skill in the art will recognize that the fluid flame comprises a maximum cross sectional width at about 1 h the length of the fluid flame. At the location where the fluid flame impinges upon tissue, the fluid flame comprises a cross sectional size 848.

The scanning pattern of the fluid stream comprising the fluid flame are along a Z-axis 842 and angle 844. The angle 844 may correspond to time 845, for example when the angular sweep rate remains substantially constant. The fluid flame is scanned along a scan path 846. The scan path 846 may correspond to the velocity of the carrier 382 along the Z-axis and the rotation of the carrier 382 around the Z-axis, for example.

The pulses can be spaced apart such that a plurality of sequential pulses strike a location 830 of tissue. The plurality of sequential pulses can be effective in removing a first type of tissue when removal of a second type of tissue is inhibited.

Alternatively or in combination with the critical pressures as described herein, work in relation to embodiments suggests that the rate of removal can be related to a relaxation time of a targeted tissue. The fluid flame can be configured to dwell on a point 830 of tissue for a duration longer than the relaxation time of the tissue, such that the tissue can be deformed beyond a threshold and removed.

In many embodiments, the plurality of pulses 820 impinge upon the tissue location 830 with a duration between pulses 822, 824 that is less than a tissue relaxation time of elastic deformation of the tissue so as to remove the tissue. In many embodiments, a first tissue to be removed comprises a first relaxation time greater than the time between pulses, and the second tissue for which removal is to be inhibited comprises a second tissue relaxation time less than the time between pulses, so as to inhibit removal of the second tissue.

As the tissue is removed toward the final desired treatment profile, the size of the fluid flame may decrease substantially near the distal tip of the flame, such that the size of the pulsed fluid flame impinging upon the resected profile is decreased substantially tissue removal decreased substantially.

Based on the teachings described herein, a person of ordinary skill in the art can determine the scanning movement of the carrier 382 and nozzle to resect tissue to a target profile with the fluid flame as described herein.

Figure 21K:
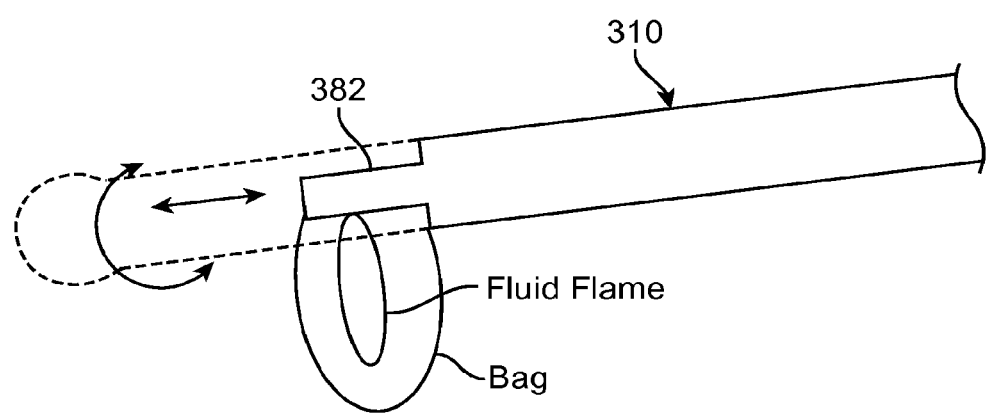
FIG. 21K shows a bag over a fluid stream comprising a water hammer in accordance with embodiments.

FIG. 21K shows a bag over a fluid stream. The fluid stream may comprise the columnar stream or divergent stream as described herein. In many embodiments the bag is placed over a fluid stream comprising a pulsed stream so as to comprise a water hammer. The bag can be made of one or more of many materials and may comprise an elastomer, for example. The interior of the bag can be coupled to the carrier 382, and the exterior of the bag can be coupled to the working channel to remove material. The bag has the advantage of protecting the tissue from the high fluid flow rate and can provide more even pressure. The fragmented tissue can be collect through passive or active means, for example through an outer collection tube or the working channel.

Figure 22A:
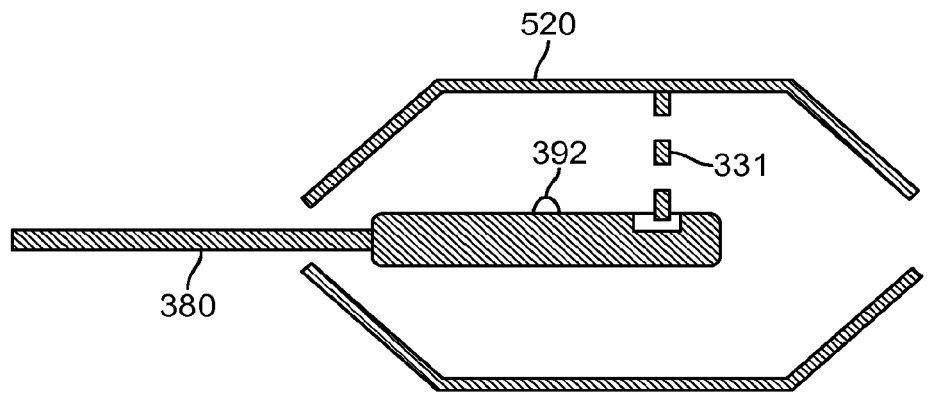
FIGS. 22A and 22B show schematic illustrations of a probe being operated in accordance with the principles of embodiments.
Figure 22B:
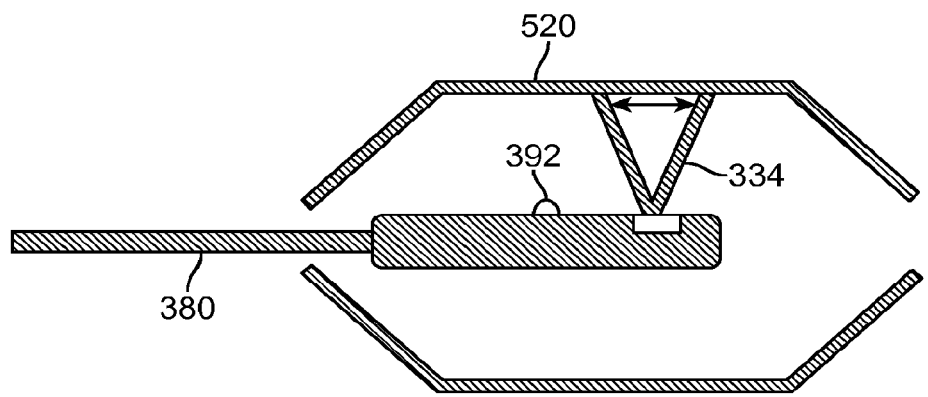

FIGS. 22A and 22B show schematic illustrations of a probe being operated in accordance with the principles of embodiments as described herein, so as to provide a real time determination of the tissue removal profile 520. FIG. 22A shows columnar fluid stream 331 and FIG. 22B shows diverging stream 334, each of which is suitable for combination with the image guided tissue resection as described herein.

Interstitial laser-guided 3D imaging (inside tissue and/or inside an organ with or without fluid and with or without a water jet): employ the spot from the laser on the inner surface of the prostate to determine the depth of a cut. That is, knowing the axial and rotational position of the nozzle, and given that the spot lies on a radius from the nozzle, locating the spot in the image from the camera gives a unique spot-to-nozzle distance. Scanning the laser, and using image processing to find the spot, a full image of the volume inside the prostate can be produced. Combining this with the organ geometrical data, the volume resected can be displayed within the organ in 3D. Alternatively, using the laser to measure the distance between itself and the target surface, an exact three-dimensional replica of the area it has scanned can be recreated.

Acoustic Distance Measurement.

By placing an acoustic transducer in the assembly near the water jet it will be possible to measure distance along the water jet to the tissue plane struck by the jet. Scanning the jet then allows three-dimensional mapping of the cavity. At least one transducer 392 can be provided on the carrier tube 380. Interstitial sound-guided tissue differentiation (inside tissue and/or inside an organ in fluid/gas environments): the audible frequencies produced by the jet-tissue interface can allow for differentiation of tissue. Monitoring the acoustic behavior at this interface may add a depth monitoring feature to the system; this can enhance safety as to prevent the jet from penetrating the prostate's capsule. The sensor could be attached to the tip or anywhere along the probe/sheath's shaft.

Pulse width modulation of the water column: modulating the frequency at which the water is on and off can allow the user to estimate the distance of nozzle to tissue under camera visualization. The frequency can be fixed to a predetermined column size (e.g. 5 mm) or user could adjust it to match the height between the nozzle and tissue, as shown in FIG. 22A. Alternatively, the diameter of the jet at the jet-tissue interface can determine distance from nozzle assuming the high pressure divergence characteristics of the nozzle is defined as shown in FIG. 22B.

The at least one transducer 392 may comprise an acoustic transducer to receive acoustic signals from the tissue. In some embodiments, at least one transducer 392 transmits acoustic signals for ultrasound imaging. The at least one transducer may comprise a plurality of transducers. A second acoustic transducer can be provided on carrier tube 380 to one or more of receive or transmit acoustic signals for ultrasound imaging from the probe to the tissue. The at least one transducer 392 may comprise an ultrasound array to provide axial and transverse imaging as described herein, for example.

Figure 22C:
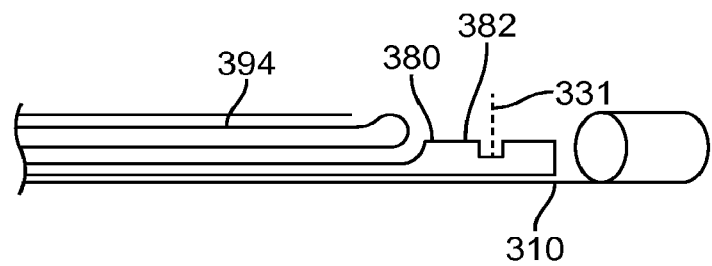
FIG. 22C shows an endoscope placed in the working channel of elongate element with carrier to image tissue when the patient is treated in accordance with embodiments.

FIG. 22C shows an endoscope 394 placed in the working channel of elongate element 310 with carrier 382 to image tissue. The endoscope 394 can be used to image the tissue profile as described herein. For example, a fluid stream can be used to illuminate the tissue with laser pointing with the fluid stream, for example columnar fluid stream 331. The known angle and axial location of the fluid stream can be used with the location of the image from the endoscope to determine the surface profile of the tissue.

Figure 23A:
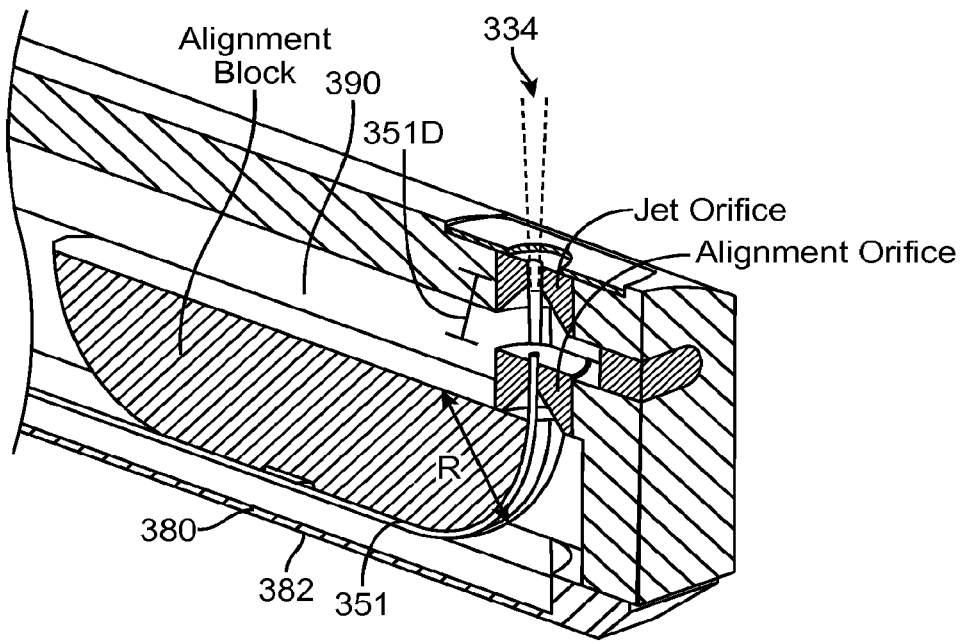
FIGS. 23A and 23B show a carrier configured to provide integrated jet delivery in accordance with embodiments.
Figure 23B:
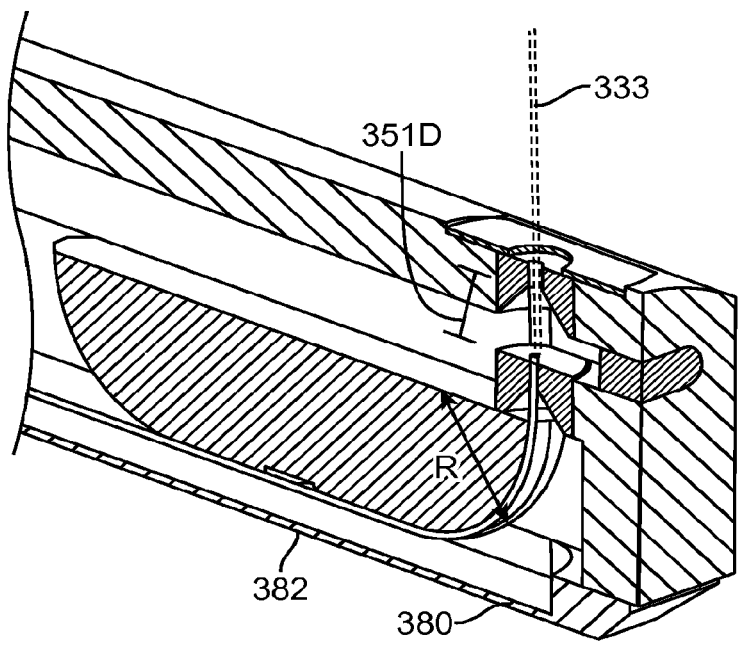

FIGS. 23A and 23B show a carrier configured to provide integrated jet delivery. The carrier 382 that may comprise carrier tube 380 comprises an energy delivery conduit 351, such as an optical fiber. An alignment block is provided to align the optical fiber with the fluid delivery element. The optical fiber can be bent to provide a bend angle suitable for delivery of optical energy to the end of the optical fiber.

The configuration of the optical fiber, jet orifice and alignment orifice provide the integrated jet capability. The jet orifice can be formed in a nozzle that comprises an inverted solid conic section that defines a conic channel to receive the fluid to form the fluid stream and to receive light from the optical fiber. The alignment orifice can be formed in an alignment structure and comprises an inverted solid conic section that defines a conic channel to receive the fiber and the conic channel extends to a cylindrical channel having a diameter sized to receive the optical fiber. In many embodiments, the conic channel comprises of the alignment orifice comprises an angle to receive the fiber such that the fiber can be advanced along the conic channel and through the cylindrical channel without damaging the optical fiber. In many embodiments, the optical fiber, including the cladding, comprises a diameter less than the cylindrical channel of the alignment orifice, such that the optical fiber can be advanced along the cylindrical section without damaging the fiber. The flat section of the alignment block can hold the fiber to inhibit movement of the fiber along the longitudinal axis of the fiber when the tip of the fiber is held in alignment with the cylindrical portion of the jet orifice channel.

The nozzle comprising the jet orifice and the alignment structure comprising the alignment orifice may each comprise a jewel having the conic section and cylindrical section as described herein.

In many embodiments, the cylindrical channel portion of the alignment orifice holds the optical fiber in alignment with a gap extending around at least a portion of the optical fiber. The cylindrical channel portion of the alignment orifice extends along an axis a sufficient distance so as to align the optical fiber with the jet orifice with the gap extending between the fiber and the cylindrical channel portion of the alignment orifice along at least a portion of the fiber and the cylindrical channel portion.

The jet orifice and alignment orifice are spaced apart axially a sufficient distance such that the fluid that passes through the jet orifice can deliver a fluidic stream of energy with predictable flow, for example so as to form the columnar stream with low pressure and the divergent cutting stream with high pressure. In many embodiments, a distance 351D extends between an upper surface of the structure defining the cylindrical channel portion of the alignment orifice and the lower end of the cylindrical channel of the jet orifice. Distance 351D is dimensioned such that the light beam emitted from the optical fiber diverges so as to allow energy transmission of at least about 80% through the jet orifice, for example at least about 90% through the alignment orifice, and such that the predictable flow can be provided. In many embodiments, the distance 351D is within a range from about 200 um to about 2.5 mm, for example within a range from about 0.5 mm to about 2 mm, for example.

An alignment block is coupled to the optical fiber, and the alignment block comprises a surface to engage the optical fiber in which the fiber engaging surface comprises a radius of curvature which can be less than 5 mm, for example no more than 2 mm, so as to allow the cross sectional dimensions of the tip of the carrier 382 to be sized to pass through the working channel with rapid exchange as described herein.

The alignment block can engage the optical fiber so as to retain the optical fiber. The curved engagement surface of the alignment block engages the optical fiber and retains the optical fiber in position. The lower engagement surface of the block also comprises a substantially non-curved elongate channel portion proximal to the curved portion to engage the fiber and fix the location of the fiber within the probe, for example by holding the fiber between the block and an upper surface of the lower portion of the carrier 382.

The fluid jet can be used at high pressure for ablation, for example, a fluid jet, or low pressure, for example, columnar for transmitting an optical beam. The optical fiber can be bent, guided and aligned by positioning the alignment block and alignment orifice to achieve a desired alignment. A short and tight bend radius can be achieved by positioning and fixing the optical fiber in this manner. Cavitation and other fluid jet effects can be altered by varying the relative position and orientation of the jet alignment orifices.

The fluid stream released from the fluid delivery element may comprise a diverging stream 334 as shown in FIG. 23A or a columnar stream 333 as shown in FIG. 23B. The diverging stream 334 can be provided by providing a higher pressure to the delivery element. At high pressure the fluid jet will diverge, for example when the first fluid is a liquid and the second fluid is a liquid. Alternatively a low pressure can be provided to provide the columnar stream 333 as shown. The columnar stream 333 can be provided when the fluid released is a liquid and the liquid is released into a gas, and the liquid can be released with a low pressure within a range from 2 to 100 psi, for example within a range from 5 to 25 psi. At the low pressure the columnar fluid comprising the columnar stream 333 can be used as a pointing device to point the laser beam for alignment. Alternatively or in combination the columnar fluid stream can be used to heat tissue, for example, to heat with one or more of ablation, vaporization, or coagulation, for example.

The diverging stream 334 can be provided by increasing the pressure to the nozzle for tissue removal with the divergent stream as described herein. The optical fiber of the carrier 382 that may comprise carrier tube 380 can be bent to provide a narrow profile configuration of the carrier 382. For example, the optical fiber can be bent with a radius within a range from about 1 to 10 mm, for example, within a range from about 2 to 5 mm. This bending of the optical fiber can allow the light energy to be released and transmitted with high efficiency from a light source to the desired tissue target. Also the terminal end of the optical fiber can be aligned such that light emitted from the optical fiber is substantially directed through the channel defined with the nozzle that delivers the fluid stream. An alignment structure comprising an alignment orifice can be used to align the optical fiber with the jet orifice of the fluid delivery element.

Figure 24:
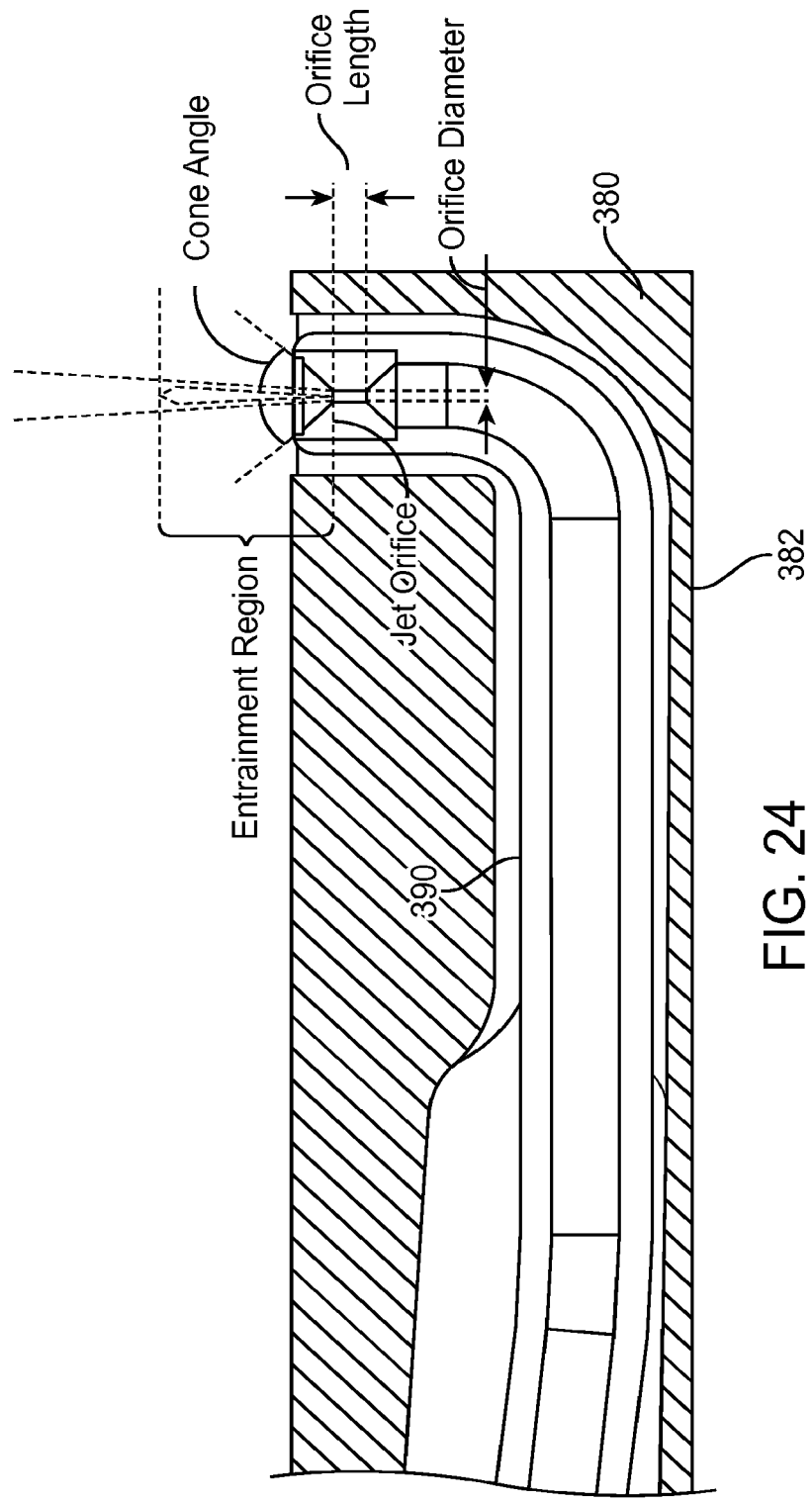
FIG. 24 shows carrier comprising a fluid delivery element and design considerations of the fluid delivery element, in accordance with embodiments.

FIG. 24 shows carrier 382 comprising a fluid delivery element and design considerations of the fluid delivery element. The jet orifice design of the fluid delivery element can be configured in one or more of many ways. Fluid jet ablation characteristics can be varied by varying the jet orifice geometry. For example cone angle variation will result in an increase or decrease in cavitation occurring at the nozzle exit. The jet orifice design may comprise a cone at one or more of the entrance or the exit of the orifice. The cone angle can vary from 0 to 180 degrees, for example. The orifice diameter and orifice length variation can result in a variation in nozzle back pressure and exit speed of the fluid stream. The resulting entrainment region varies with each of these parameters. The entrainment region may comprise a cloud of cavitation bubbles generated by the nozzle. The depth of tissue penetration can be predicted and controlled based on the entrainment region length. In many embodiments the entrainment region can be visualized with ultrasound imaging or optical imaging in combinations thereof. The entrainment region corresponds to a region where cavitation occurs, which allows the entrainment region to be visualized and can be referred to as a fluid flame. The cool cutting of the entrainment region can allow for tissue removal with minimal tissue damage. In many embodiments the cone angles within a range from about 40 degrees to about 80 degrees. A ratio of the orifice length to the inner diameter of the orifice can be within a range from about 1 to 10, for example, within a range from about 4 to 7. A person of ordinary skill in the art can design a jet orifice to treat tissue as described herein based on the teachings provided herein.

Figure 25A:
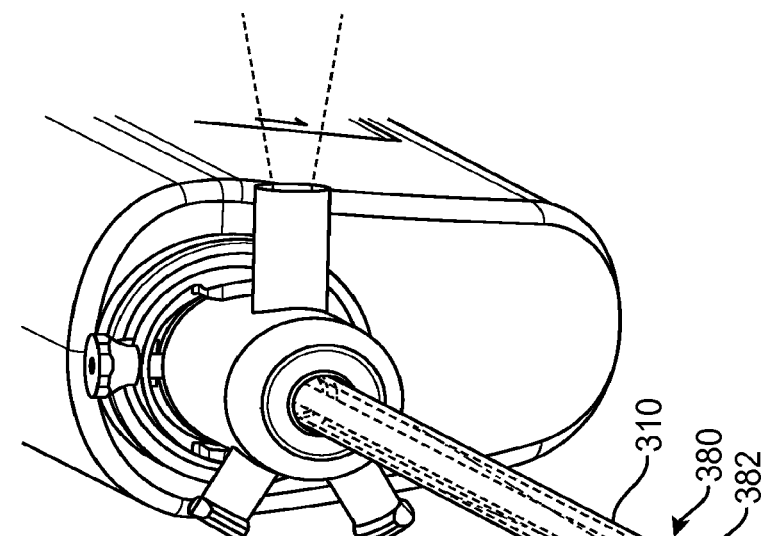
FIGS. 25A through 25C show jet deflection in accordance with embodiments.
Figure 25B:
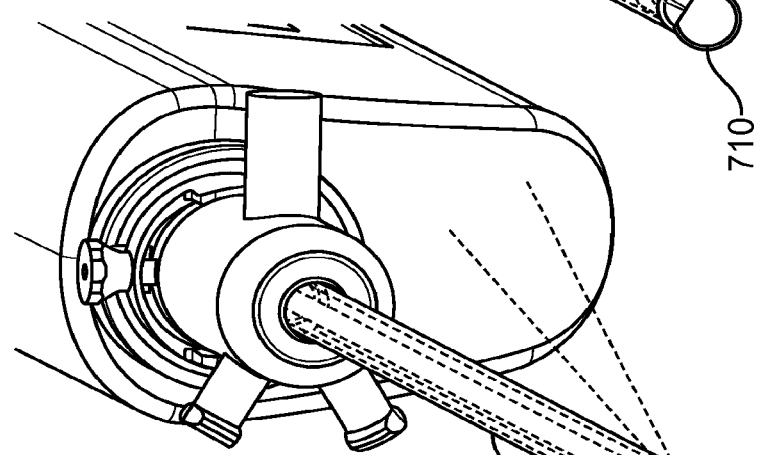
Figure 25C:
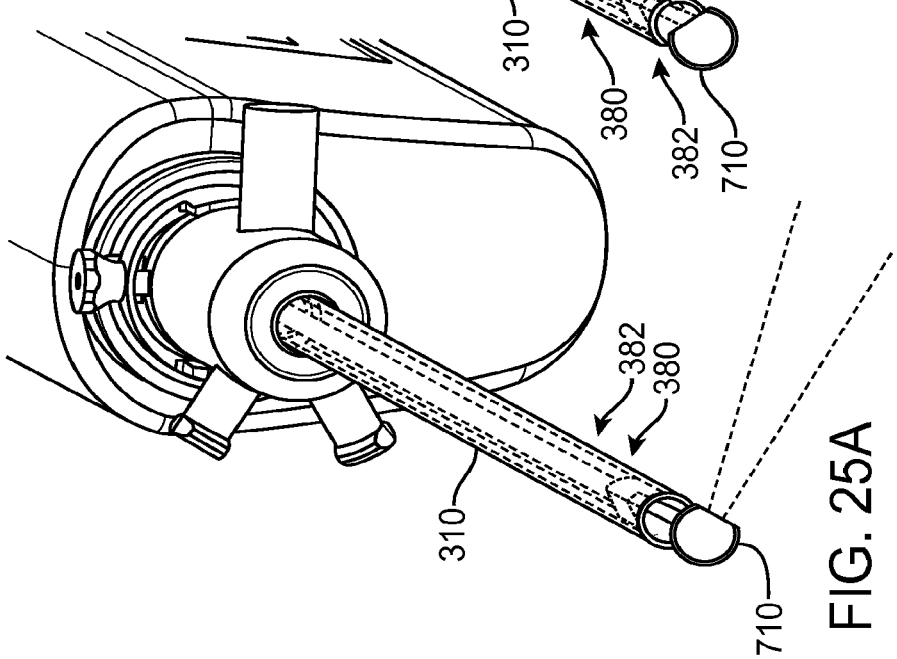

FIGS. 25A through 25C show jet deflection in accordance with embodiments. A deflector 710 can be provided on the distal end of carrier 382. The jet deflection can be achieved in one or more of many ways. The fluid jet can be deflected to achieve different cutting angles, for example. Alternatively or in combination, deflected or diverted fluid jets can be utilized to clean the working channel and auxiliary devices, for example. Deflection of the fluid stream can be actuated manually or robotically via pull wires, pneumatics, hydraulics, mechanical links and other means, for example. The deflector can be moveable under computer control and the deflector may comprise a gimbal to vary deflection of the fluid stream with respect to the longitudinal axis of the carrier 382. FIG. 25A shows deflection of the fluid stream to a first angle in relation to the longitudinal axis. And FIG. 25B shows deflection of the fluid stream at a second angle to the longitudinal axis. FIG. 25C shows rotation of the fluid stream around the longitudinal axis with the fluid stream deflected at the second angle.

FIGS. 26A through 26C show jet masking in accordance with embodiments. Fluid jet masking can be used to achieve different cutting areas, for example in a single location or multiple locations. A masking mechanism can be actuated manually or by robotically via pull wires, pneumatics, hydraulics, mechanical links and other means, for example. In many embodiments a hypo tube extends along carrier 382 so as to allow shaping of the mask on the distal end of the carrier 382. A mask 720 comprises a first configuration 722 as shown in FIG. 26A. As shown in FIG. 26B, mask 720 comprises a second configuration 724 in which the mask has been adjusted to provide a wider angle of the release fluid stream. FIG. 26C shows a third configuration 726 of the mask.

The mask embodiments as described herein can allow rotation of the mask around the longitudinal axis for angles of rotation greater than 360 degrees. For example, a plurality of rotations can be used. The plurality of mask configurations can allow sculpting of the target tissue to a desired intended profile and can allow rapid removal of the tissue with sweep rates that allow a smooth profile to be provided. The shape of the mask can allow for bulk tissue removal with a large divergence angle for tissue proximate to the mask. For tissue farther from the mask the angle may be decreased so as to provide decreased divergence of the jet to reach tissue at a location farther from the mask.

Figure 27B:
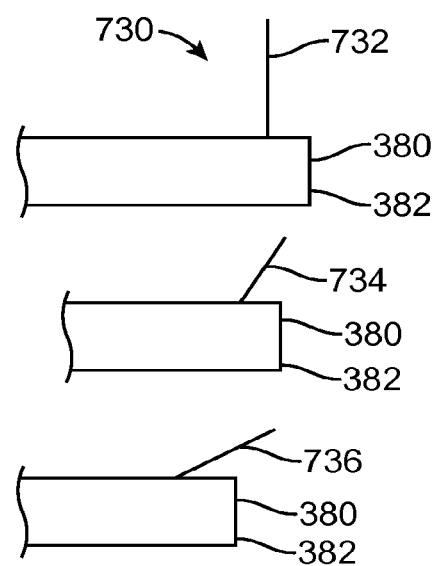

FIGS. 27A and 27B show variation of jet angle in accordance with embodiments. The fluid jet angle and the laser beam can be fixed at different angles to achieve cutting or coagulation. The one or more of cutting or coagulation can be directed to a single location or multiple locations, for example. Angling can assist in targeting tissue near an expandable anchor such as a balloon or reduce risk of incidental contact with unintended tissue. The jet angle can be varied in one or more of many ways. For example, a plurality of carriers 730 can be provided, and each of the carriers may comprise carrier 382 having structures and components for treatment as described herein. Each of the plurality of carriers 730 can provide a different fluid stream angle. For example, a first carrier can provide a first angle 732. A second carrier can provide a second jet along the second angle 734 and a third carrier can provide a third angle 736 as shown. The plurality of probes may comprise a set of probes, for example, three or more probes in which each probe is configured to direct one or more of the jet angle or the laser beam at an angle. For example, first angle 732 can extend substantially perpendicular to the elongate axis and third angle 736 can be directed toward a distal end of the probe in order to resect medial tissue, for example tissue of the prostate.

In many embodiments, a plurality of probes can be provided in which one or more jets exits the device axially to target tissue immediately distal of the device.

Figure 28:
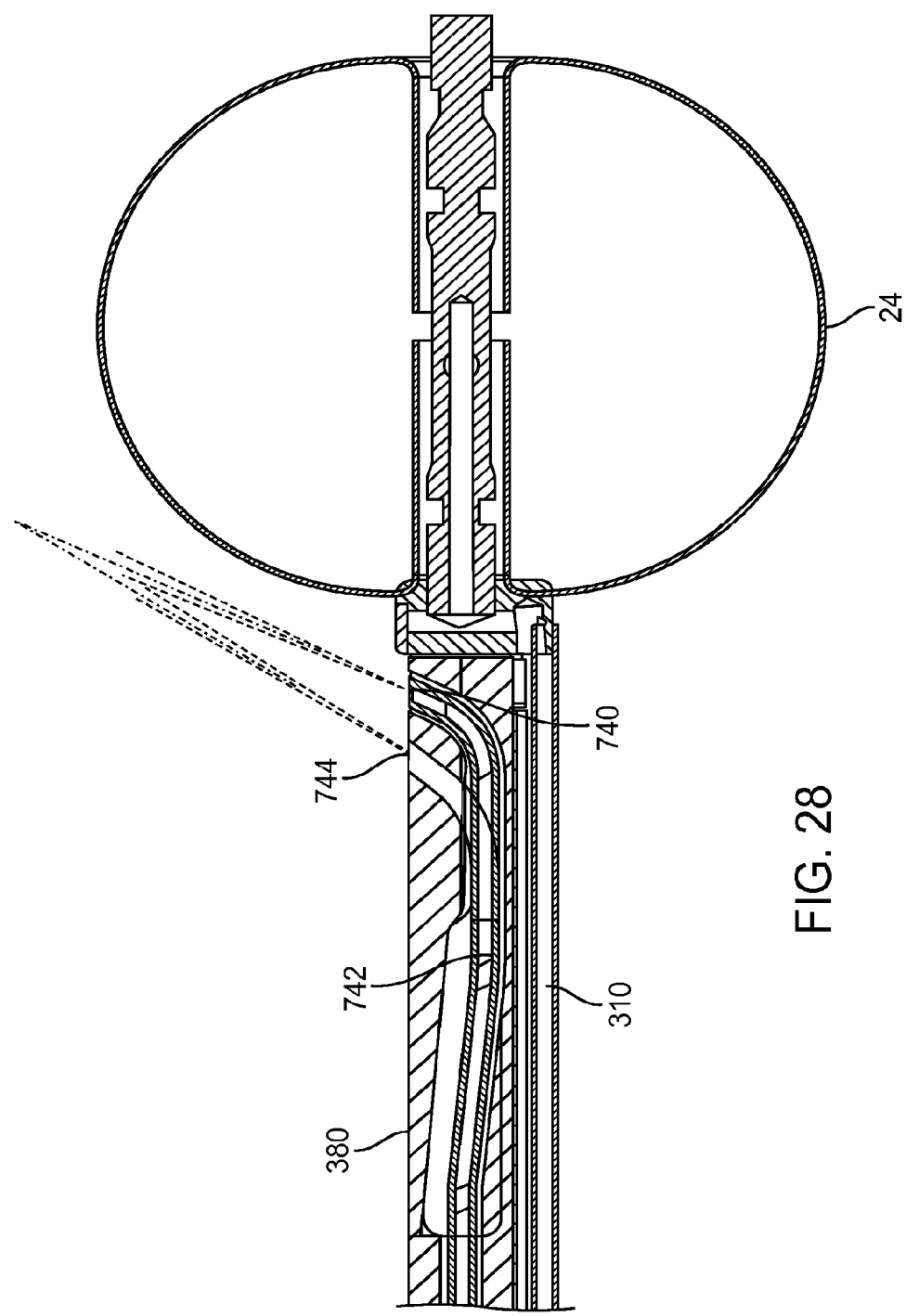
FIG. 28 shows multiple jets delivered simultaneously in accordance with embodiments.

FIG. 28 shows a plurality of jets delivered simultaneously in accordance with embodiments. The plurality of jets of carrier 382 may comprise a primary jet 740 and a secondary jet 744 connected with the supply channel 742. The supply channel 742 may comprise a common supply channel.

Multiple jets can be employed to achieve concurrent ablation and coagulation. This can be achieved through the use of a single supply channel or multiple supply channels. In the case of a single supply channel, a small amount of pressure can be bled off to feed the secondary jet. Additionally, a low power source laser pointer can be utilized for the secondary jet to assist in tissue targeting while using the primary jet for ablation.

In many embodiments, the secondary jet can be used to direct a light beam to coagulate tissue and the primary jet can be used to clear tissue away while the secondary jet is utilized as a wave guide.

In many embodiments, the primary jet can be used to debride tissue while secondary jet is used to coagulate tissue.

Figure 29:
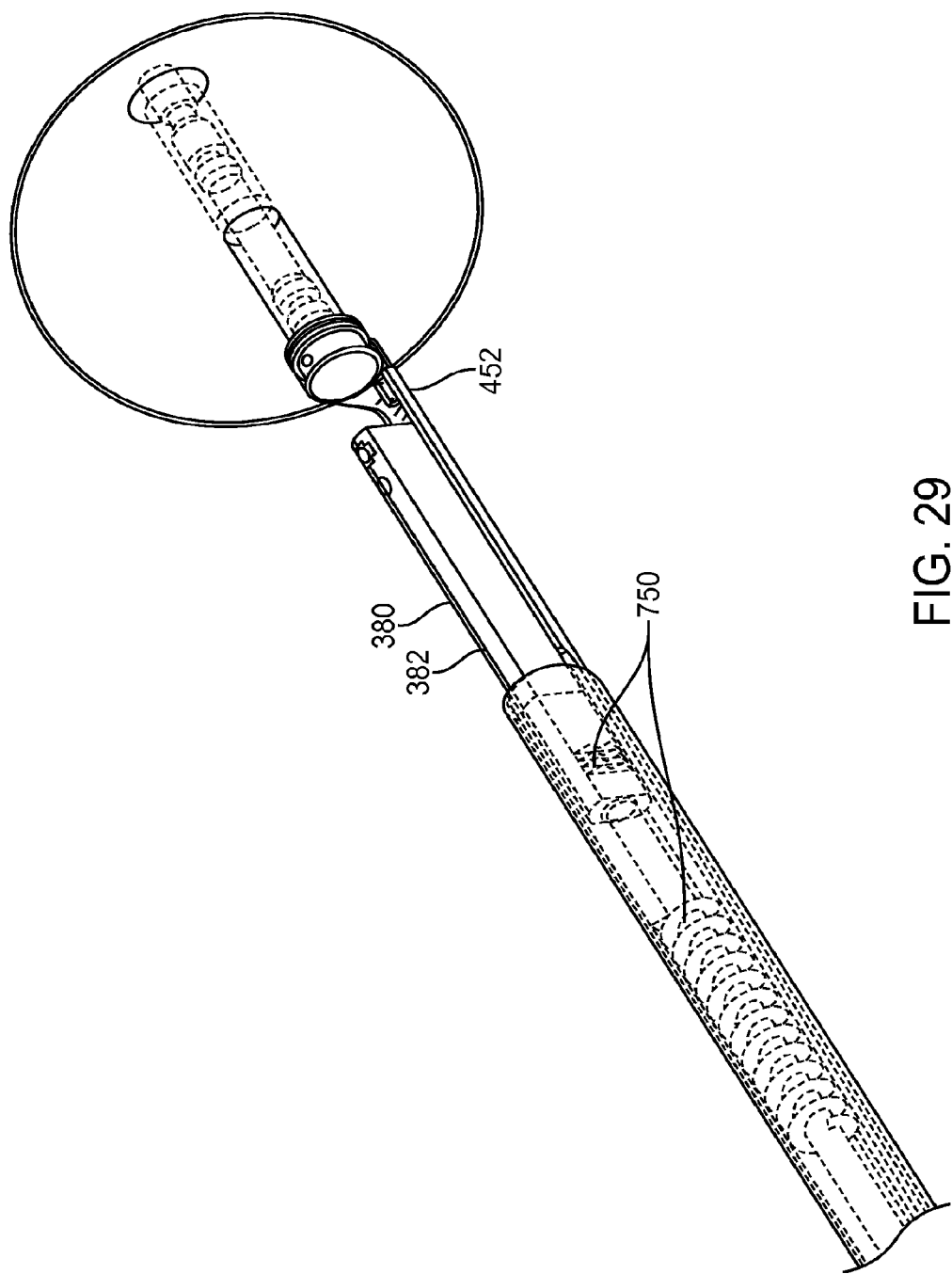
FIG. 29 shows morcellation in accordance with embodiments.

FIG. 29 shows morcellation in accordance with embodiments. In many embodiments, morcellation can be achieved concurrently with ablation with structural features 750 such as blades on the probe or spine for example. If integrated to the probe, morcellation can be automatically driven by the movement of the probe. Vacuum suction can be used alongside or independently with physical morcellation to increase collection flow. The combination of physical morcellation for example with an auger structure and vacuum can be utilized to regulate intraorgan pressure.

Carrier 382 can extend to a distal end portion having one or more jets as described herein. Morcellating features can be provided proximately with respect to the jets and the morcellating features may be contained within the working channel, for example, with an auger shaped structure to remove tissue.

Figure 30:
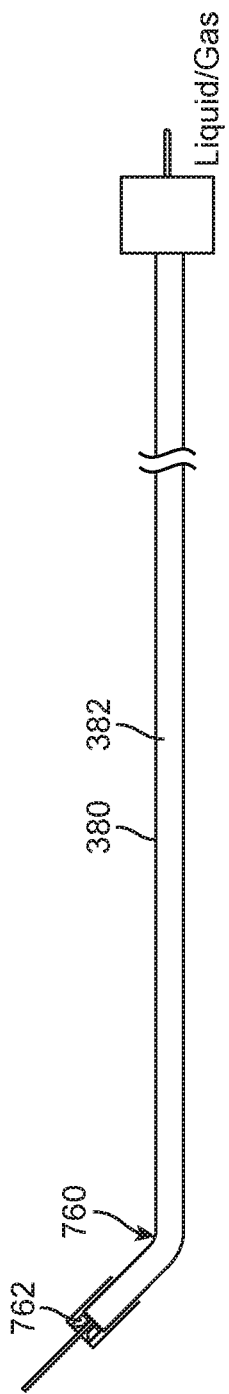
FIGS. 30 to 31B shows single tube designs in accordance with embodiments.
Figure 31A:
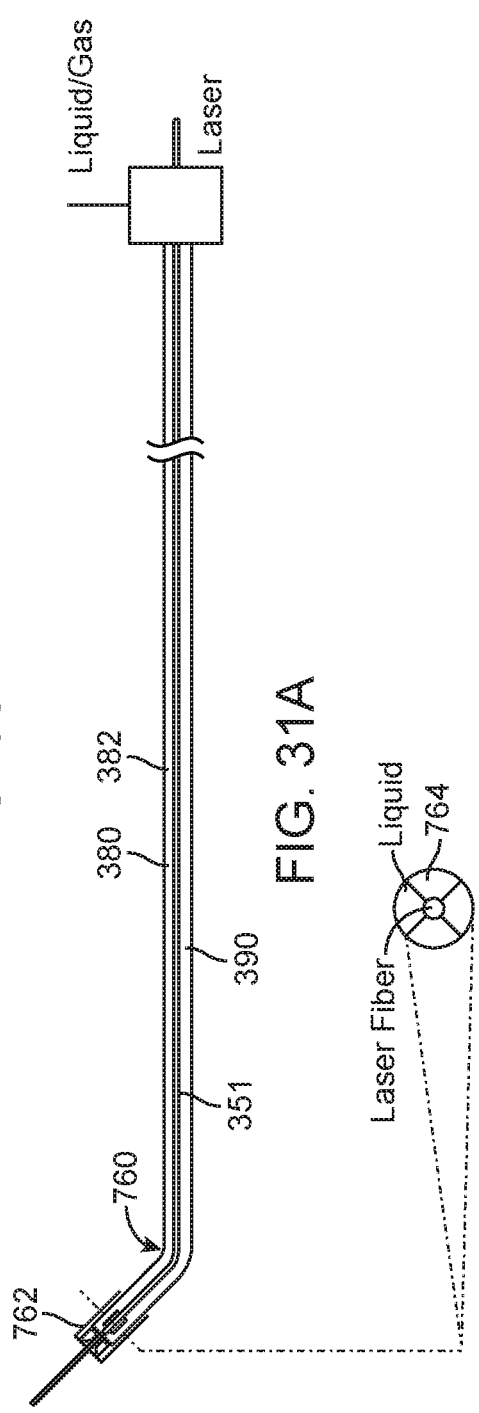
Figure 31B:
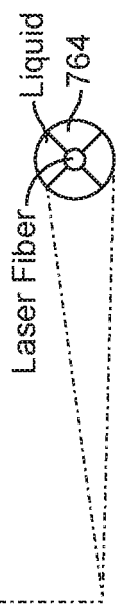

FIG. 30 shows a single tube design in accordance with embodiments. The single tube design may comprise a fluid delivery element such as an orifice jewel 762. A variable bend 760 allows a radius to bend, for example, when the carrier 382 is advanced within the working channels. A fluid is coupled to the orifice on the end of the carrier 382. The fluid may comprise liquid or gas and the orifice on the distal end can be configured in one or more of many ways as described herein. FIGS. 31A and 31B show a single tube design in accordance with embodiments. A fluid such as a liquid or gas can be coupled with a laser as described herein. The laser can emit electromagnetic energy transmitted along an energy conduit 351 such as an optical fiber as described herein. A variable bend 760 can be provided near the fluid delivery element such as an orifice jewel 762 on the distal end. The optical fiber can be aligned with structures as shown in FIG. 31B. For example, a fiber guide 764 can be used to locate the optical fiber coaxially with the orifice of the fluid jet.

The single tube design in accordance with the embodiments of FIGS. 30, 31A and 31B can provide many advantages. For example, package size and complexity can be greatly reduced when utilizing a single tube design. Internal laminar flow characteristics can be improved with a single tube design as the fluid path can be more continuous than with other designs, for example. The orifice jewel can be swaged in place or a small cover can be laser welded to retain the jewel. Optical fiber integration can be achieved through the use of an internal fiber alignment structure. The bend angle and radius can be varied so as to allow for alternate tissue targeting or for manufacturing. Multiple jets can be employed to balance jet reaction courses and cut more than one location concurrently. For example, opposing jets can be used. An additional jet may be added to power rotational motion of the catheter for example.

The small package size can allow the implementation to take the form of a small catheter. This can allow for use with prior commercially available rigid and flexible introducers and scopes. The distal tip shapes can be preformed with a given bend angle to access a tissue volume.

Figure 32:
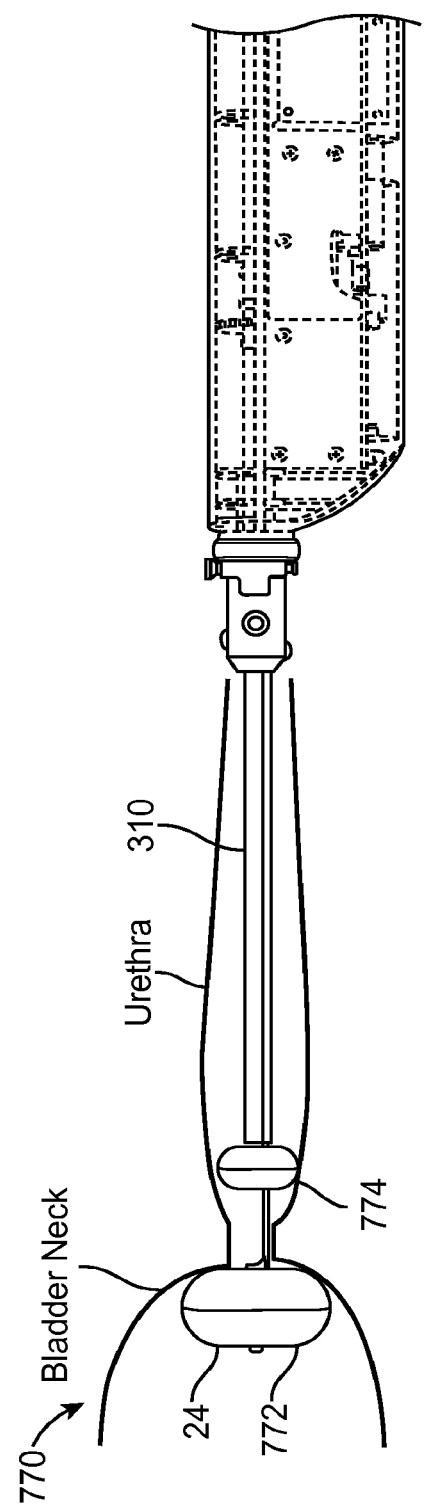
FIG. 32 shows means of registering and locating the treatment system with respect to the human anatomy in accordance with embodiments.

FIG. 32 shows means of registering and locating the treatment system with respect to the human anatomy in accordance with embodiments. A plurality of expandable anchor 770 comprises a first expandable anchor 772 and a second expandable anchor 774. The first expandable anchor 772 may comprise a balloon, for example, and the second expandable anchor 774 may comprise a second balloon, for example. The first expandable structure can be configured to expand in the bladder neck, and the second expandable structure can be configured to expand within the urethra so as to contain movement of the device.

Figure 33:
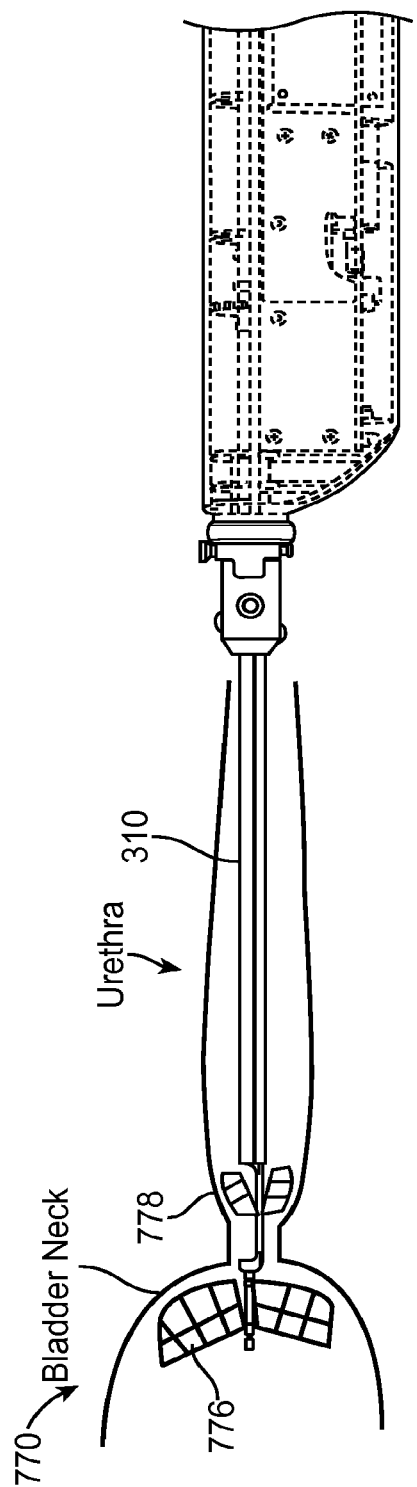
FIG. 33 shows a plurality of expandable structures comprising a first expandable basket and a second expandable basket in accordance with embodiments.

FIG. 33 shows a plurality of expandable structures comprising a first expandable basket 776 and a second expandable basket 778. The expandable basket can be permeable or nonpermeable and can be expanded to allow anchoring. The nonpermeable basket can inhibit fluid flow through the urethra, while the permeable expandable basket can allow fluid flow through the urethra and between the urethra and the bladder.

The plurality of expandable structures can have the benefit of limiting movement of the probe, both from the bladder toward the urethra and also movement from the urethra toward the bladder neck, so as to effectively lock the anchor in place.

Figure 34:
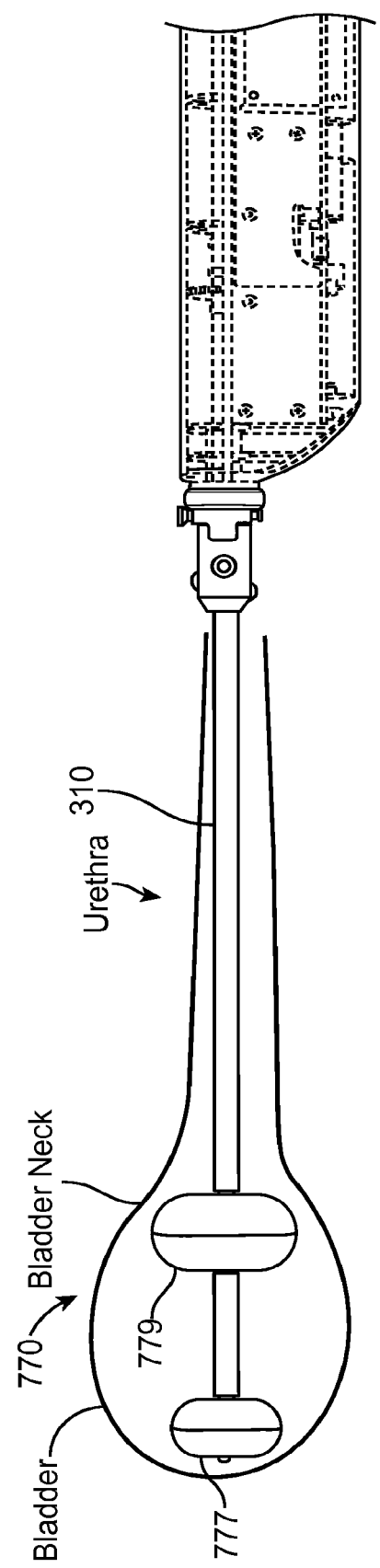
FIG. 34 shows means of registering the system with respect to the human anatomy in accordance with embodiments.

FIG. 34 shows means of registering the system with respect to the human anatomy. For example, a plurality of expandable anchors 770 may comprise a first expandable anchor 777 and a second expandable anchor 779. The first expandable anchor 777 may comprise a balloon or a basket, for example. The expandable anchor 777 is used to position against a posterior wall of the bladder. The second expandable anchor is positioned in the bladder neck. The first expandable anchor and the second expandable anchor can lock the position of the probe so as to inhibit movement. Opposing forces can be applied manually or via robotic control.

In some embodiments, an opposing force can be applied between the first expandable anchor and the second expandable anchor, so as to urge the first expandable anchor toward the bladder wall and the second expandable anchor toward the neck of the bladder.

Additional anchoring op embodiments can be provided in accordance with the teachings described herein. For example, a suction means can be used for anchoring. Alternatively, sensors for patient movement can be used. An arm can be used for anchoring. Clamps can be provided on the groin for anchoring. Magnetic forces can be used to hold the system in place. An attachment to tissue can be provided with suction. Each of these provide nonlimiting examples of anchoring means in accordance with the embodiments described herein.

Figure 35:
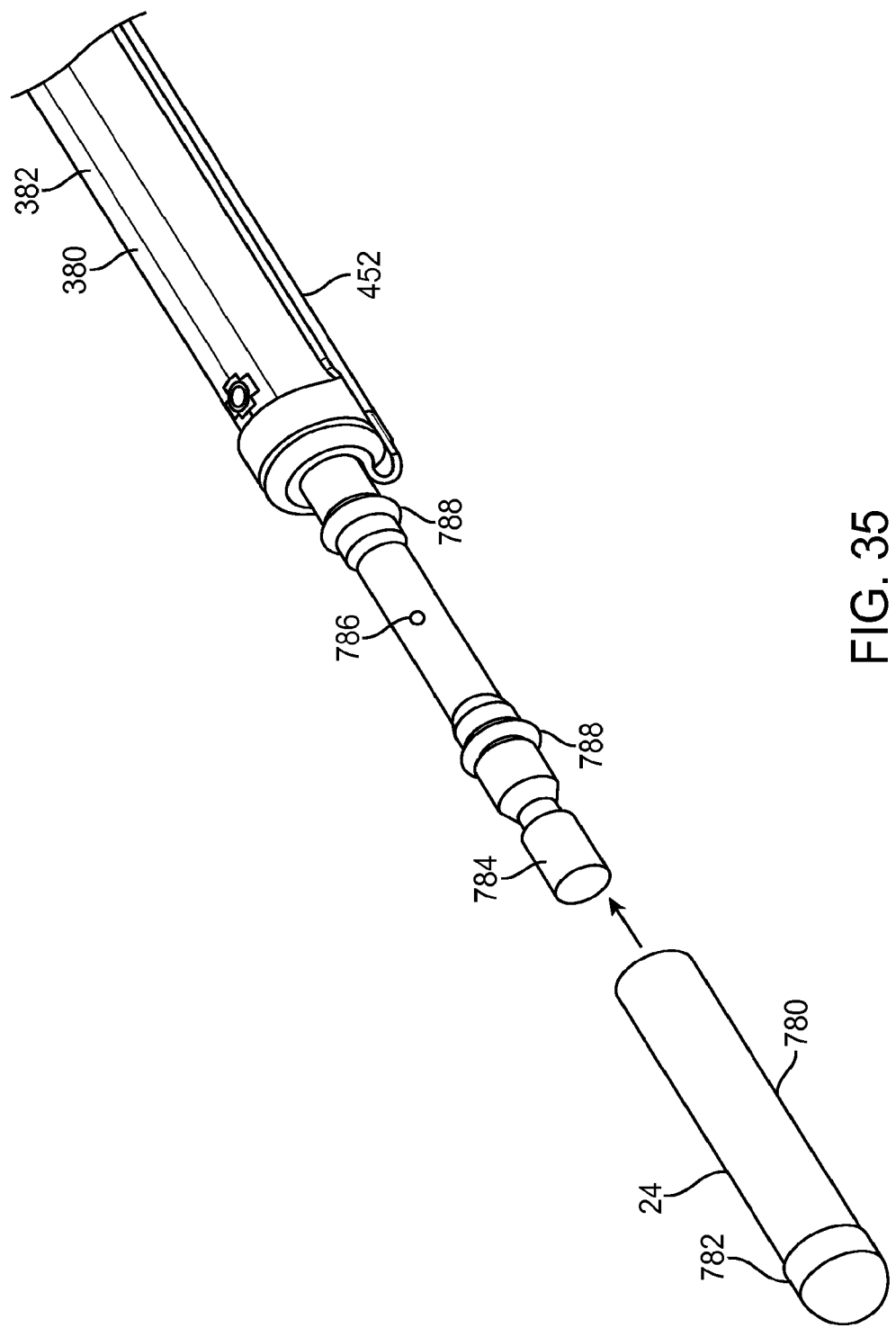
FIG. 35 shows a disposable balloon in accordance with embodiments.

FIG. 35 shows a disposable balloon in accordance with embodiments. The disposable balloon 780 can be threaded onto a distal end of the carrier 382. The disposable balloon may comprise internal threads in the tip of the balloon. Internal thread 782 can engage external thread 784. Threaded engagement between the balloon and the carrier can allow the balloon to be removed subsequent to treatment and the carrier 382 can be sterilized. An inflation hole can be provided. The inflation hole 786 allows inflation of the balloon 780 when the balloon 780 has been threadedly engaged on the distal tip. The disposable balloon can be sterilized individually. The threaded attachment of the balloon can be provided to a hand piece or to the carrier as described herein. Sealing can be achieved with the O-rings 788 and threaded engagement. A balloon capable of achieving a 1 to 7 collapsed to inflated ratio can be provided.

Figure 37:
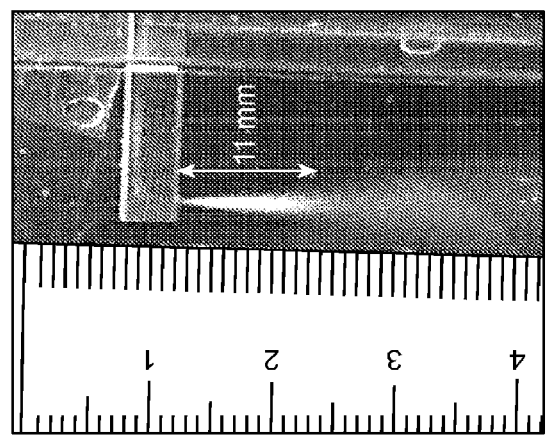
FIG. 37 shows the visible entrainment region at a first size as is shown in FIG. 36.
Figure 36:
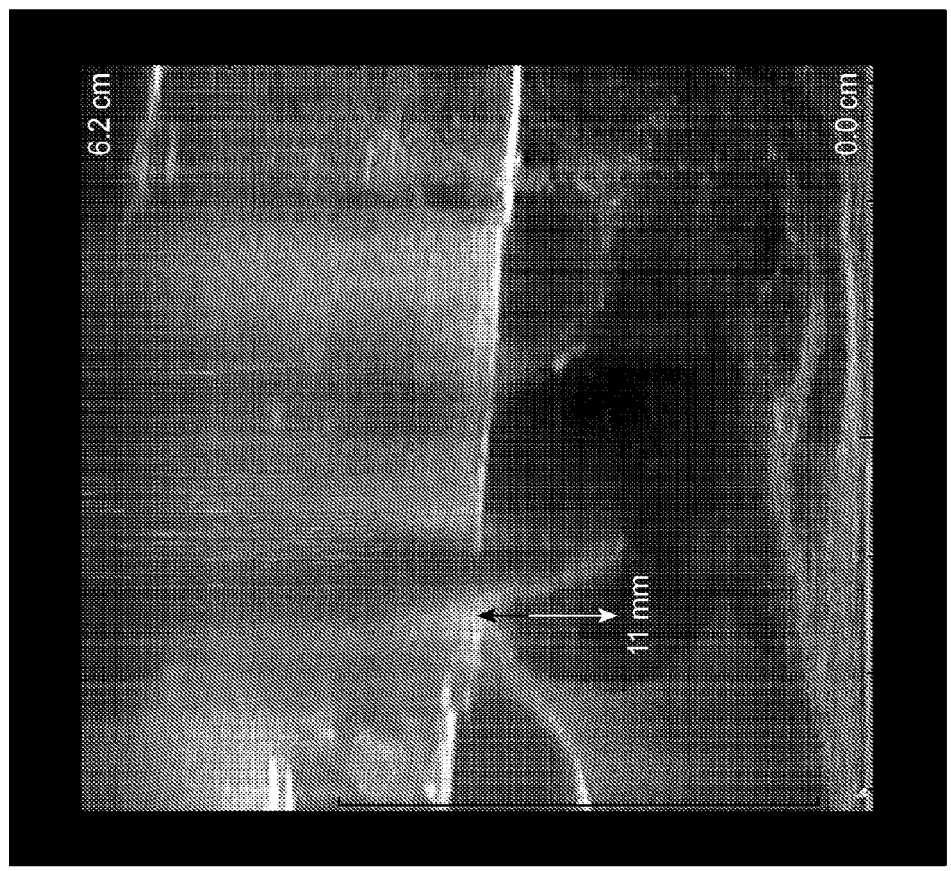
FIG. 36 shows tissue resection and depth control in accordance with embodiments.

FIG. 36 shows tissue resection and depth control in accordance with embodiments. A live patient ultrasound image is shown. FIG. 37 shows a visible fluid flame in saline. The visible fluid flame in saline corresponds to the entrainment region of the jet as described herein. The visibility of the fluid flame of the entrainment region is provided with cavitation of small bubbles that can produce light scattering or acoustic scattering, so as to make the fluid flame of the entrainment region visible with imaging by ultrasound or optical imaging, for example. The benefit of the visible entrainment region can be for a physician to visualize the distance of the treatment and to compare this distance with ultrasound. FIG. 37 shows the visible entrainment region at 11 millimeters, the same size as is shown in FIG. 36. The substantial similarity of the distance of the entrainment region corresponds to the distance of tissue resection and removal. This experimental result showing the visualization of the entrainment region can provide for a safer treatment. Merely by way of example, the flow parameters used with the images shown in FIGS. 36 and 37 comprise a flow rate of approximately 130 milliliters per minute and a nozzle back pressure of approximately 2700 psi. The configuration of the nozzle on the carrier comprise a first liquid emitted with a divergent stream as described herein into a second fluid so as to provide the divergent stream. The second fluid comprises a liquid.

A physician when treating a patient, can use a live patient ultrasounds, for example, transrectal ultrasound (hereinafter "TRUS") as described herein. The physician can do the ultrasound in the entrainment region from the probe tip. This can be used to determine the appropriate parameters to treat the patient. For example, the physician can adjust the pressure so as to limit the depth of penetration of the probe tip such that the probe tip does not release energy to cause cutting outside of the organ, for example, beyond the sack of the organ such as the sack of the prostate. The image of FIG. 36 shows on the left hand side of the image a structure corresponding to an expandable balloon and the arrows show the 11 millimeter dimension. FIG. 37 is an optical image showing a similar distance of the entrainment region. The sweeping motion of the stream shown in FIG. 36 can be used to adjust the treatment to be contained within the prostate.

Figure 38:
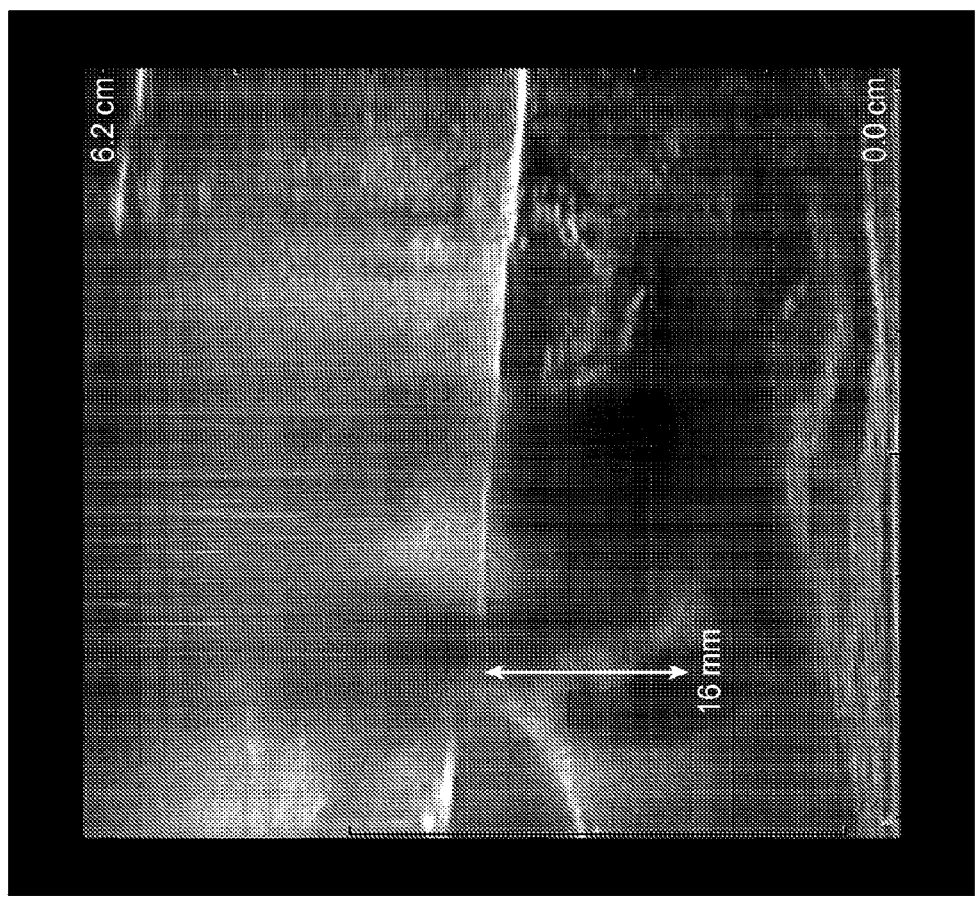
FIG. 38 shows tissue resection depth control in accordance with embodiments.

FIG. 38 shows tissue resection depth control in accordance with embodiments. Live patient ultrasound from the patient is shown in FIG. 38 similar to FIG. 37, but with increased back stream pressure to the nozzle.

Figure 39:
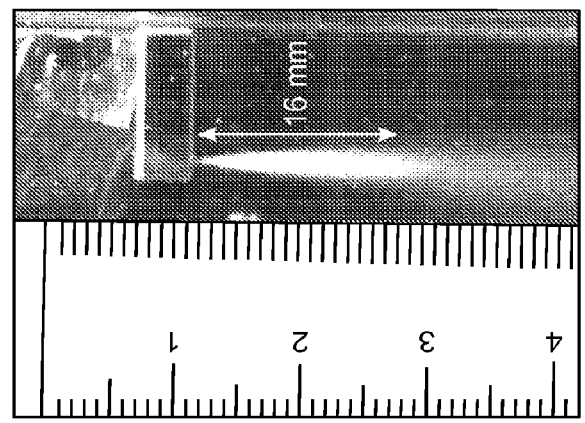
FIG. 39 shows an optical image of the entrainment region "flame" in saline as shown in FIG. 38 with a different pressure than is shown in FIGS. 36 and 37, in accordance with embodiments.

FIG. 39 shows an optical image of the fluid flame in saline showing the entrainment region with a different pressure. The pressure flow parameters for FIGS. 38 and 39 comprise an approximate flow rate of 205 milliliters per minute and the nozzle back pressure of approximately 5760 psi. The corresponding tissue resection depth is approximately 16 millimeters. The live patient ultrasound image shows an entrainment region of 16 millimeters similar to the entrainment region seen optically. The sweeping motion of the probe and the fluid stream emitted from the probe as seen on the left hand side of the image can be used to set the flow parameters and pressure so as to treat the patient safely with ultrasound images of the entrainment region.

Figure 40:
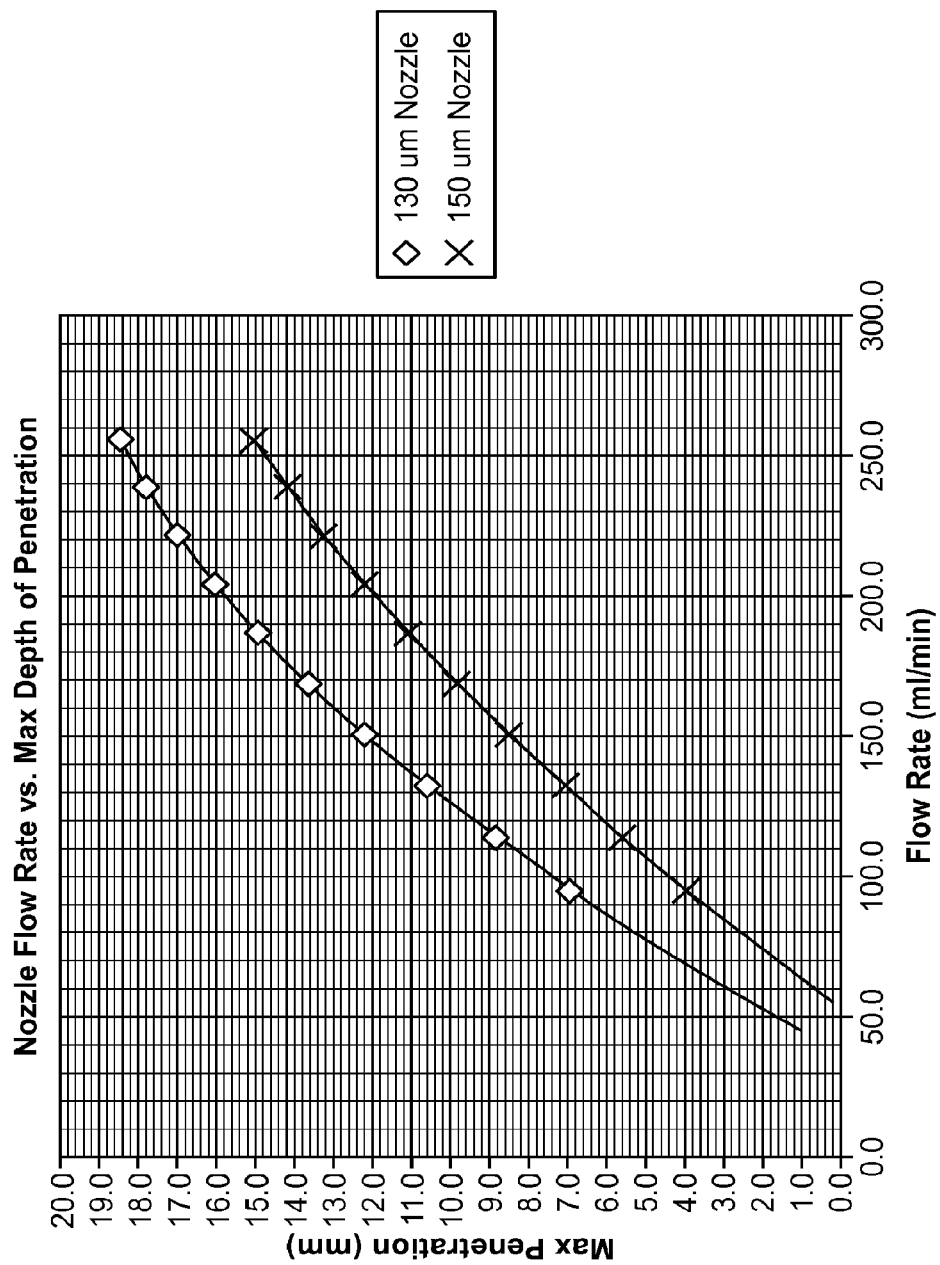
FIG. 40 shows nozzle flow rate versus maximum penetration depth for a plurality of pressures and nozzles in accordance with embodiments.

FIG. 40 shows nozzle flow rate versus maximum penetration depth for a plurality of pressures and nozzles. The flow rate in milliliters per minute is shown. The maximum penetration depth is also shown as a function of the flow rate. 130 micron nozzle shows a tissue penetration depth with diamonds and the 150 micron nozzle is shown with X's. The tissue penetration depth can be used based on the teachings described herein to set the flow rate parameters for treatment. For example, for a treatment to a maximum penetration depth of 12 millimeters or 130 micrometer nozzle, a flow rate of 150 milliliters per minute is selected. Similarly, for the 150 micron nozzle, a flow rate of 200 milliliters per minute is selected. A person of ordinary skill in the art can construct software to automatically identify a nozzle for treatment based on depth and also to identify a flow rate suitable for treatment based on depth. In addition, the flow rate can be varied based on the tissue profile as described herein. For example, tissue treatment profiles based on axial and sagittal images as described herein.

Figure 41:
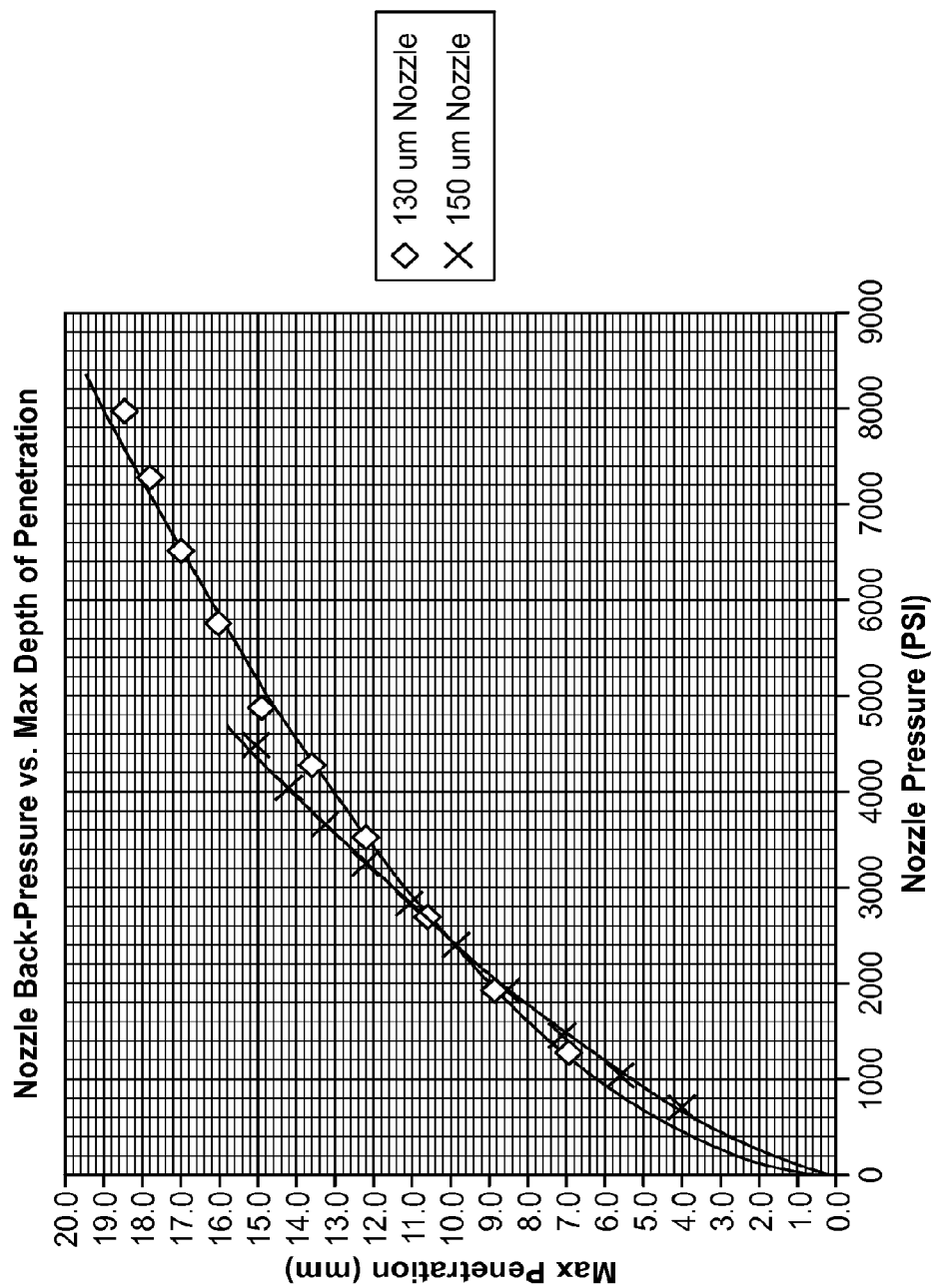
FIG. 41 shows nozzle back pressure versus maximum depth of penetration in accordance with embodiments.

FIG. 41 shows nozzle back pressure versus maximum depth of penetration. Maximum penetration in millimeters is shown as a function of nozzle pressure in psi for both 130 micron nozzle and 150 micron nozzle. Based on the identified nozzle size and tissue penetration depth, the software or user can identify an appropriate nozzle pressure to treat the patient.

Figure 42:
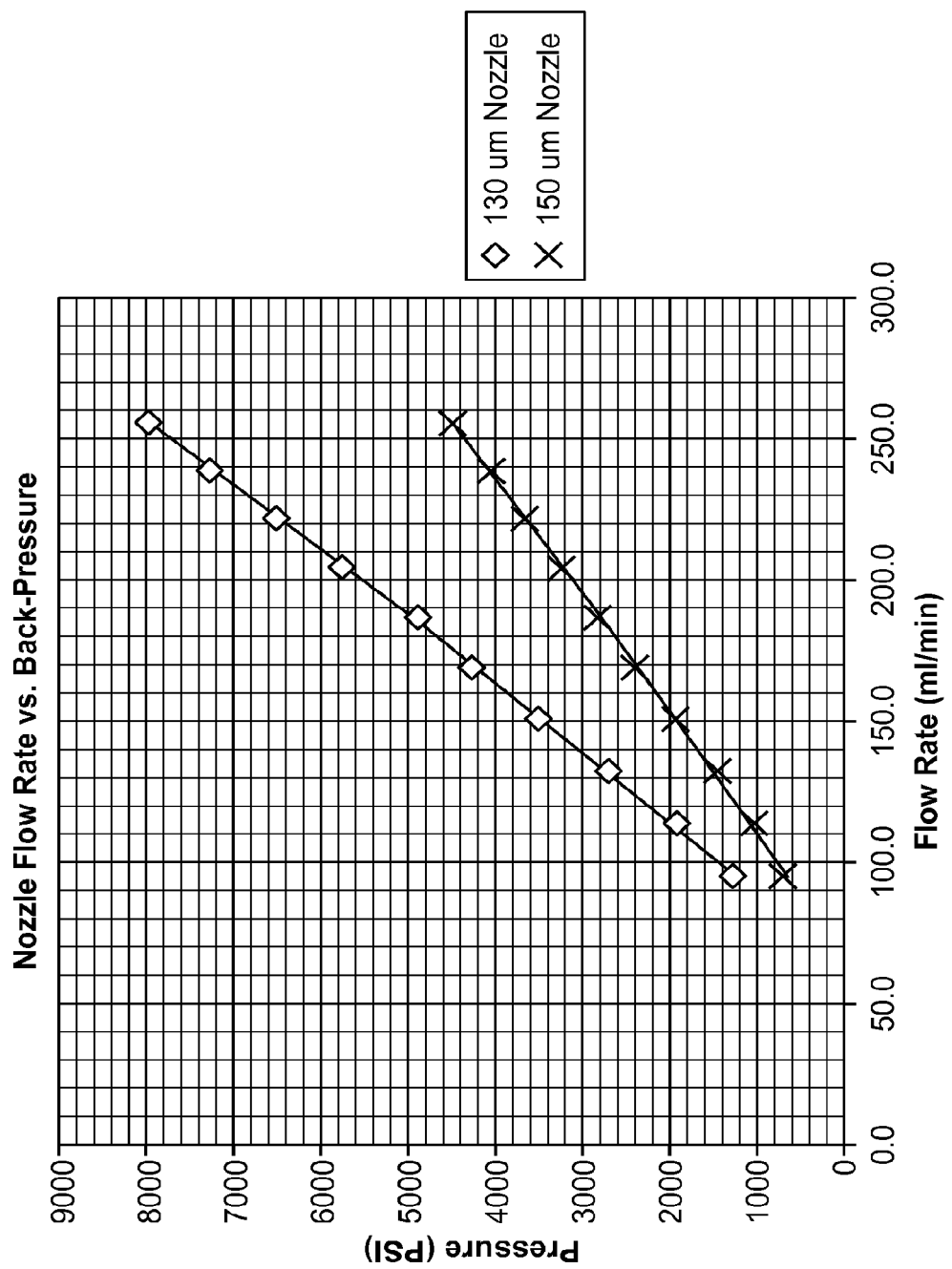
FIG. 42 shows nozzle flow rate versus back pressure for 130 micron nozzle and 150 micron nozzle in accordance with embodiments.

FIG. 42 shows nozzle flow rate versus back pressure for 130 micron nozzle and 150 micron nozzle. The pressure and flow rate are shown. For a flow rate, the flow rate is shown in milliliters per minute and the pressure is shown in psi. The flow rate can be from about 100 milliliters per minute to about 250 milliliters per minute, and the pressure can be from under 1000 psi to as high as 4000 psi or, for example, 8000 psi. In specific embodiments, the flow rate with a larger diameter nozzle is approximately linear with the pressure and the flow rate with the 130 micron nozzle is approximately linear with pressure. These relationships of flow rate and pressure can be used to appropriately set the pressure for treatment for desired flow rate. Furthermore, these flow rate pressure relationships can be non-linear when the range is expanded to lower values, or higher values, or both. Alternatively or in combination, the flow rate pressure relationships can be non-linear when different nozzles with different characteristics are used, for example.

A person of ordinary skill in the art can use the one or more of the nozzle pressure, cut depth and flow rates to resect tissue to a predefined profile and volume as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A prostate resection apparatus, comprising:
a carrier having a proximal end and a distal end;
at least one energy source on the carrier spaced proximally to be positioned in the urethra when for delivering energy radially outwardly;
an automated controller for controlling movement of the at least one energy source to effect volumetric tissue removal; and
a processor comprising instructions configured:
to provide an image of a prostate on a display visible to a user; and
to receive a plurality of input parameters corresponding to an axial length and a radial distance of a pre-defined volume of tissue;
wherein a predefined tissue removal profile of the pre-defined volume is shown on the image of the prostate on the display based on the plurality of input parameters.

2. An apparatus as in claim 1, wherein the plurality of input parameters comprises one or more of a longitudinal distance of the removal profile, a radial distance of the removal profile, an angular distance of the removal profile around a longitudinal axis of the removal profile, an axis of the removal profile, a central location of the removal profile, or a user defined input removal profile in response to the user moving a pointer over the image of the prostate.

3. An apparatus as in claim 2, wherein the image of the prostate comprises an axial view of the prostate and a sagittal view of the prostate, and wherein an axial view of the pre-defined tissue removal profile is shown on the axial view of the prostate and sagittal view of the tissue removal profile is shown on the sagittal view of the prostate.

4. An apparatus as in claim 3, wherein the processor comprises instructions to adjust the axial view of the predefined removal profile based on the radial distance and the angular distance of the predefined removal profile and wherein the processor comprises instructions to adjust the axial view of the predefined removal profile based on the axial distance and the radial distance of the predefined removal profile.

5. An apparatus as in claim 1, wherein the tissue removal profile shown on the image of the prostate comprise dimensions scaled to the image of the prostate shown on the display such that dimensions of the tissue removal profile shown on the display correspond to dimensions of the image of the prostate shown on the display.

6. An apparatus as in claim 1, wherein the processor comprises instructions to show a treatment reference marker with the image of the prostate and to show the tissue removal profile on the display in relation to the treatment reference marker based on the plurality of input parameters.

7. An apparatus as in claim 6, wherein the treatment reference marker shown on the display corresponds to an anchor connected to the energy source.

8. An apparatus as in claim 6, wherein the treatment reference marker shown on the display corresponds to an expandable anchor connected to the energy source and wherein the expandable anchor comprises a first narrow profile configuration sized for insertion into the lumen and a second wide profile configuration to inhibit passage through the lumen when placed in a neck of a bladder of the patient and wherein the treatment reference marker shown on the display comprises an image of an expandable anchor in a wide profile configuration on a superior end of a sagittal image of the prostate.

9. An apparatus as in claim 6, wherein the treatment reference marker shown on the display comprises a fixed reference marker, and wherein the processor comprises instructions to show a movable marker that moves in relation to the fixed reference marker and the treatment profile to show a location of an energy stream to a target tissue in real time.

10. An apparatus as in claim 9, wherein the movable marker is shown a plurality of images, the plurality of images comprising a sagittal image along a sagittal axis of treatment and an axial image transverse to the axis of treatment, and wherein the movable marker moves along the axis of treatment in the sagittal image and the movable marker rotates around the axis in the axial image and wherein the fixed reference marker is displayed on each of the plurality of images in relation to the movable marker.

11. An apparatus as in claim 1, wherein the image of the prostate shown on the display comprises an image of the prostate of the patient or an anatomical representation of a prostate suitable for use with a plurality of patients.

12. An apparatus as in claim 11, wherein the image of the prostate of the patient shown on the display comprises a transrectal ultrasound image of the prostate of the patient.

13. An apparatus as in claim 1, wherein the processor comprises instructions to identify a nozzle among a plurality of nozzles to treat the patient with a pressurized fluid stream based on a radial distance of the tissue removal profile input into the processor.

14. An apparatus as in claim 13, wherein the processor comprises instructions to coagulate tissue with a light beam at a radial distance and an angular distance of a portion of the tissue removal profile subsequent to removal of the tissue with the pressurized fluid steam and wherein the angular distance corresponds to a posterior portion of the removal profile.

15. An apparatus as in claim 14, wherein the fluid stream comprises a divergent stream of a substantially incompressible fluid and wherein the light beam comprises a divergent light beam.

16. An apparatus as in claim 1, wherein a treatment axis of the pre-defined treatment volume is aligned with an axis of the patient based on an image of the prostate and energy emitted radially from the probe.

17. An apparatus as in claim 16, wherein the axis of the pre-defined volume comprises an anterior-posterior axis of the treatment volume and wherein the anterior-posterior axis of the treatment volume is aligned with an anterior posterior direction of the patient based on visualization of the tissue and an angle of energy emitted radially from the probe in order to rotationally align the treatment energy emitted from the probe with the anterior-posterior direction of the patient.

18. An apparatus as in claim 17, wherein the image comprises an ultrasound image showing one or more of deflection of the tissue or a fluid stream in response to pressurized fluid released from a nozzle and wherein an angle of the fluid stream around an elongate axis of a treatment probe is adjusted to align the treatment axis with the axis of the patient.

19. An apparatus as in claim 17, wherein the image comprises an optical image showing a light beam emitted radially from the probe illuminating the tissue and wherein an angle of the light beam around an elongate axis of the treatment probe is adjusted to align the treatment axis with the patient.

20. An apparatus as in claim 17, further comprising a processor and wherein the processor comprises instructions for the user to adjust an angle of the energy radially emitted from the treatment probe around an elongate axis of the treatment probe to align the energy radially emitted with an axis of the patient and wherein the processor comprises instructions to input the angle in response to a user command when the angle of the energy is aligned with the axis of the patient and wherein the processor comprises instructions to rotate the treatment axis based on the angle input into the processor.

21. An apparatus as in claim 16, wherein an angular rotation sensor determines a rotation of the treatment probe around an elongate axis of the probe in relation to an axis of the patient and wherein a treatment axis of the pre-defined treatment volume is rotated in response to the rotation of the treatment probe and wherein the patient is placed on a patient support such that an anterior posterior direction of the patient is aligned with a direction of gravitational pull.

22. An apparatus as in claim 21, the angular rotation sensor comprises one or more of an accelerometer or a goniometer.

23. An apparatus as in claim 1, wherein the apparatus is configured to remove living cells of the tissue in order to provide the living cells outside the patient.

\* \* \* \* \*